(12) United States Patent
Hug et al.

(10) Patent No.: US 12,280,087 B2
(45) Date of Patent: Apr. 22, 2025

(54) COMPOSITION COMPRISING SELF-ASSEMBLING PEPTIDES FOR USE IN TREATMENT OF GINGIVITIS, PERIODONTITIS AND/OR PERI-IMPLANTITIS

(71) Applicant: Credentis AG, Windisch (CH)

(72) Inventors: Michael Hug, Zofingen (CH); Dominikus Amadeus Lysek, Windisch (CH); Franziska Koch, Kandern-Tannenkirch (DE); Ronald Jung, Küsnacht (CH); Stephanie Mathes, Neftenbach (CH); Nina Meyer, Zürich (CH); Christoph Hämmerle, Benglen (CH); Frank Bröseler, Aachen (DE); Uwe Pieles, Müllheim/Baden (DE)

(73) Assignee: Credentis AG, Windisch (CH)

(*) Notice: Subject to any disclaimer, the term of this patent is extended or adjusted under 35 U.S.C. 154(b) by 498 days.

(21) Appl. No.: 16/319,943

(22) PCT Filed: Aug. 16, 2017

(86) PCT No.: PCT/EP2017/070758
§ 371 (c)(1),
(2) Date: Jan. 23, 2019

(87) PCT Pub. No.: WO2018/033570
PCT Pub. Date: Feb. 22, 2018

(65) Prior Publication Data
US 2019/0247540 A1    Aug. 15, 2019

(30) Foreign Application Priority Data

Aug. 16, 2016  (EP) .................................. 16184309
Nov. 25, 2016  (EP) .................................. 16200655

(51) Int. Cl.
| | | |
|---|---|---|
| *A61K 38/08* | (2019.01) | |
| *A61K 8/64* | (2006.01) | |
| *A61K 9/00* | (2006.01) | |
| *A61K 45/06* | (2006.01) | |
| *A61L 27/22* | (2006.01) | |
| *A61L 27/52* | (2006.01) | |
| *A61L 27/54* | (2006.01) | |
| *A61L 31/04* | (2006.01) | |
| *A61L 31/14* | (2006.01) | |
| *A61L 31/16* | (2006.01) | |
| *A61Q 11/00* | (2006.01) | |
| *A61P 1/02* | (2006.01) | |
| *A61P 31/04* | (2006.01) | |

(52) U.S. Cl.
CPC .............. *A61K 38/08* (2013.01); *A61K 8/64* (2013.01); *A61K 9/006* (2013.01); *A61K 9/0063* (2013.01); *A61K 45/06* (2013.01); *A61L 27/227* (2013.01); *A61L 27/52* (2013.01); *A61L 27/54* (2013.01); *A61L 31/047* (2013.01); *A61L 31/145* (2013.01); *A61L 31/16* (2013.01); *A61Q 11/00* (2013.01); *A61L 2300/406* (2013.01); *A61L 2300/41* (2013.01); *A61L 2430/12* (2013.01); *A61P 1/02* (2018.01); *A61P 31/04* (2018.01)

(58) Field of Classification Search
None
See application file for complete search history.

(56) References Cited

U.S. PATENT DOCUMENTS

| | | | |
|---|---|---|---|
| 2,994,642 A * | 8/1961 | Bossard ................. | A61Q 11/00 424/401 |
| 10,047,120 B2 | 8/2018 | Hug et al. | |
| 2006/0154852 A1 | 7/2006 | Boden et al. | |
| 2010/0234304 A1 | 9/2010 | Boden et al. | |
| 2012/0014925 A1 | 1/2012 | Kumada | |
| 2012/0156649 A1* | 6/2012 | Golden ................. | A61C 17/00 424/93.7 |

(Continued)

FOREIGN PATENT DOCUMENTS

| | | |
|---|---|---|
| EP | 2853256 A1 | 4/2015 |
| JP | 2007105186 A | 4/2007 |

(Continued)

OTHER PUBLICATIONS

Consensus Sequence—MeSH—NCBI, (1991), two pages. (Year: 1991).*

(Continued)

*Primary Examiner* — Thomas S Heard
(74) *Attorney, Agent, or Firm* — Thomas | Horstemeyer, LLP

(57) ABSTRACT

The present invention provides a composition comprising specific self-assembling peptides, which are capable of self-assembly at a pH below 7.5 and at least physiologic ionic strength, e.g., PI 1-4. PI 1-8, PI 1-14, PI 1-13, PI 1-12, PI 1-28, PI 1-29, PI 1-2, PI 1-5, PI 1-17, PI 1-19, PI 1-20, PI 1-12, PI 1-16, PI 1-18, PI 1-26 or PI 1-31 for use in treating an oral disease selected from the group consisting of gingivitis, periodontitis and/or peri-implantitis in a subject. Said composition may be used, after suitable cleaning procedures, for filling pockets formed adjacent to teeth in said diseases, which enhances tissue regeneration. The composition may be suitable for controlled release of an active agent, e.g., an antimicrobial or antibiotic agent. The invention also provides a kit suitable for said treatment further comprising self-assembling peptides suitable for forming a second layer on top of the first composition.

19 Claims, 21 Drawing Sheets
Specification includes a Sequence Listing.

(56) References Cited

U.S. PATENT DOCUMENTS

| | | | |
|---|---|---|---|
| 2013/0012457 A1 | 1/2013 | Boden et al. | |
| 2014/0044649 A1 | 2/2014 | Boden et al. | |
| 2015/0352023 A1* | 12/2015 | Berg | A61K 8/43 433/119 |
| 2016/0199283 A1 | 7/2016 | Hug et al. | |
| 2018/0340010 A1 | 11/2018 | Hug et al. | |

FOREIGN PATENT DOCUMENTS

| | | |
|---|---|---|
| WO | 2003006494 A1 | 1/2003 |
| WO | 2004007532 A1 | 1/2004 |
| WO | 2014027012 A1 | 2/2014 |
| WO | 2014167310 A1 | 10/2014 |
| WO | 2015196020 A1 | 12/2015 |

OTHER PUBLICATIONS

Takeuchi et al., Enhanced healing of surgical periodontal defects in rats following application of a selfassembling peptide nanofibre hydrogel, J Clin Periodontol 43: p. 279-288, 2016.
Databse WPI Week 200736, XP-002528834, Thomson Scientific, London, GB.
Scanlon et al., Organisation of self-assembling peptide nanostructures into macroscopically ordered lamella-like layers by ice crystallisation, Soft Matter, 5, p. 1237-1246, 2009.
Scanlon et al., Peptide aerogels comprising self-assembling nanofibrils, Micro & Nano Letters 2, (2), p. 24-29, 2007.
International Search Report for application PCT/EP2017/070758, dated Mar. 11, 2017.
Ahuja et al., Role of antibiotics in generalized aggressive periodontitis: A review of clinical trials in humans, J Indian Soc Periodontol, 16(3): 317-323, 2012.
Cigognini et al., Evaluation of Early and Late Effects into the Acute Spinal Cord Injury of an Injectable Functionalized Self-Assembling Scaffold, PLoS One, vol. 6, Issue 5, 1-15, 2011.
Diedrich et al., Movement of Periodontally Affected Teeth after Guided Tissue Regeneration (GTR)—an Experimental Pilot Study in Animals, J Orofac Orthop, No. 3, 214-227, 2003.
Gelain et al., Designer Self-Assembling Peptide Nanofiber Scaffolds for Adult Mouse Neural Stem Cell 3-Dimensional Cultures, PLoS One, Issue 1, 1-10, 2006.
Gungormus et al., Cementomimetics—constructing a cementum-like biomineralized microlayer via amelogenin-derived peptides, International Journal of Oral Science, 4, 69-77, 2012.
Ho et al., The effects of concentration-dependent morphology of self-assembling RADA 16 nanoscaffolds on mixed retinal cultures, Nanoscale, 3, 907-910, 2011.
Hoang et al., In Vitro Wound Healing Responses to Enamel Matrix Derivative, J Periodontol, vol. 71, No. 8, 1270-1277, 2000.
Holmes et al, Extensive neurite outgrowth and active synapse formation on self-assembling peptide scaffolds, PNAS, vol. 97, No. 12, 6728-6733, 2000.
Jiang et al., Enamel Matrix Derivative Prolongs Primary Osteoblast Growth, Journal of Endodontics, vol. 27, No. 2, 110-112, 2001.
Kaigler et al., Platelet-Derived Growth Factor Applications in Periodontal and Peri-Implant Bone Regeneration, Expert Opin Biol Ther., 11(3): 375-385, 2011.
Kind et al., Biomimetic Remineralization of Carious Lesions by Self-Assembling Peptide, Journal of Dental Research, 1-8, 2017.
Kisiday et al., Self-assembling peptide hydrogel fosters chondrocyte extracellular matrix production and cell division: Implications for cartilage tissue repair, PNAS, vol. 99, No. 15, 9996-10001, 2002.
Kumada et al., Significant Type I and Type III Collagen Production from Human Periodontal Ligament Fibroblasts in 3D Peptide Scaffolds without Extra Growth Factors, PLoS One, vol. 5, Issue 4, 1-7, 2010.
Leonhardt et al., Microbial findings at failing implants, Clin Oral Impl Res 10: 339-345, 1999.

Liedmann et al., Cultivation of Human Neural Progenitor Cells in a 3-dimensional Self-assembling Peptide Hydrogel, Journal of Visualized Experiments, 59, 1-5, 2012.
Liu et al., Functionalized self-assembling peptide nanofiber hydrogels mimic stem cell niche to control human adipose stem cell behavior in vitro, Acta Biomaterialia 9, 6798-6805, 2013.
Luo et al., Fabrication of self-assembling D-form peptide nanofiber scaffold d-EAK16 for rapid hemostasis, Biomaterials 32, 2013-2020, 2011.
Meyer et al., In Vitro Periodontal Ligament Model to Assess Synthetic Self Assembling Peptides for Regeneration, 2016.
Meyer et al., N Vitro Periodontal Ligament Model to Assess Synthetic Self Assembling Peptides for Regeneration, 2017.
Miller et al., Growth Factor Delivery Through Self-assembling Peptide Scaffolds, Clin Orthop Relat Res, 469:2716-2724, 2011.
Miron et al., Influence of Enamel Matrix Derivative on Cells at Different Maturation Stages of Differentiation, PLoS One, vol. 8, Issue 8, 1-8, 2013.
Mombelli et al., The characteristics of biofilms in peri-implant disease, J Clin Periodontol; 38 (Suppl. 11): 203-213, 2011.
Nevins et al., Platelet-Derived Growth Factor Promotes Periodontal Regeneration in Localized Osseous Defects: 36-Month Extension Results From a Randomized, Controlled, Double-Masked Clinical Trial, Periodontol; 84(4): 456 464, 2013.
Nune et al., Self-Assembling Peptide Nanofibrous Scaffolds for Tissue Engineering: Novel Approaches and Strategies for Effective Functional Regeneration, Current Protein and Peptide Science, 14, 70-84, 2013.
Prathapachandran et al., Management of peri-implantitis, Dent Res J (Isfahan). Sep.-Oct. 2012; 9(5): 516-521.
Scanlon et al., Peptide aerogels comprising self-assembling nanofibrilsc, Micro & Nano Letters, 2, (2), pp. 24-29, 2007.
Schwarz et al., Effect of enamel matrix protein derivative on the attachment, proliferation, and viability of human SaOs2 osteoblasts on titanium implants, Clin Oral Invest, 8:165-171, 2004.
Sculean Die Verwendung von Emdogain in der parodontalen und ossären Regeneration, 2007.
Silva et al., Selective Differentiation of Neural Progenitor Cells by High-Epitope Density Nanofibers, Science, vol. 303, 2004.
Song et al., Angiogenesis induced with neotype amphiphic peptide, (1):113-5, 2010.
Sun et al., Experimental Study on Self-assembly of KLD-12 Peptide Hydrogel and 3-D Culture of MSC Encapsulated within Hydrogel In Vitro, J Huazhong Univ Sci Technol [Med Sci] 29 (4): 2009.
Takeuchi et al., Enhanced healing of surgical periodontal defects in rats following application of a selfassembling peptide nanofibre hydrogel, J Clin Periodontol; 43: 279-288, 2016.
Thangakumaran et al., Osteoblast response (initial adhesion and alkaline phosphatase activity) following exposure to a barrier membrane/enamel matrix derivative combination, Indian Journal of Dental Research, vol. 20, Issue 1, 7-12, 2009.
Tyagi et al., Clinical Efficacy of Subgingivally Delivered 0.5% Controlled Release Azithromycin Gel in the Management of Chronic Periodontitis, Indian Journal of Medical Sciences, vol. 65, No. 6, 2011.
Tysseling et al., Self-Assembling Nanofibers Inhibit Glial Scar Formation and Promote Axon Elongation after Spinal Cord Injury, The Journal of Neuroscience, 28(14):3814-3823, 2008.
Van der Pauw, Enamel Matrix-Derived Protein Stimulates Attachment of Periodontal Ligament Fibroblasts and Enhances Alkaline Phosphatase Activity and Transforming Growth Factor β 1 Release of Per . . . , Journal of Periodontology, 2000.
Wu et al., Self-assembled IKVAV Peptide Nanofibers Promote Adherence of PC12 Cells, Journal of Huazhong University of Science and Technology, 26 (5): 594-596, 2006.
Wu et al., Effect of IKVAV Peptide Nanofiber on Proliferation, Adhesion and Differentiation into Neurocytes of Bone Marrow Stromal Cells, J Huazhong Univ Sci Technol, 30(2):178-182,2010.
Yuan et al., Self-Assembling Peptide Nanofiber as Potential Substrates in Islet Transplantation, Transplantation Proceedings, 40, 2571-2574, 2008.

(56) References Cited

OTHER PUBLICATIONS

Miron et al., Twenty years of enamel matrix derivative: the past, the present and the future, J Clin Periodontol, 43:668-683, 2016.

* cited by examiner

Fig. 1A
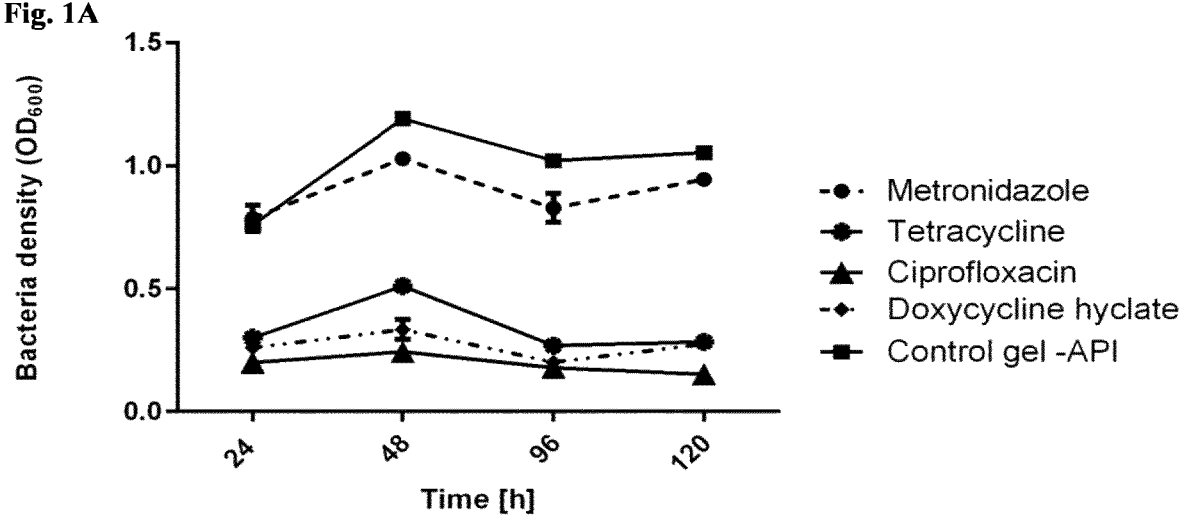
B
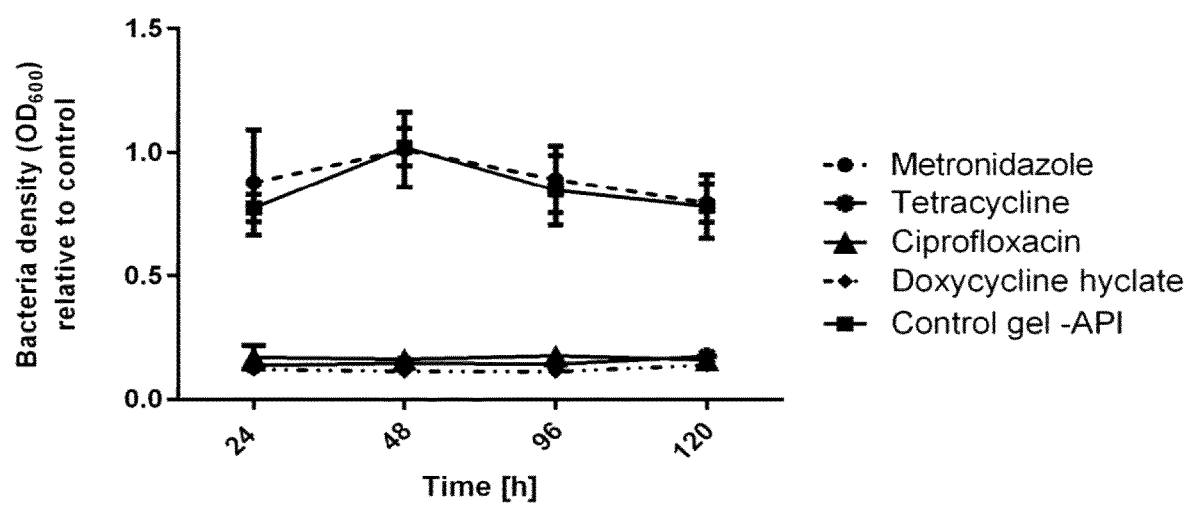
C
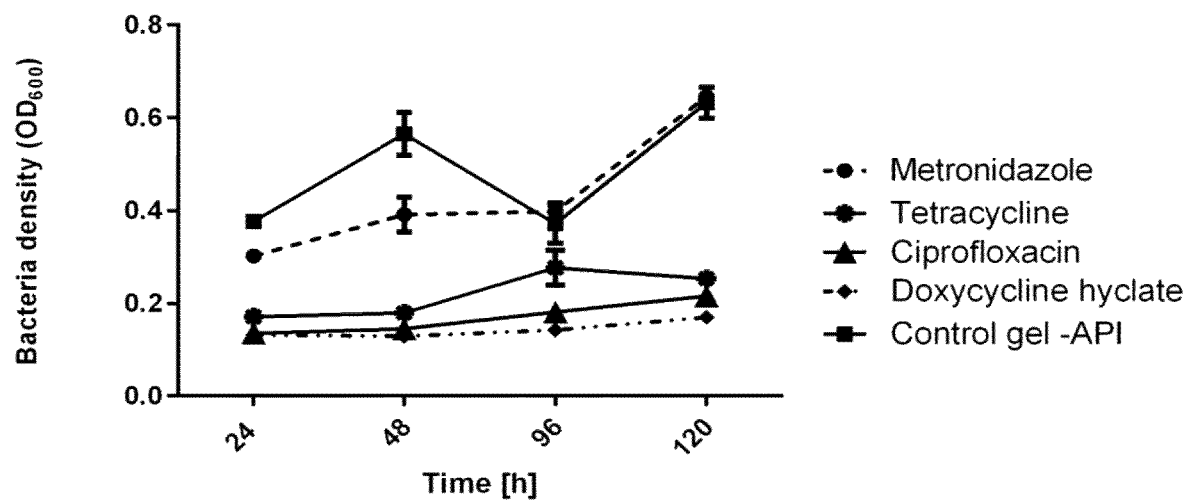

Fig. 1D
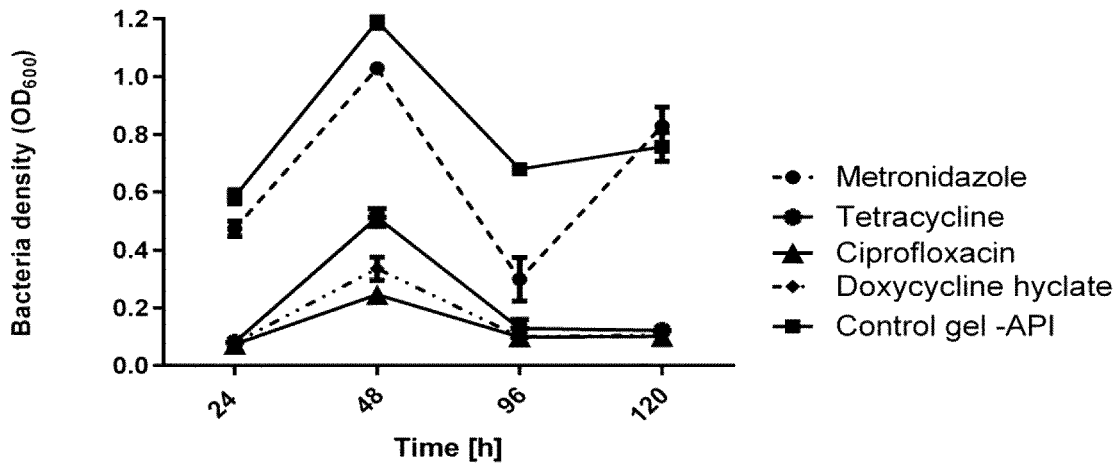
E
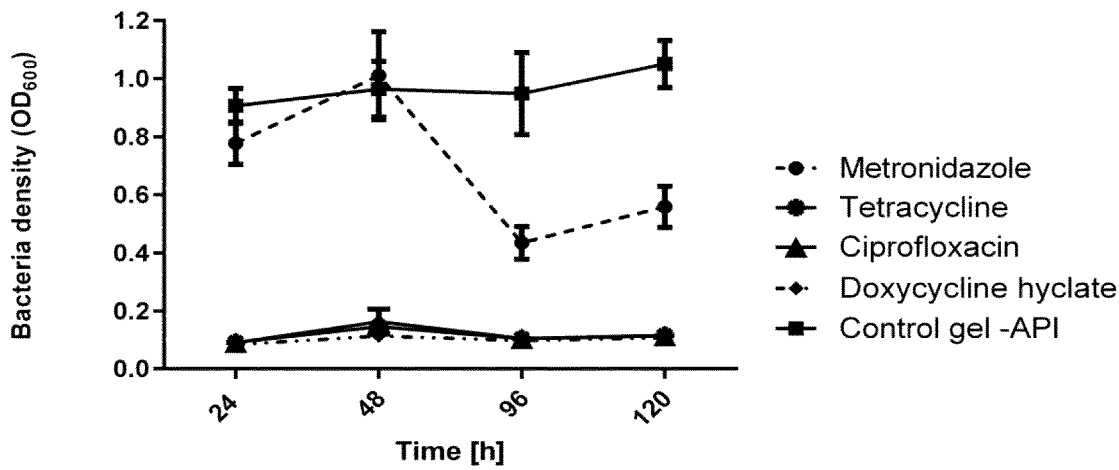
F
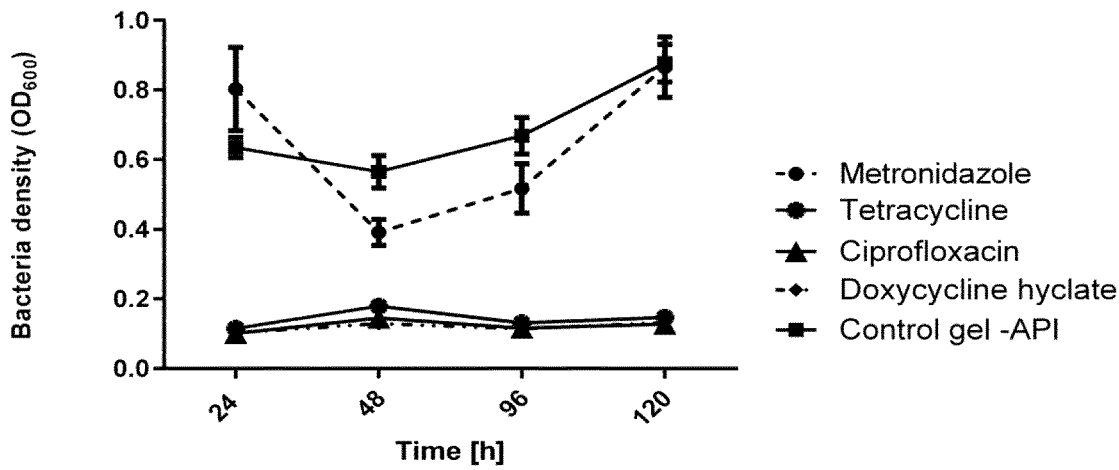

Fig. 7A
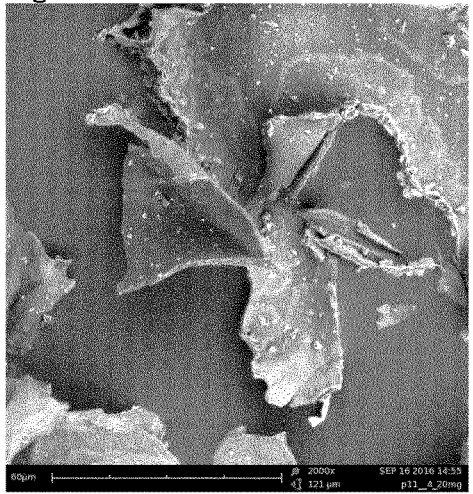
B
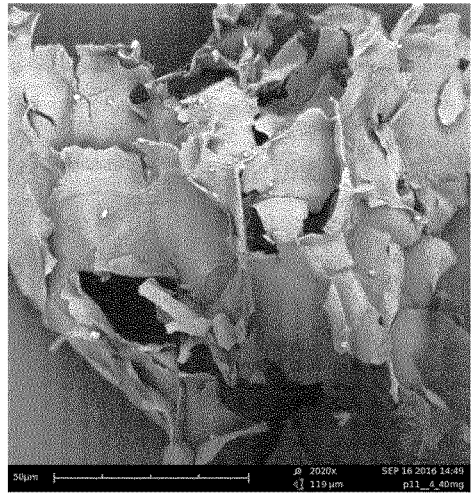
C
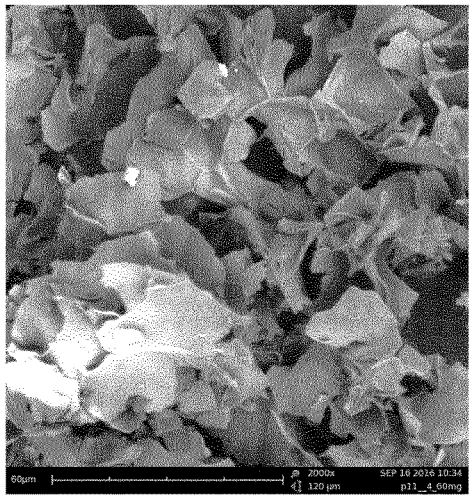
D

Fig. 8A
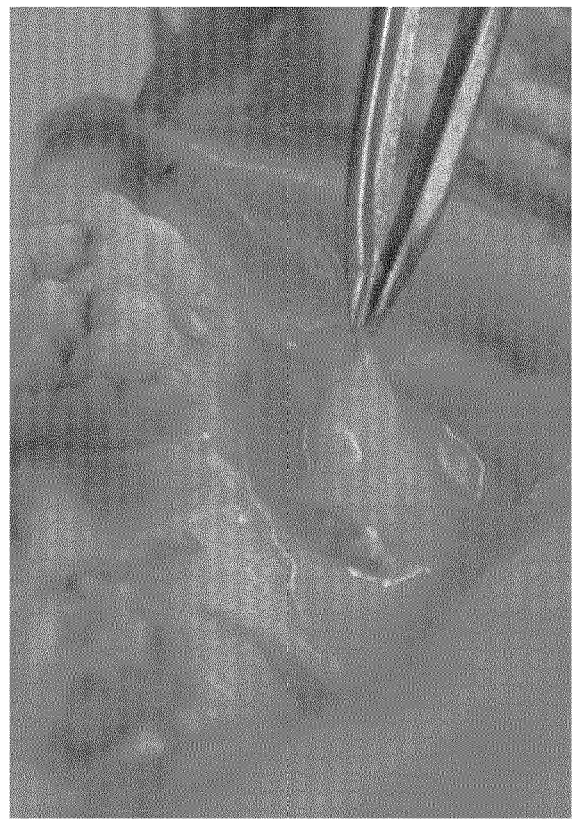
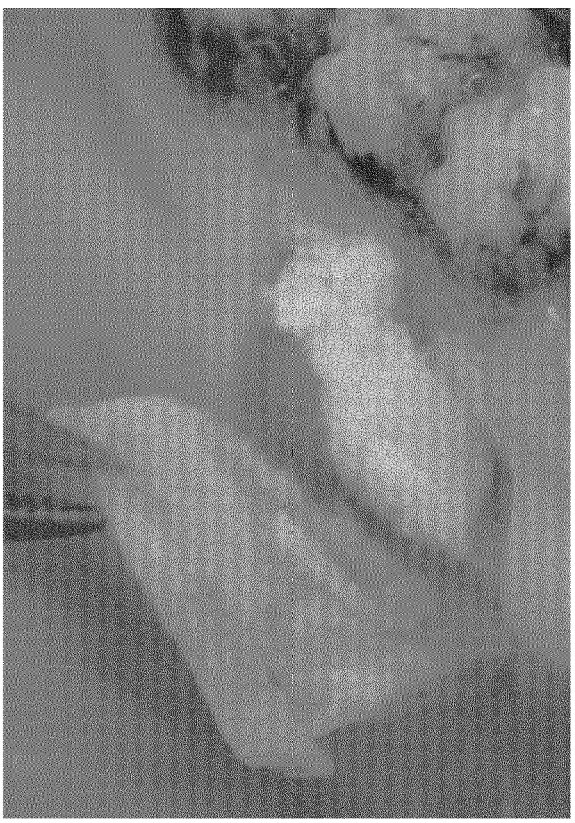
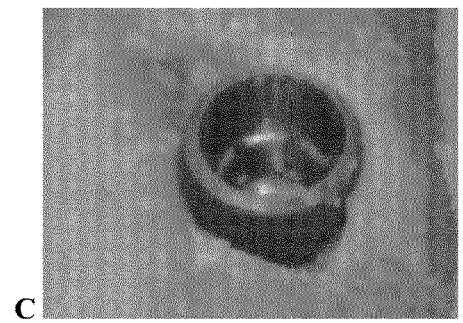
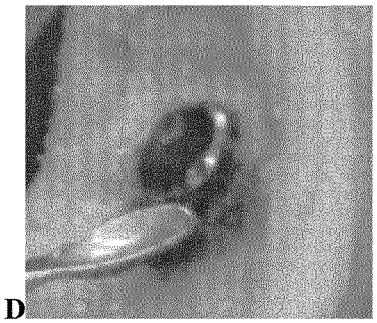
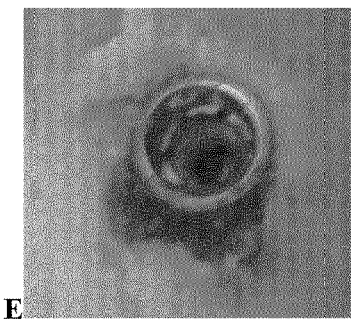
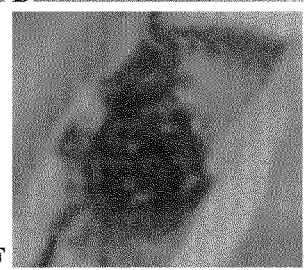
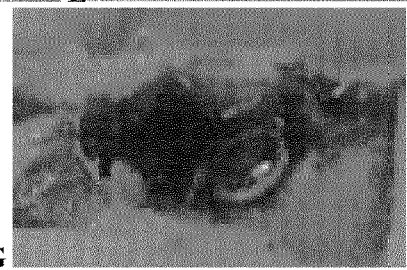

Fig. 9A
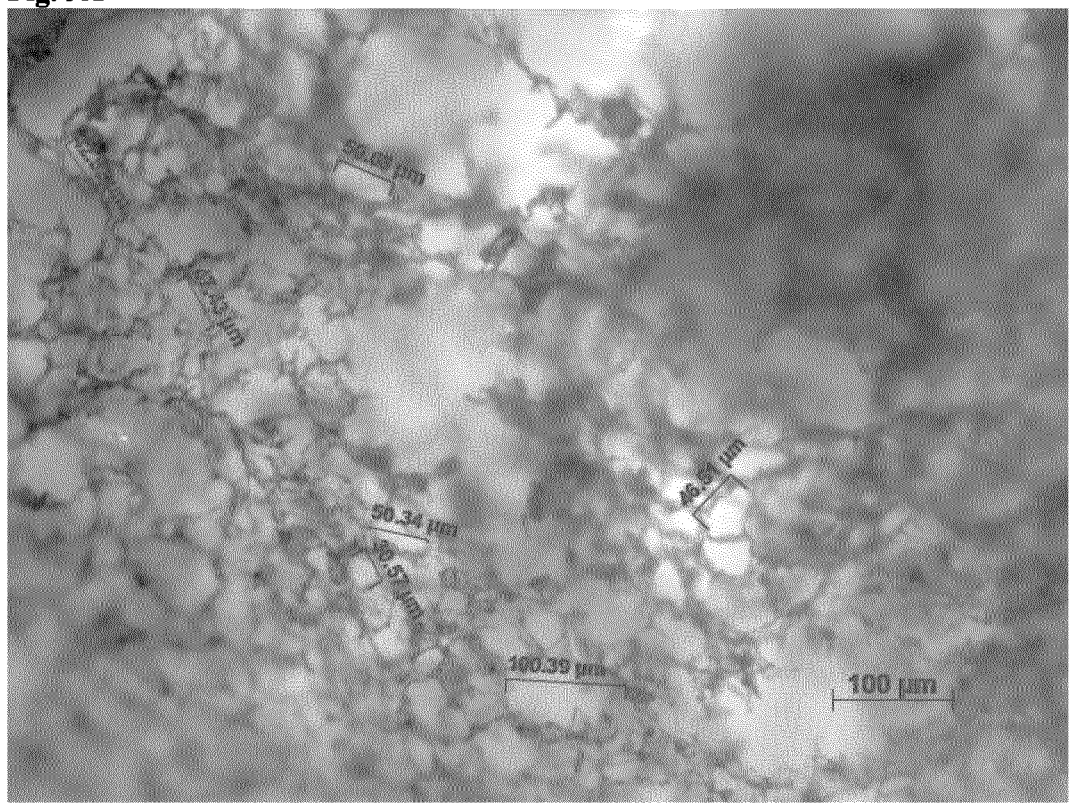
B
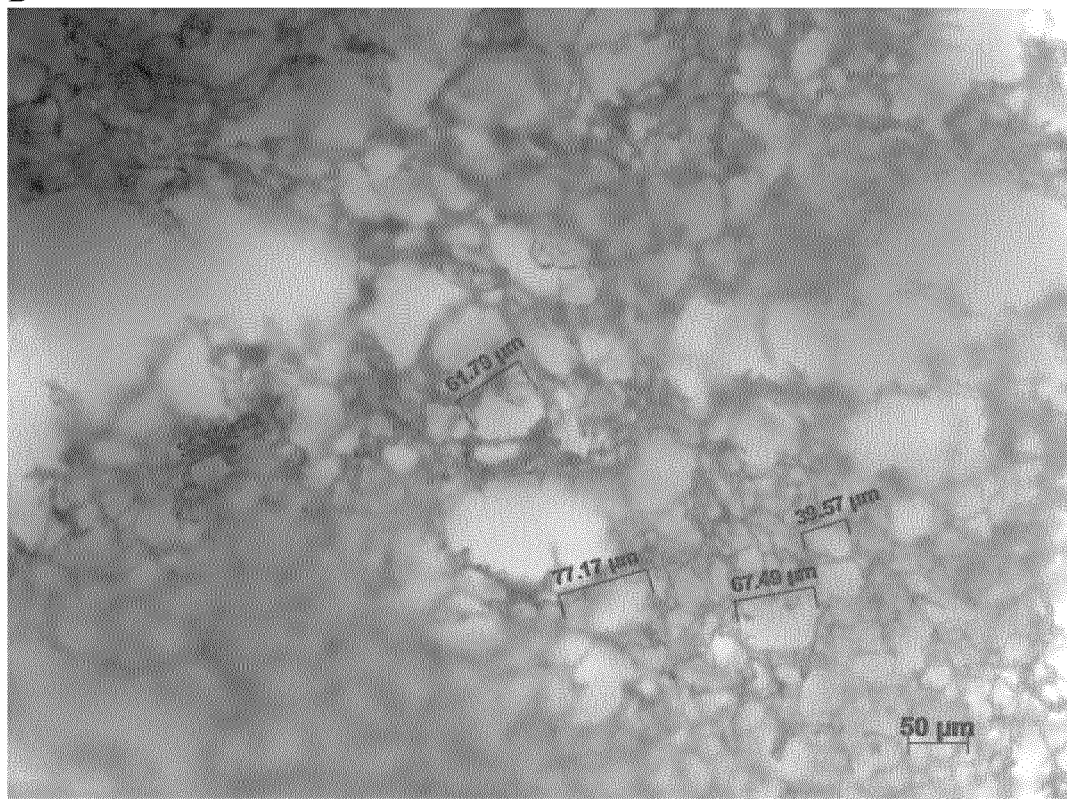

Fig. 10A
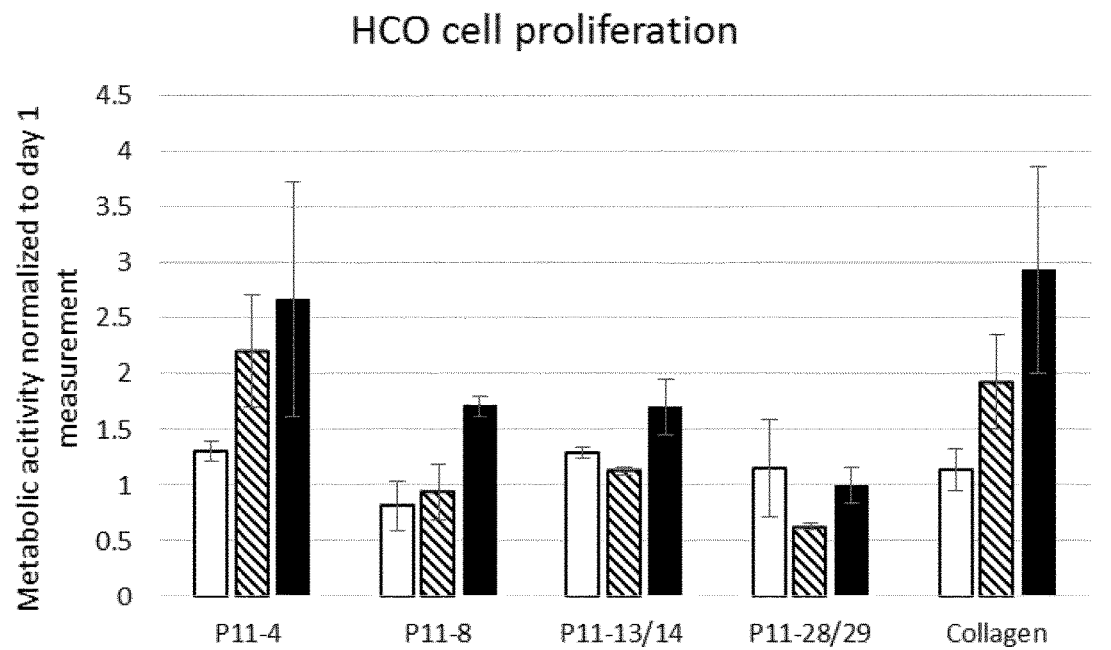
B
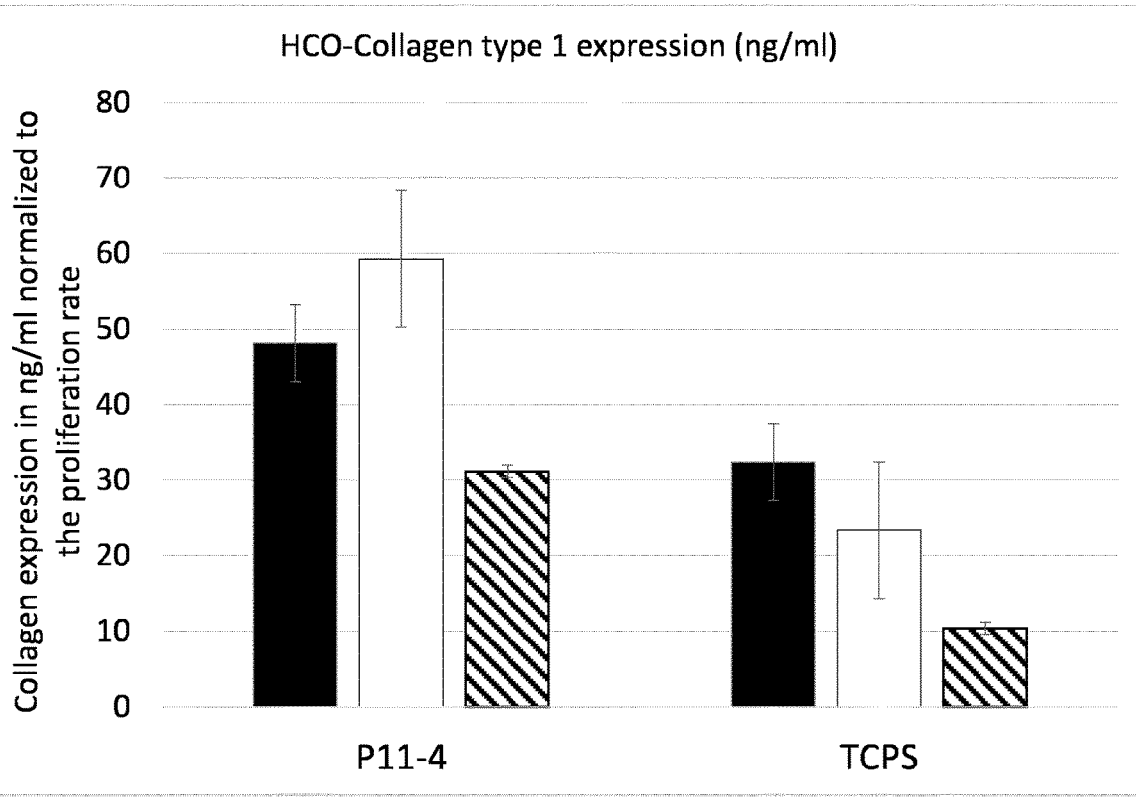

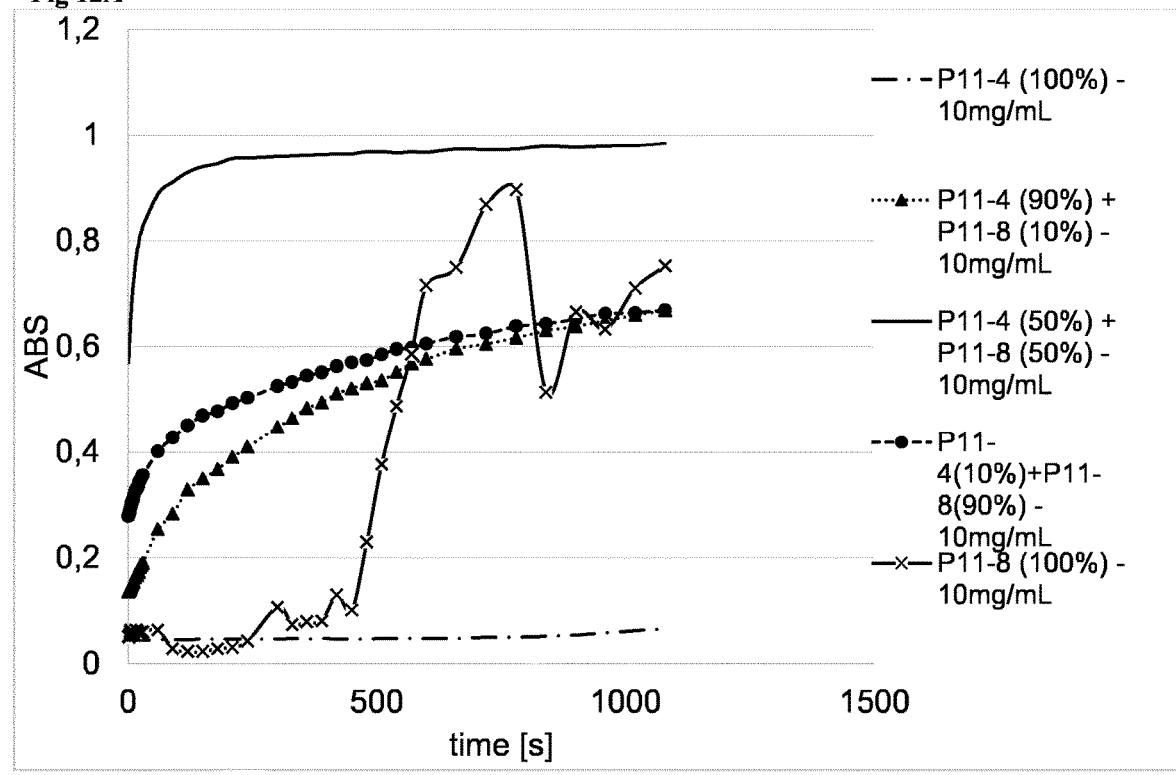
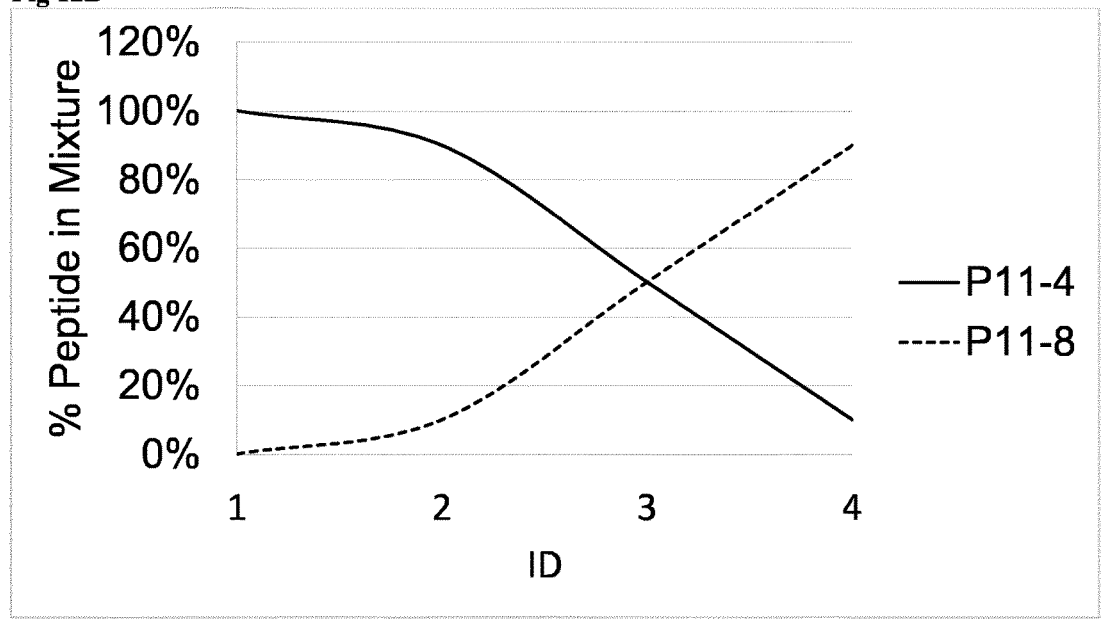

Fig. 13A
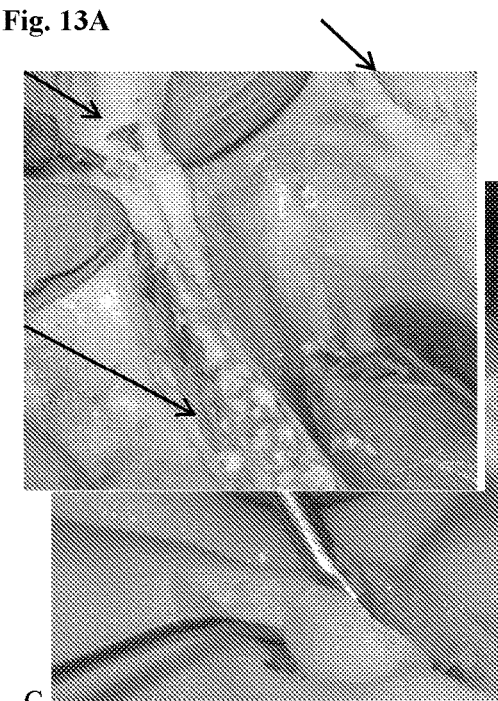
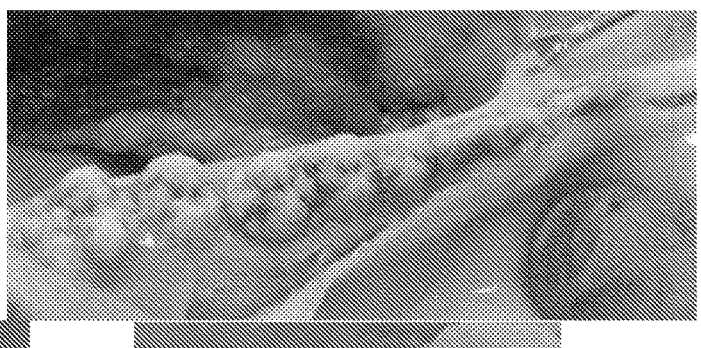
C    D
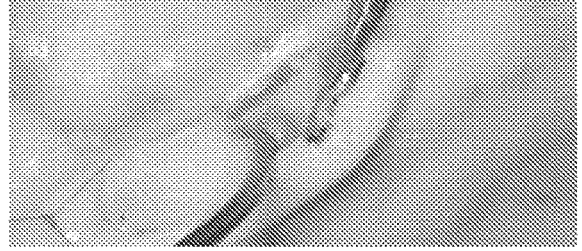
E    F
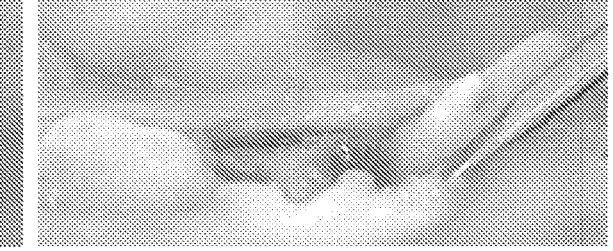
G    H
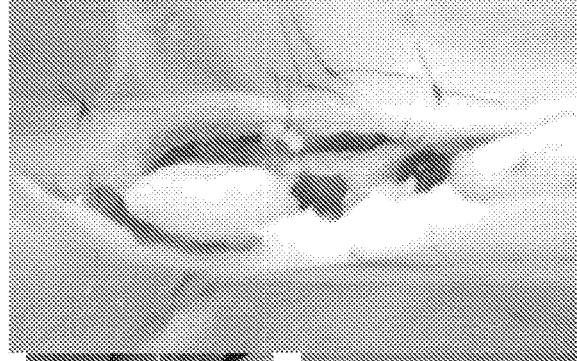
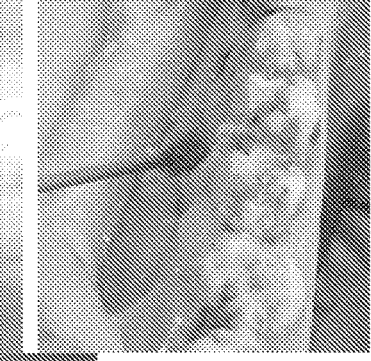
I    J

Fig. 14A
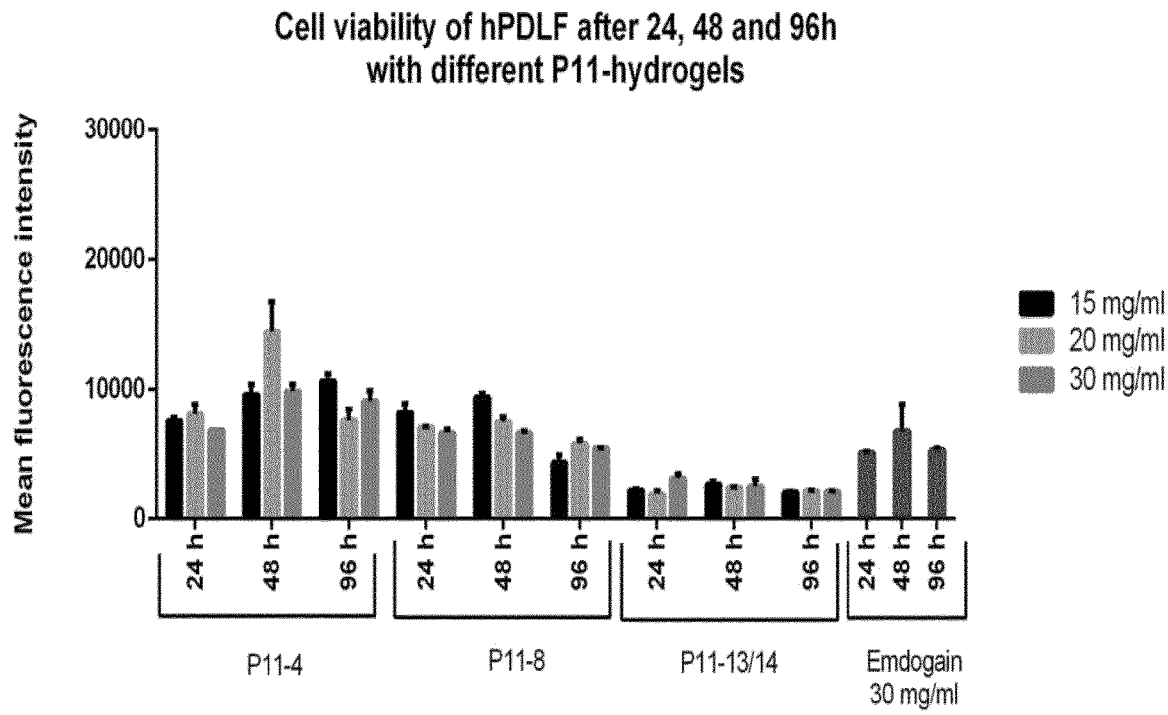
B
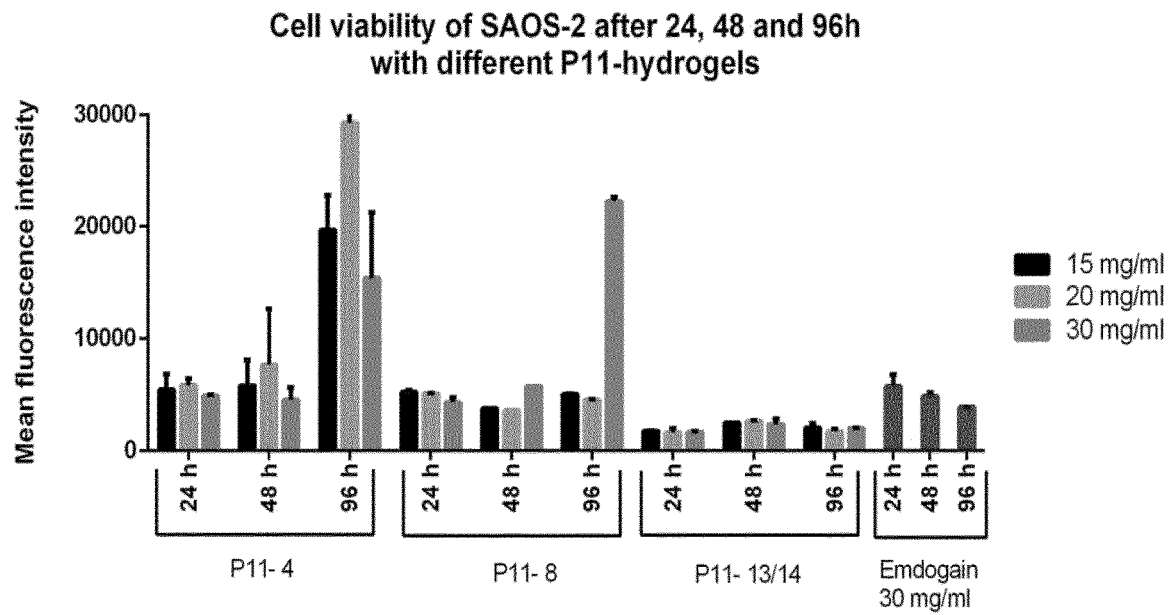

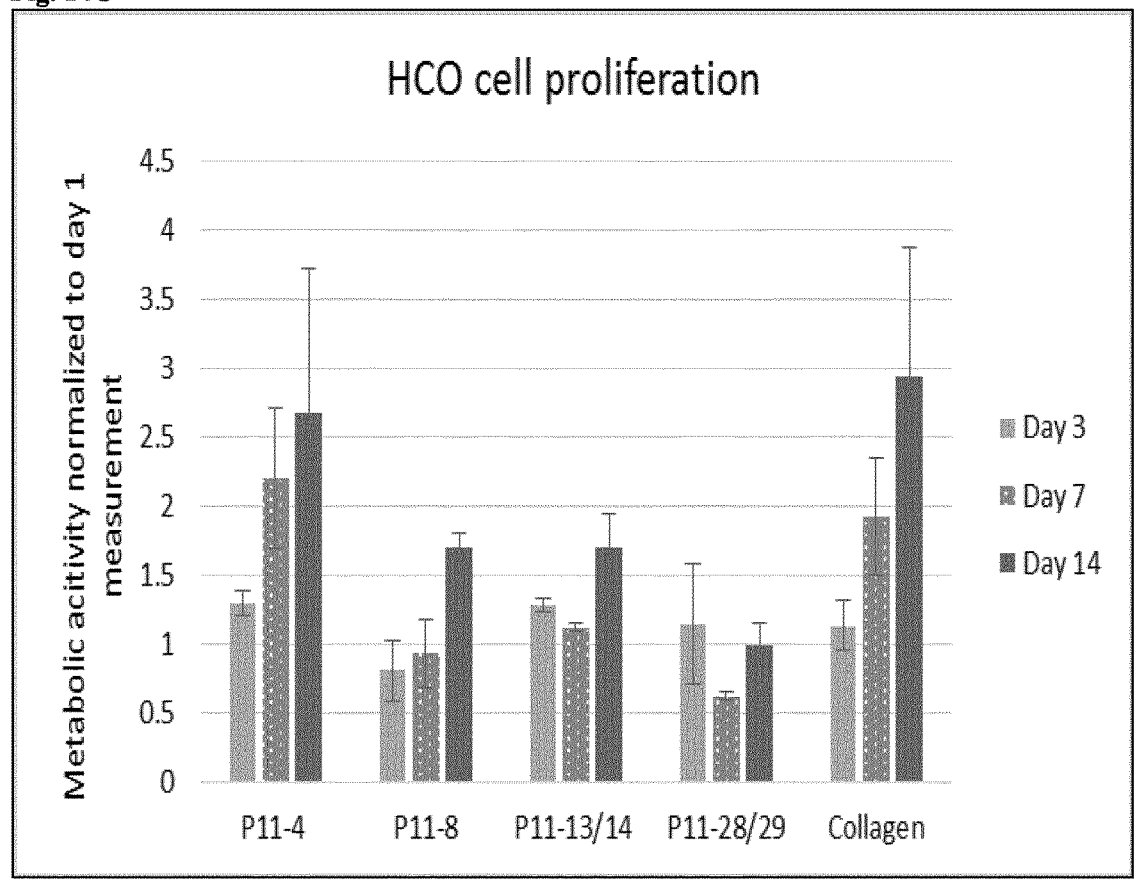
Fig. 14C
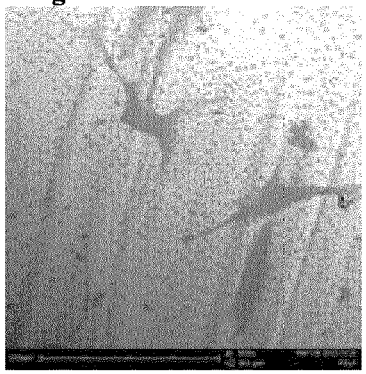
Fig. 15A
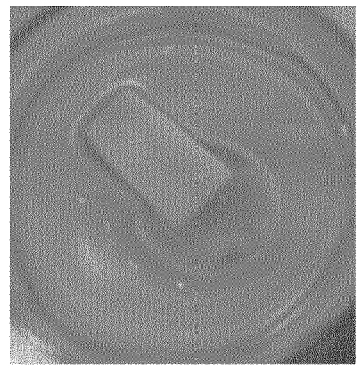
B
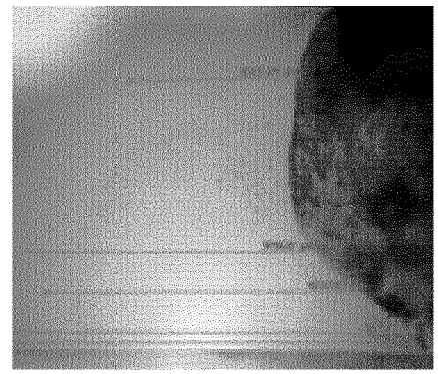
C

Fig. 15D
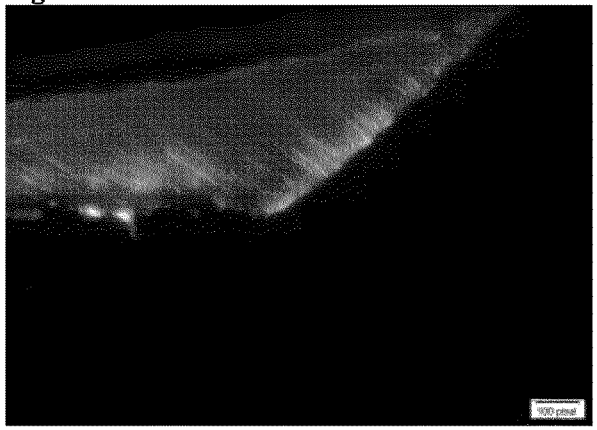
E
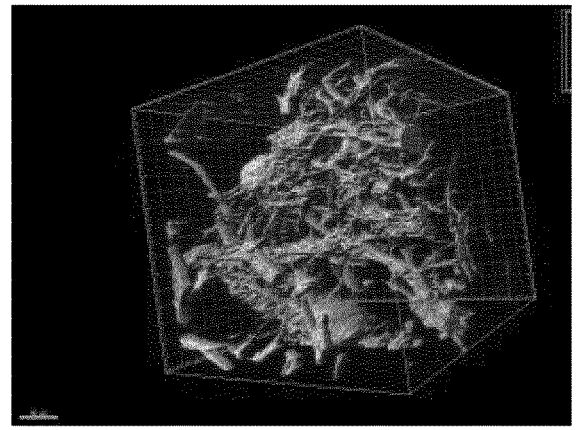
F
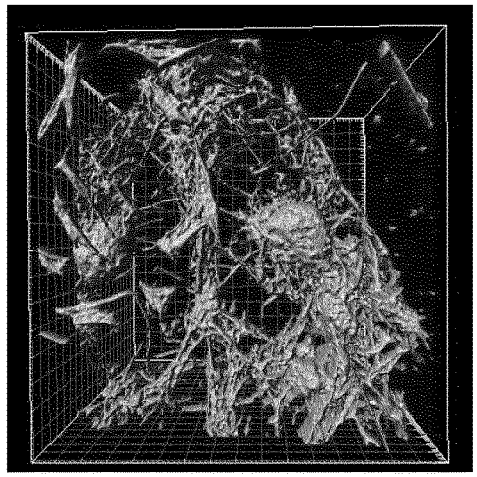
G
Fig. 16
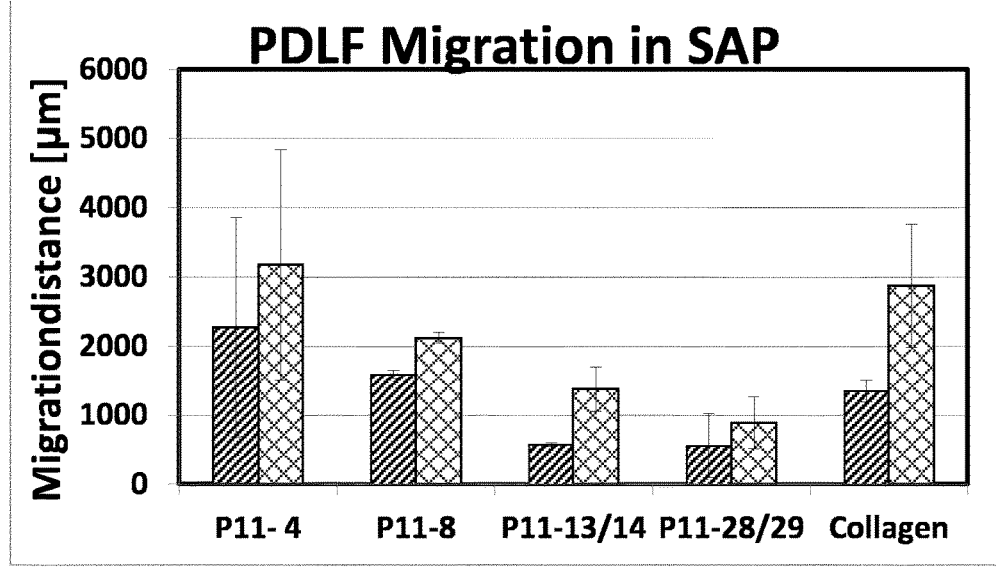

Fig. 19
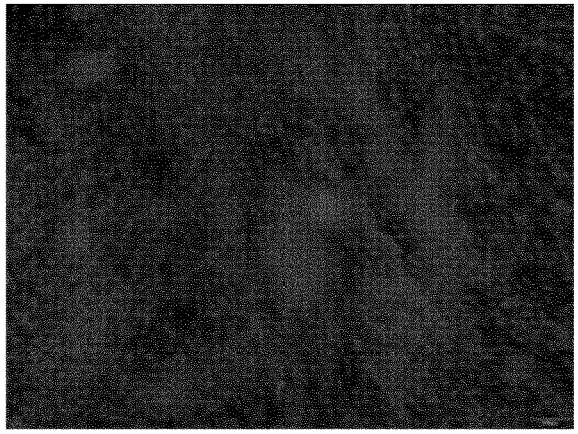
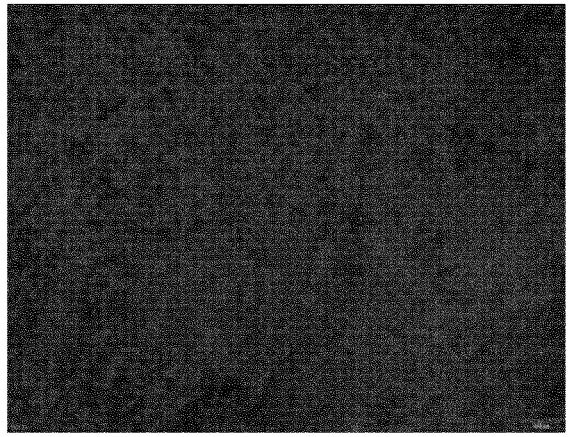
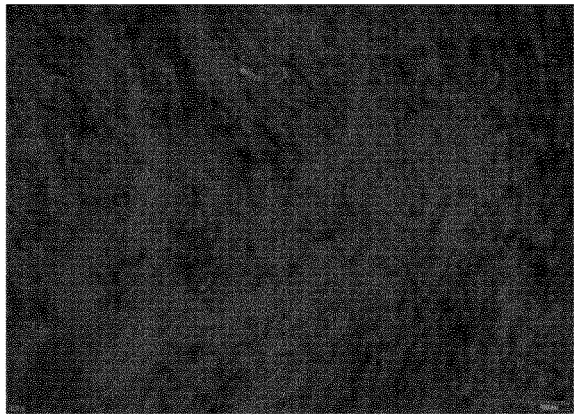
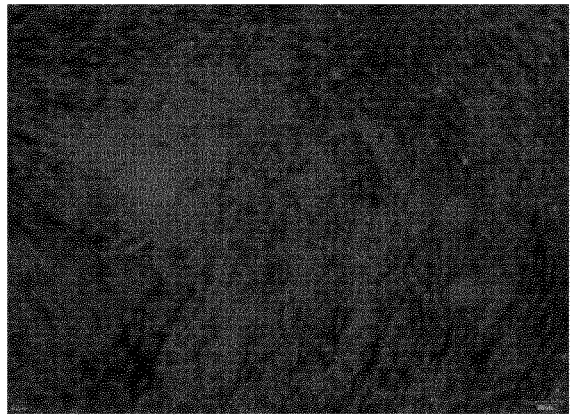
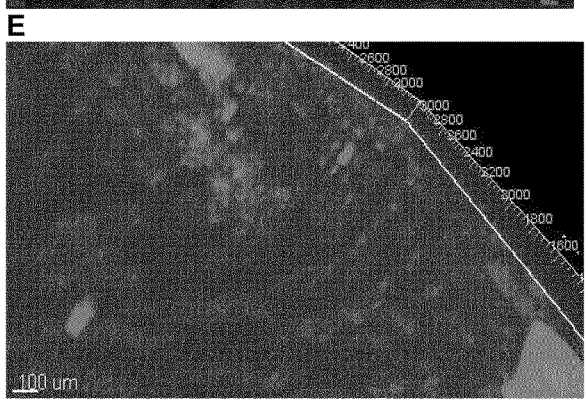

COMPOSITION COMPRISING SELF-ASSEMBLING PEPTIDES FOR USE IN TREATMENT OF GINGIVITIS, PERIODONTITIS AND/OR PERI-IMPLANTITIS

The present invention provides a composition comprising specific self-assembling peptides, which are capable of self-assembly at a pH below 7.5 and at least physiologic ionic strength, e.g., P11-4, P11-8, P11-14, P11-13, P11-12, P11-28, P11-29, P11-2, P11-5, P11-17, P11-19, P11-20, P11-12, P11-16, P11-18, P11-26 or P11-31, for use in treating an oral disease selected from the group consisting of gingivitis, periodontitis and/or peri-implantitis in a subject. Said composition may be used, after suitable cleaning procedures, for filling pockets formed adjacent to teeth in said diseases, which enhances tissue regeneration. The composition may be suitable for controlled release of an active agent, e.g., an antimicrobial or antibiotic agent. The invention also provides a kit suitable for said treatment further comprising self-assembling peptides suitable for forming a second layer on top of the first composition.

Gingivitis ("inflammation of the gum tissue") is a non-destructive periodontal disease. The most common form of gingivitis, and the most common form of periodontal disease overall, is in response to bacterial biofilms (also called plaque) adherent to tooth surfaces, termed plaque-induced gingivitis. Gingivitis is reversible with good oral hygiene.

However, in the absence of treatment, or if not controlled, gingivitis can progress to periodontitis. Periodontitis—or periodontal disease—is a set of inflammatory diseases affecting the periodontium, i.e., the tissues that surround and support the teeth. Periodontitis is caused by microorganisms that adhere to and grow on the tooth's surfaces, along with an over-aggressive immune response against these microorganisms. With the destruction of the gingival fibers, the gum tissues separate from the tooth, leading to deepened sulcus, called a periodontal pocket. Subgingival micro-organisms, i.e., those that exist apically from gum line, colonize the periodontal pockets and cause further inflammation in the gum tissues and progressive bone loss. If left undisturbed, microbial plaque calcifies to form calculus, which is commonly called tartar. Tissue destruction, e.g., of periodontal ligament, and alveolar bone resorption can ultimately lead to tooth mobility and subsequent loss of involved teeth.

In the early stages, periodontitis has very few symptoms, and in many individuals the disease has progressed significantly before they seek treatment. A diagnosis of periodontitis is established by inspecting the soft gum tissues around the teeth with a probe (i.e., a clinical examination) and by evaluating the patient's X-ray films (i.e., a radiographic examination), to determine the amount of bone loss around the teeth.

Current treatment of periodontitis starts with improvement of individual dental hygiene. Calculus above and below the gum line must be removed completely by the dental hygienist or dentist to treat gingivitis and periodontitis. This nonsurgical cleaning below the gum line is called debridement.

Depending on the degree of disease progression, the treatment can vary from simple removal of the biofilm, scaling and root planning to more demanding techniques like surgical intervention with flap elevation and direct access to the attachment structures. The disadvantage of such a therapy is that a purely reparative healing is induced. Due to the higher proliferation rate of epidermal cells, a long junctional epithelium will cover the cementum-free root surface. Moreover, the collagen fibers from the gingival scar tissue were shown to be oriented parallel to the root surface without any functional alignment (Diedrich, Fritz et al. 2003).

Instead of a repair of the periodontal tissues, a complete regeneration of the tissue is aimed at. This ideally comprises:
- Formation of a short junctional epithelium (enabled by inhibition of epithelial cell growth)
- New acellular fiber cementum on the exposed root surface
- Development of new periodontal ligament with functional fiber orientation
- New alveolar bone extending to 2 mm below the cement-enamel junction (Diedrich et al., 2003)

In order to gain regenerated periodontal ligament tissue, the wound healing process can be therapeutically manipulated. Some of the techniques used in the state of the art are summarized in Table 1:

TABLE 1

| Materials for supporting periodontal regeneration | |
| --- | --- |
| Implementation of | Aims at |
| Bone transplants, bone substitutes | Osseoinduction, Osseoconduction |
| Membranes (resorbable and non-resorbable) (Sculean, Rathe et al. 2007) | Mechanical exclusion of cells disturbing the periodontal regeneration process (epithelial cells, gingival fibroblasts) |
| Growth factors (e.g. BMP-2, BMP-7, PDGF (Kaigler, Avila et al. 2011)) | Induction of tissue differentiation (Nevins, Kao et al. 2013) |
| Enamel matrix derivatives (Emdogain ®) | Stimulating regenerative effects in periodontal ligament (through adhesion, migration, proliferation of periodontal ligament fibroblasts (Hoang, Oates et al. 2000); and expression of TGF, IL-6 (Van der Pauw, Van den Bos et al. 2000), and in alveolar bone (through proliferation (Jiang, Safavi et al. 2001, Schwarz, Rothamel et al. 2004), differentiation (Miron, Caluseru et al. 2013), increase of alkaline phosphatase activity (Thangakumaran, Sudarsan et al. 2009) of/in osteoblasts and osteoblast progenitor cells. |
| Adhesion proteins | Modulating cellular adhesion |

Additionally, the disease is treated with local or systemic applied antibiotics.

Four basic elements are required for periodontal repair and regeneration: adequate blood supply and wound stability, a source of bone and ligament forming cells, a supporting scaffold or matrix, and growth factors to regulate cell migration, proliferation and matrix synthesis and angiogenesis for revascularization of the site (Kaigler, Avila et al. 2011)

Multiple synthetic peptides, among them, self-assembling peptides, already showed their ability to support tissue regeneration. The following Table 2 summarizes some of the most frequently used peptides for tissue engineering. A complete list has recently been published by Nune et al. (Nune, Kumaraswamy et al. 2013). Ravichandran et al., 2014, J. Mater. Chem. B 2:8466-8478 also describe applications of self-assembling peptides for tissue engineering.

to settle in the defect area, to differentiate and to build up the appropriate extracellular matrix. In another study, amelogenin-derived peptide 5 (ADP5), which was previously identified as a region within amelogenin that shared with a set of hydroxyapatite-binding peptides (HABPs) was investigated in respect of its potential to regenerate the periodontal ligament. Cementum-root stock blocks from acellular regions of the cementum were coated with the peptide solution and immersed with $Ca^{2+}$ and $PO_4^{3-}$. The peptide was shown to facilitate cell-free formation of a cementum-like hydroxyapatite mineral layer that, in turn, supported attachment of periodontal ligament cells in vitro (Gungormus, Oren et al. 2012). Although this approach accommodates for the microstructure of the tooth cementum, it doesn't contribute to the essential 3D microenvironment of

TABLE 2

| Name of synthetic hydrogel | Cell source for tissue regeneration | Reference |
|---|---|---|
| | SAPs for tissue regeneration (all tested in in vitro systems) | |
| RADA16-I | neural tissue (hNDPCs) | (Liedmann, Rolfs et al. 2012) |
| RADA16-4G-BMHP1 SAP | neural tissue (rat neurons) | (Cigognini, Satta et al. 2011) |
| RADA16-I | Mixed retinal tissue | (Ho, Fitzgerald et al. 2011) |
| Functionalized RADA16 | Adult mouse neural stem cells | (Gelain, Bottai et al. 2006) |
| Functionalized RADA 16 | Periodontal ligament fibroblasts | (Kumada and Zhang 2010) |
| RADA16-I | primary rat neurons | (Holmes, de Lacalle et al. 2000) |
| Functionalized RADA16 | human adipose stem cell | (Liu, Wang et al. 2013) |
| KLD-12 | Bovine chondrocytes | (Kisiday, Jin et al. 2002) |
| KLD-12 | Rabbit MSCs | (Sun and Zheng 2009) |
| dodecapeptide (KLDL)3 | Bovine chondrocytes and bovine bone marrow stromal cells | (Miller, Kopesky et al. 2011) |
| d-EAK16 | Transverse rabbit liver wound healing | (Luo, Wang et al. 2011) |
| IKVAV | Murine neural progenitor cells | (Silva, Czeisler et al. 2004) |
| IKVAV-PA | PC12 cells | (Wu, Zheng et al. 2006) |
| IKVAV | Mouse model of spinal cord injury | (Tysseling-Mattiace, Sahni et al. 2008) |
| IKVAV | Neurocytes of bone marrow stromal cells | (Wu, Zheng et al. 2010) |
| IKVAV | Angiogenesis | (Song, Zheng et al. 2010) |
| SAPNF | Rat pancreatic islets | (Yuan, Cong et al. 2008) |

This overview list supports the efficiency of synthetic designer peptides to serve as adequate substrates for the regeneration on multiple tissues. So far, only one peptide was investigated in respect to its capability to support regeneration of the periodontal ligament (Kumada and Zhang 2010). In order to enable cellular migration into the peptide hydrogel, pure self-assembling peptide scaffolds RADA16 were functionalized by direct coupling for short biologically active motifs. These motifs were a 2-unit RGD binding sequence and a laminin cell adhesion motif. Migration behavior was visualized by confocal imaging only. After incubation oft two weeks the peptide with the integrated RGD sequence promoted the migration of the periodontal significantly. Takeuchi et al. 2016 describe effects of RADA16 on healing of surgical periodontal effects in rats.

In other in vitro studies the cells or tissues were mixed directly with the peptide of interest or placed on top of the hydrogel. Both approaches do not reflect the physiological processes of tissue regeneration, where active migratory events are key issues for wound healing and finally to return to tissue homeostasis. In the case of the periodontal ligament, progenitor cells of the basal root have to be recruited the periodontal ligament and finally proves just the fact that periodontal ligament fibroblasts are able to attach to a hydroxyapatite surface.

Membranes are also used for treatment of periodontitis. In general, the membranes are made from animal derived collagen and aim to prevent the ingrowth of fibrous tissue into the intrabony defect.

Bone substitute materials may be used to act as a void filler if the bone is affected. Guided Tissue Regeneration is the method to regenerate the defect tissue (hard and soft tissue) of periodontal disease. There are three types available, either derived from animal or human sources or those made of synthetic hydroxyapatite/β-TCP.

Another standard is a resorbable, implantable material consisting of enamel matrix proteins, mainly amelogenin, derived from porcine juvenile jaws that are intended as an adjunct to periodontal surgery for topical application onto surgically exposed root surfaces.

All above mentioned techniques and materials have one shortcoming in general—they cannot be used to deliver local antibiotics to treat the infection more effectively (Tyagi, Vaish et al. 2011, Ahuja, Baiju et al. 2012). Currently, only the systemic administration of antibiotics or the local application of chlorhexidine solution or a chlorhexidine chip are alternatives.

Mucositis, a reversible inflammation of the tissue, can indicate the development of peri-implantitis. Peri-implantitis is a non-reversible, destructive inflammatory process (mixed anaerobic infection) affecting the hard tissues surrounding dental implants (Mombelli et al., 2011). It requires chirurgical intervention of the dentist to be regenerated.

The array of periodontal pathogens found around failing implants (those affected by peri-implantitis) are similar to those found in association with various forms of periodontal disease, but may have also other bacterias e.g. *Staphylococcus* spp., Enterobacteria and *Candida* spp present (Leonardt et al., 1999).

It could be shown that on rough implant surfaces significantly more plaque is formed than on smooth surfaces. Peri-implantary mucositis is a reversible inflammation of the mucosa around the implant. In contrast, peri-implantitis is characterized by an additional progressive inflammation of the alveolar bone around the implant. Peri-implantitis can lead to loss of the implant.

In the past, dental implants have been introduced in about 1% of the Swiss population, with a strong tendency of growth. The prevalence of peri-implantitis is estimated to be about 10 to 29%, or 20% of all subjects having an implant.

Treatment may include removing necrotized or inflamed tissue, removing of debris, use of antibiotics, and improvement of individual dental hygiene. This may include the use of antiinfectious and/or antimicrobial mouthwashes, e.g., washing with chlorhexidine-based solutions.

In addition, local or systemic antibiotic therapy is often recommended, typically a combination of metronidazol and amoxicillin, with the aim of reducing or elimination periopathogenic bacteria such as Aggregatibacter *Actinomycetemcomitans, Porphyromonas gingivalis, Prevotella intermedia, Tannerella forsythia* and *Treponema denticola*. Tetracycline (e.g., 0.2%), doxycycline (e.g. 5%), azithromycin (e.g., 0.5%) may also be used.

Local treatments may comprise of the application of a PerioChip® (Dexcel Pharma GmbH) comprising of 2.5 mg chlorhexidine, which is continuously released over the course of seven days. Similarly, Ligosan® (Heraeus-Kulzer) is a gel leading to slow release of doxycycline.

Not only bacterial decontamination, but also regeneration of new bone substance is decisive for successful therapy. Without new formation of bone structures, no healthy new soft tissue structures can develop, e.g., interdental papillae or the buccal gingival margin, which is important to prevent reintroduction of bacteria. Current Guided Tissue Regeneration like use of autogeneic bone transplants and different membranes (e.g., PTFE, collagen) are combined with a surgical approach. However, use of such membranes can also lead to bacterial penetration and reinfection (Prathapachandran et al., 2012).

In light of the state of the art, the present inventors aim to solve the problem of providing an improved product for treatment of gingivitis, periodontitis and/or peri-implantitis, which allows for easier application and effective treatment of said diseases.

This problem is solved by the present invention, in particular, by the subject matter of the claims. The present invention provides a composition comprising self-assembling peptides (SAP) comprising a sequence of SEQ ID NO: 1, wherein the self-assembling peptides are capable of self-assembly at a pH below 7.5 and at least physiologic ionic strength, for use in treating an oral disease selected from the group consisting of gingivitis, periodontitis and/or peri-implantitis in a subject.

Self-assembling peptides capable of self-assembly at a pH below 7.5 and at least physiologic ionic strength may start undergoing self-assembly at said pH, as is, e.g., the case for a preferred peptide, P11-4, but that is not required. They can also be capable of being in a self-assembled state at a higher or lower pH.

The skilled person will know how to determine and measure the ionic strength of a solution. The ionic strength I is generally calculated according to the formula $I=\frac{1}{2}\Sigma z_i^2 b_i$, wherein z is the valence factor and $b_i$ is the molality [mol/kg{$H_2O$}] of the $i^{th}$ ion concentration. The summation, $\Sigma$, is taken over all ions in a solution. For example, the ionic strength of a 150 mM NaCl solution is approximately 0.15 mol/L. This is also approximately the ionic strength of blood. The ionic strength of saliva present in the oral cavity, is generally much lower, such as approximately 0.04 mol/L. In the context of the invention, ionic strength in the physiological range is considered to be corresponding to a ionic strength of 0.15 mol/L.

If desired, the mechanical properties can be influenced by the concentration of the SAP and additionally the type of molecules and ions present in the composition (see FIG. 5 and legend to FIG. 5). A composition of the invention may e.g., comprises NaCl and, optionally, a biologically suitable buffer such as Tris. The composition may comprise any of the buffers used in the Examples below.

Self-assembling peptides of the invention are peptides that are capable of forming three-dimensional scaffolds, thereby promoting tissue regeneration. These, and related artificial peptides of the invention assemble in one dimension to form beta-sheet, and higher order assemblies such as tape-like assemblies. Three-dimensional supramolecular structures of self-assembling proteins can be formed, which have an affinity for/to calcium phosphate.

In the context of the present invention, self-assembling peptides may be able to self-assemble by themselves, as is the case, e.g., for the peptides P11-4, P11-8, P11-2, P11-5 mentioned below, but they can alternatively be able to self-assemble in a combination of two self-assembling peptides, as is the case, e.g., for the peptides P11-13/P11-14 and P11-28/P11-29, P11-30/P11-31 mentioned below.

Self-assembling peptides of the invention comprise the consensus sequence SEQ ID NO: 1, X1-X2-X1-X2-X1, wherein X1 is independently selected from the group consisting of glutamic acid, aspartic acid, glutamine and ornithine, and X2 is independently selected from the group consisting of alanine, valine, isoleucine, leucine, methionine, phenylalanine, tyrosine, tryptophan and glutamine. Independently selected means that, e.g., X1 in positions 1, 3 or 5 of the sequence above can be different from each other. Of course, they can also be identical.

Preferably, self-assembling peptides of the invention also comprise SEQ ID NO: 2, X1-X2-X1-X2-X1, wherein X1 is independently selected from the group consisting of glutamic acid and ornithine, and X2 is independently selected from the group consisting of tryptophan and phenylalanine.

Self-assembling peptides of the invention may further comprise SEQ ID NO: 3, X3-F-X1-W-X1-F-X1, wherein X1 is independently selected from the group consisting of glutamic acid and ornithine, and X3 is selected from the group consisting of arginine, glutamic acid and ornithine, wherein X3 preferably is arginine.

Self-assembling peptides of the invention may comprise SEQ ID NO: 4 or, preferably, consist thereof: X4-X4-X3-

F-X1-W-X1-F-X1-X4-X4, wherein X1 is independently selected from the group consisting of glutamic acid and ornithine, and wherein X3 is selected from the group consisting of arginine, glutamic acid and ornithine, and wherein X4 is independently selected from the group consisting of glutamine, glutamic acid, serine, threonine and ornithine. X3 preferably is arginine. Independently, X4 preferably is glutamine.

Self-assembling peptides of the invention may comprise SEQ ID NO: 5, or, preferably, consist thereof: Q-Q-R—F-X1-W-X1-F-X1-Q-Q, wherein X1 is independently selected from the group consisting of glutamic acid and ornithine.

In the context of the present invention, self-assembling peptides taught in WO 2004/007532 A1, U.S. Ser. No. 10/521,628, U.S. Ser. No. 12/729,046, U.S. Ser. No. 13/551,878, U.S. Ser. No. 14/062,768, or WO2014/027012 A1, which are all fully incorporated herein by reference, are preferred. Most preferably, said peptides comprise the specific peptides listed in Table 4 or consist thereof. Of course, self-assembling peptides assembling in combination with another self-assembling peptide, e.g., as disclosed above, may be formulated in one kit or in one composition.

Peptides of SEQ ID NO: 6, 9, 11, 12, 16 or 17 are particularly advantageous, e.g., as they can be used in relatively low concentrations, they are highly compatible with cells and have beneficial charge distribution.

Preferably, the self-assembling peptide comprises the sequence of SEQ ID NO: 6 or consists thereof. A peptide consisting of a sequence of SEQ ID NO: 6 is also designated P11-4, and is preferred throughout the invention. In another preferred embodiment, the self-assembling peptide comprises the sequence of SEQ ID NO: 9 or consists thereof (P11-8).

The composition of the invention may also comprise at least one self-assembling peptide having at least 45% sequence identity to a peptide consisting of SEQ ID NO: 6. Preferably, the peptide has at least 54%, at least 63%, at least 72%, at least 81% or at least 90% sequence identity to a peptide consisting of SEQ ID NO: 6, or is said peptide. Peptides of the invention may be 11 amino acids in length.

Self-assembling peptides may be modified peptides comprising an Ac-N-terminus and/or $NH_2$—C-Terminus, preferably, both, or non-modified peptides. As non-blocked forms tend to start a deaminization reaction, the termini of all self-assembling peptides of SEQ ID NO: 1 are preferably blocked to increase stability. In particular, peptides of SEQ ID NO: 6, 9, 11, 12, 16 and 17 may comprise an Ac-N-terminus and $NH_2$—C-Terminus. SEQ ID NO: 18-29 correspond to modified peptides of the invention.

TABLE 3

| Consensus sequences of preferred self-assembling peptides | | | |
|---|---|---|---|
| SEQ ID NO | Peptide name | Sequence | Exemplary SAP |
| SEQ ID NO: 1 | Consensus sequence 1 | X1-X2-X1-X2-X1, wherein X1 is independently selected from the group consisting of glutamic acid, aspartic acid, glutamine and ornithine, and X2 is independently selected from the group consisting of alanine, valine, isoleucine, leucine, methionine, phenylalanine, tyrosine, tryptophan and glutamine | P11-2, P11-4, P11-5, P11-8, P11-12, P11-13, P11-14, P11-17, P11-19, P11-20, P11-28, P11-29 |
| SEQ ID NO: 2 | Consensus sequence 2 | X1-X2-X1-X2-X1, wherein X1 is independently selected from the group consisting of glutamic acid and ornithine, and X2 is independently selected from the group consisting of tryptophan and phenylalanine | P11-4, P11-8, P11-12, P11-13, P11-14, P11-17, P11-28, P11-29 |
| SEQ ID NO: 3 | Consensus sequence 3 | X3-F-X1-W-X1-F-X1, wherein X1 is independently selected from the group consisting of glutamic acid and ornithine, and X3 is selected from the group consisting of arginine, glutamic acid and ornithine, wherein X3 preferably is arginine | P11-4, P11-8, P11-12, P11-13, P11-14, P11-17, P11-28, P11-29 |
| SEQ ID NO: 4 | Consensus sequence 4 | X4-X4-X3-F-X1-W-X1-F-X1-X4-X4, wherein X1 is independently selected from the group consisting of glutamic acid and ornithine, and wherein X3 is selected from the group consisting of arginine, glutamic acid and ornithine, and wherein X4 is independently selected from the group consisting of glutamine, glutamic acid, | P11-4, P11-8, P11-12, P11-13, P11-14, P11-17, P11-28, P11-29 |

TABLE 3-continued

Consensus sequences of preferred self-assembling peptides

| SEQ ID NO | Peptide name | Sequence | Exemplary SAP |
|---|---|---|---|
| SEQ ID NO: 5 | Consensus sequence 5 | serine, threonine and ornithine. X3 preferably is arginine. Independently, X4 preferably is glutamine. Q-Q-R-F-X1-W-X1-F-X1-Q-Q, wherein X1 is independently selected from the group consisting of glutamic acid and ornithine. | P11-4, P11-8 |

TABLE 4

Preferred self-assembling peptides. Positions X1 are underlined

| SEQ ID NO | Peptide name | Sequence (One letter code) | % amino acid identity to P11-4 (ClustalW (2.1, standard parameters)) |
|---|---|---|---|
| SEQ ID NO: 6 | P11-4 | QQRFEWEFEQQ | 100 |
| SEQ ID NO: 7 | P11-2 | QQRFOWOFEQQ | 81.8 |
| SEQ ID NO: 8 | P11-5 | QQRFOWOFQQQ | 72.7 |
| SEQ ID NO: 9 | P11-8 | QQRFOWOFEQQ | 81.8 |
| SEQ ID NO: 10 | P11-12 | SSRFOWOFESS | 45.4 |
| SEQ ID NO: 11 | P11-13 | EQEFEWEFEQE | 72.7 |
| SEQ ID NO: 12 | P11-14 | QQOFOWOFOQQ | 63.6 |
| SEQ ID NO: 13 | P11-17 | TTRFEWEFETT | 63.6 |
| SEQ ID NO: 14 | P11-19 | QQRQOQOQEQQ | 54.5 |
| SEQ ID NO: 15 | P11-20 | QQRQEQEQEQQ | 72.7 |
| SEQ ID NO: 16 | P11-28 | OQOFOWOFOQO | 45.4 |
| SEQ ID NO: 17 | P11-29 | QQEFEWEFEQQ | 90.9 |
| SEQ ID NO: 30 | P11-16 | NNRFOWOFENN | 45.4 |
| SEQ ID NO: 31 | P11-18 | TTRFOWOFETT | 45.4 |
| SEQ ID NO: 32 | P11-26 | QQOQOQOQOQQ | 36.4 |
| SEQ ID NO: 33 | P11-31 | SSOFOWOFOSS | 27.3 |

The self-assembling peptides preferably do not have restriction sites for the subject's endopeptidases. They also do not need to comprise a special recognition motif for cells.

The inventors could surprisingly show that self-assembling peptides contribute to both soft and hard (bone) tissue regeneration of the periodontal gap or the implant gap after periodontal or peri-implantitis treatment, wherein the self-assembling peptides will act as guiding matrix for the tissue growth. They also prevent premature overgrowth by epithelial cells.

The present invention also provides a method for treatment of gingivitis, periodontitis and/or peri-implantitis in a subject in need thereof, comprising administering an effective amount of self-assembling peptides comprising a sequence having SEQ ID NO: 1, wherein the self-assembling peptides are capable of self-assembly at a pH below 7.5 and at least physiologic ionic strength, to said subject as further explained below.

The composition may be for use in treating gingivitis, wherein regeneration of soft tissues affected by gingivitis is improved by administration of the composition of the invention to the sulcus pockets.

The composition may be for use in treating periodontitis. In this context, the composition preferably comprises an antibiotic or is co-administered with an antibiotic. The antibiotic may be a peptide. In some embodiments, the composition does not comprise a non-peptide antibiotic.

The composition may be for use in treating peri-implantitis. In this context, the composition preferably comprises an antimicrobial agent such as an antibiotic or, e.g., taurolidine, or is co-administered with such an agent. The antibiotic may be a peptide. In some embodiments, the composition does not comprise a non-peptide antibiotic.

The disease which is to be treated is preferably associated with the formation of pockets adjacent to at least one tooth or implant, wherein the gum and/or the bone have receded, in particular the bone. Treatment is particularly advantageous at a stage where both gum and bone have receded.

In one embodiment of the invention, in the composition, at least 70%, preferably at least 80%, more preferably at least 90% of the self-assembling peptides are present in a monomeric state. To this end, the pH of the composition may be above the pH wherein the peptide starts to undergo self-assembly (e.g., pH 7.5 for P11-4), preferably, 0.1 to 0.5 pH units above said pH, or more than 0.5 pH units above said pH.

The pH may be buffered at that pH to avoid quick aggregation. It may be beneficial if aggregation, and formation of a hydrogel starts quickly after application in the pocket. Accordingly, the pH may be 0.1 to 0.5 pH units above the pH at which the peptide starts to undergo self-assembly, without buffering. In one embodiment, the composition may comprise lyophilized peptide, e.g., prepared according to WO 2014/027012.

If the self-assembling peptide in the composition is monomeric or essentially monomeric as described herein, after insertion of the composition into the pocket, a hydrogel forms by self-assembly of the peptides and, preferably, inclusion of body liquids. This contributes to an environment favorable to tissue regeneration, e.g., with nutrients and/or signalling molecules for guidance of cells. Such body liquids may be, e.g., blood, gingival crevicular fluid (also designated sulcular fluid), or a mixture thereof. Saliva may also be incorporated, typically in low amounts. Of note, there is no gingival crevicular fluid in peri-implantitis.

Alternatively, liquids co-administered with the SAP may be incorporated in a hydrogel, e.g., blood from the subject.

For application of monomeric self-assembling peptide compositions, different application forms may be used. For example, a two-component syringe may be used.

A composition comprising monomeric SAP is filled into a two component syringe, in one compartment the SAP, and in a second compartment a solution triggering the assembly in situ. The composition comprising the SAP, or the filled syringe may be freeze dried. The dental practitioner may apply the content of the syringe directly into the pocket.

During application, the solvent and freeze dried SAP may be mixed mainly in the periodontal pocket and will assemble in situ either due to the used solvent or the acidic conditions predominating in the periodontal pocket (e.g., in a two-component syringe manufactured by Artocorp, Japan).

Alternatively, during application, the solvent and freeze dried SAP are mixed in a mixing chamber of the two-component syringe and will assemble in situ either due to the used solvent or the conditions predominately in the periodontal pocket. (e.g., in a two-component syringe manufactured by Sulzer, Mixpac cartridge system).

If the self-assembling peptides assemble as combinations of two peptides, e.g., P11-13 and P11-14 or P11-28 and P11-29, respectively, solutions of the single peptides can packaged separately and the respective combination mixed before administration, e.g., manually or in a two-compartment syringe. If applicable, an API (active pharmaceutical ingredient, in particular, an antimicrobial agent such as an antibiotic agent) may be included with either of the two components (or both) in the composition before use.

To obtain a quick assembly, the concentration of SAP obtained after mixing of the two components may be, e.g., 10 mg/mL or more, optionally, 20 mg/mL or more, 40 mg/ml or more, or 60 mg/ml or more, in particular, 20-60 mg/ml.

To increase structural stability, additional gel forming agents, preferably, with a non-animal origin, e.g., cellulose or derivatives thereof such as hydroxymethylcellulose, may be comprised in the composition.

In another embodiment, the composition comprises self-assembling peptides in assembled form, e.g., at least 70%, preferably at least 80%, more preferably at least 90% in assembled form, or essentially assembled form, and a liquid selected from the group comprising a buffer (at a pH stabilizing the assembled form) and the subject's blood and a mixture thereof. Said compositions typically form a hydrogel.

A dental practitioner may apply the gel directly from a syringe with a canula into the pocket or pockets or around dental implants.

Such compositions can e.g., be prepared by dissolving the SAP in a buffer A wherein the SAP is predominantly monomeric, adding a buffer B and mixing, which leads to assembly of the SAP. The composition may be included in a syringe which allows for application into the periodontal pocket and reduces the time of waiting until the formed hydrogel is stable. Optionally, one or more conserving agent may be added and/or dark syringes may be used to increase storage stability of the gel. Optionally, the composition can be applied after root cleaning and planning in a periodontal surgery.

Such compositions may comprise, e.g., 20 mg/mL or more self-assembling peptide. Stability and hydrogel administration to experimental periodontal defects were tested. Compositions comprising 20 mg/mL P11-4 could be rendered sufficiently stable by lowering the pH, e.g., by addition of HCl. Compositions comprising 40 mg/mL or 60 mg/mL were easier to apply and more stable in the pocket (FIG. 8A). Accordingly, it is preferably to use compositions comprising about 30 mg/mL-70 mg/mL, preferably, about 40 mg/mL-60 mg/mL SAP (e.g., P11-4).

In one embodiment, monomeric SAP and assembled SAP are administered into the periodontal pocket. For example, a two component application system, e.g., a dual component syringe may be used, one chamber comprising monomeric peptide, and the other, assembled peptide. The concentration of assembled peptide may be, e.g., 5-20 mg/ml, preferably 10-15 mg/mL. The concentration of monomeric peptide may be the same or higher, e.g., 10-60 mg/mL, preferably, 20-50 mg/mL. The mixture of assembled SAP, e.g., in fibril form, and monomeric peptide is mixed in situ. This application form leads to an increased viscosity, increased stability of the gel formed in the defect and increased bonding to the adjacent surfaces.

Combinations of different self-assembling peptides may also be used. For example, P11-4, providing excellent cellular compatibility, may be combined with P11-8 as follows (% relate to wt/wt %):

TABLE 5

|     | P11-4 | P11-8 |
| --- | --- | --- |
| # 1 | 100% | 0% |
| # 2 | 90% | 10% |
| # 3 | 50% | 50% |
| # 4 | 10% | 90% |

Combinations of complimentary self-assembling peptides, e.g., of P11-4 and P11-8, provide a significant faster assembly time resulting in a faster application due to their attraction to each other. This is also shown in FIG. 12.

For example, a mixture of 2 ml 10 mg*ml-1 P11-4 (monomeric) in a 50 mM Tris Buffer, pH 8 mixed with 2 ml of a 10 mg*ml-1 P11-8 (monomeric) in 50 mM TRIS, 0.192 M NaCl pH 6 results in a significant faster assembly time of 5 min compared to pure peptide assembly times.

It is possible to add a cellulose-derivate to the self-assembling peptides for preparation of a chip. For this, the composition is filled in defined cavities, air dried, resulting in a hard and stiff chip, which may be directly applied into the pocket.

It is also possible to prepare a sponge composition of the invent ion by drying, e.g., freeze drying a hydrogel formed by assembled self-assembling peptides and, optionally, one or more bulking agents (e.g. trehalose or mannitol), e.g., by freeze drying a hydrogel formed by assembled self-assembling peptides and bulking agents. Depending on the conditions, either small pores or big pores can be achieved and closed porous outer surface can be designed, resulting in different release and resorption properties. The dentist may apply the sponge directly on the bone structure after root scaling/planning. Then, the tissue may be closed, e.g., as known in the art using a protective membrane, or preferably, with a second layer of self-assembling peptide. A suture may also or alternatively be applied.

A dried (e.g., freeze dried) sponge obtainable by drying a hydrogel formed by assembled self-assembling peptides may also be designated an aerogel or aerogel composition.

The inventors found that dried (e.g., dried by lyophilization (i.e., freeze dried), or dried by critical point drying) aerogels or sponges comprising SAP can be advantageously formed from solutions having a concentration of about 20-60 mg/mL SAP (e.g., P11-4), preferably, 30-60 mg/mL or 40-60 mg/mL. Preparation of corresponding aerogels is described in the experimental section. Application of a 40 mg/mL P11-4 aerogel on a defect is shown in FIG. 8B. Freeze-dried aerogels can also be prepared as disclosed in Scanlon et al., 2007, i.e., by quick immersion in liquid nitrogen for 2 min, followed by lyophilisation in a freeze-dryer (e.g. Heto, Drywinner) overnight at room temperature.

Accordingly, the invention provides an aerogel comprising a SAP of the invention, comprising a self-assembling peptide comprising the consensus sequence according to SEQ ID NO: 2, SEQ ID NO: 3, SEQ ID NO: 4 and/or SEQ ID NO: 5, wherein the self-assembling peptides are capable of self-assembly at a pH below 7.5 and at least physiologic ionic strength of the invention, e.g., P11-4 or P11-8, preferably, P11-4, which is useful for the pharmaceutical applications disclosed herein. Such an aerogel optionally comprises an active agent as disclosed herein.

A solid SAP composition, e.g., the chip or, preferably, the sponge as described above, may be rehydrated by liquids derived from the body, e.g., blood or exsudated liquid. No waiting time for formation of a stable gel is required, so the defect (the periodontal pocket) may be closed, e.g., by a suture, using a protective membrane and/or a second layer of SAP, directly after application.

In one embodiment, alternatively, a solution comprising SAP may be added to a solid SAP composition for rehydration and optimal filling of the pocket. Said solution comprising SAP may be assembled SAP, e.g., at a concentration of 5-20 mg/mL or 8-10 mg/ml and/or monomeric SAP, e.g., at 10-50 mg/mL. A kit is provided comprising a solid SAP composition such as a dried (e.g., lyophilized) sponge (also designated aerogel) and solutions comprising assembled and monomeric SAP, respectively, e.g., in separate compartments in a dual chamber syringe. An alternative kit may comprise a solid SAP composition, such as a dried aerogel, and a dual chamber syringe comprising, in separate compartments, monomeric self-assembling peptide, e.g., in dried form, and a buffer capable of leading to assembly of the self-assembling peptide. After mixing of the two components, additional SAP fibrils and fibres are formed which enhance filling out the periodontal pocket. The kit may comprise (i) an aerogel composition comprising self-assembling peptides comprising a sequence of SEQ ID NO: 2, wherein the self-assembling peptides are capable of self-assembly at a pH below 7.5 and at least physiologic ionic strength of the invention, and
(ii) at least one composition comprising the same self-assembling peptides as the aerogel, wherein
   a) at least 70% of the self-assembling peptides are present in the composition in a monomeric state and/or
   b) the composition is a hydrogel comprising self-assembling peptides in assembled form and a liquid, Such kits may be for use in treating gingivitis, periodontitis and/or peri-implantitis in a subject, preferably, periodontitis or peri-implantitis. If the kit is for use in treating peri-implantitis, the composition further comprises an antibiotic agent.

A solid SAP composition, e.g., the aerogel or sponge as described above, may have a standard size of about 6-10 mm×6-10 mm, e.g. 7-8 mm×7-8 mm or 8 mm×8 mm with 2-5 mm thickness. It can easily be applied into the periodontal pocket and sticks to the surface thereof.

Advantageously, a SAP composition of the invention, in particular, a solid SAP composition of the invention, e.g., the dried (e.g., freeze-dried) sponge as described above, may comprise a pharmaceutically acceptable colouring agent (e.g., a drug colorant such as Carmine, Caramel, Annato extract etc) and/or agent leading to radio-opaque characteristics (e.g. barium sulfate). Colour simplifies application for the dental practitioner. Radio-opaque characteristics simplify monitoring of healing and resorption of the SAP composition.

The composition (e.g., dry powder or gel) may be sterilized, either sterilized by e-beam or by gamma irradiation, or ingredients may be aseptic filtered prior use.

The total concentration of self-assembling peptides may be 0.05-100% (w peptide/w bulk product), e.g., 0.1-80%, 0.2-40%, 0.5-20%, or 1-10%.

Preferably, 0.1-1 ml of a composition of the invention, e.g., 0.2-0.5 ml may be administered within the pocket adjacent to one tooth or implant or within the defect site, the composition having a concentration of self-assembling peptides such as described above, e.g., about 10% (or 10 mg/ml).

Optionally, the composition of the invention may comprise a crosslinking agent, such as transglutaminase, a homobifunctional, amine-reactive, NHS-ester crosslinker such as Sulfo-DSS, DTSSP, Sulfo-EGS, DSG, DSP, DSS, EGS, a heterobifunctional, NHS-ester/diazirine crosslinker, such as Sulfo-SDA, Sulfo-LC, SDA, Sulfo-SDAD, SDA, LC-SDA, SDAD, a photoreactive crosslinker, such as riboflavin, or glutaraldehyde, formaldehyde or a reducing sugar. The composition may also be crosslinked by UV irradiation, in combination with one of the crosslinking agents above which may be activated by UV irradiation, or without such a crosslinker, after application within the pocket or defect site. Crosslinking is possible both with compositions applied in monomeric form and with compositions applied in assembled state.

Crosslinkers with an increased activity at the surface, e.g., photosensitive crosslinkers activated by UV irradiation, lead to formation of a protective more dense or rigid structure at the surface of the composition, thus reducing the invasion of cells and/or bacteria from the oral cavity into the pocket or defect site.

In all embodiments of the invention, the composition may comprises an active agent, in particular, an antimicrobial agent such as taurolidine or an antibiotic, or an antiseptic agent, e.g., chlorhexidine. An antibiotic useful for treatment of periodontitis or peri-implantitis, may be, e.g., doxycycline (e.g., at a dose of 20 mg/pocket). In this case, in particular when antibiotics are used, the disease preferably is periodontitis or peri-implantitis, as antibiotic treatment is typically not required for gingivitis. For peri-implantitis antibiotic treatment is always indicated, but it may be local or systemic. Preferably, an antibiotic is part of the composition of the invention, or a kit of the invention, and is incorporated in the hydrogel formed by the self-assembling peptide.

Active agents comprise antibiotics such as tetracycline (e.g., at about 0.2%), doxycycline (e.g., at about 5%), azithromycin (e.g., at about 0.5%), minocycline; and/or antiseptic agents such as chlorhexidine.

The composition may also or alternatively comprise an anti-inflammatory agent, in particular, an non-steroidal anti-inflammatory drug (NSAID) such as a salicylate (e.g., acetylsalicylic acid), propionic acid derivative (e.g., ibuprofen, naproxen), acetic acid derivative, enolic acid derivative, anthranilic acid derivative or sulfonanilide, or a selective COX-2 inhibitor, and/or a herbal extract (e.g., chamomile extract and/or clove extract).

In the context of the present invention, unless expressly indicated otherwise, "a" means "one or more", i.e., "an antibiotic" includes combinations of two (or more) antibiotics.

Due to incorporation in the hydrogel formed by the self-assembling peptide, a slow delivery of the antibiotic or of another active agent is achieved. Preferably, the dose and delivery is adjusted so that a suitable concentration of the agent for suppressing bacterial growth and/or killing bacteria in the pocket is achieved. The active agent may be incorporated directly into the hydrogel when it is formed, diffused into the hydrogel after formation, wherein mechanical and diffusional resistance of the hydrogel lead to slow disease, or encapsulated for still more controlled delivery, wherein the encapsulated active agent is incorporated in the hydrogel. Suitable encapsulation material may be, e.g., gelatine, alginate or lipids. Preferably, the active agent is not chemically linked to the self-assembling peptide, although such embodiments are possible.

Preferably, the composition of the invention reduces the invasion of bacteria from the oral cavity into the pocket for at least 3 days. Preferably, for at least 5 days or at least 7 days, wherein the concentration of active antibiotic agent(s) is at least at the therapeutic level for at least said number of days. Surprisingly, it was found that the compositions of the invention are able to mediate controlled release of active agents, e.g. of antimicrobial agents, with an approximately constant rate (+/−20% per day) over a period of at least three days.

The invention also comprises a kit for use in treating gingivitis, periodontitis and/or peri-implantitis in a subject, wherein the kit comprises
(i) a first composition, which is the composition of any of the preceding claims, wherein the composition further comprises an antibiotic agent if it is for use in treating peri-implantitis, and
(ii) a second composition comprising self-assembling peptides, wherein the self-assembling peptides of the second composition are able to form a hydrogel having a higher gel density and higher gel rigidity than those of the first composition wherein the self-assembling peptides of the second composition are preferably a mixture of two complimentary peptides capable of forming a hydrogel together, and wherein the second composition is for use in forming a layer capable of reducing the invasion of cells and/or bacteria from the oral cavity in the pocket.

The first and/or second composition may be comprised in syringes, e.g., two-component syringes as described herein.

Gel density and gel rigidity can, e.g., be measured according to methods known in the state of the art, e.g., rigidity can be measured as described by Cameron, 2001, In vitro Cellular & Developmental Biology—Plant 37:419). Preferably, density and/or rigidity, most preferably, both are more than 10%, more than 20%, more than 30% or more than 50% higher than the respective parameter for a hydrogel formed by the first composition.

The treatment for which the composition of the invention is employed may comprise
a) cleaning and/or debridement of at least one tooth or implant affected by the disease and
b) insertion of the composition into a pocket adjacent to said tooth or implant caused by gum and/or bone recession caused by the oral disease.

Step a) may be preceded by surgical opening, in particular, of deep pockets. In that case, as the last step of treatment, the surgical opening is closed. Alternatively, micro invasive techniques may be used, which avoid opening up pockets, but allow for cleaning and then application of the composition of the invention.

Step a) may be carried out, e.g., by methods known in the art, such as, root scaling, root planning or air-polishing.

In step b), the pocket may be filled as completely as possible to avoid leaving room for bacterial development. Preferably, a plurality of pockets, or all pockets of affected teeth or implants are treated.

Optionally, in step c), the composition in the pocket is covered by a layer capable of reducing the invasion of bacteria from the oral cavity into the pocket. Such a layer may e.g. be a membrane, such as a PDFE or collagen membrane known in the art. Alternatively, the layer may be a layer of self-assembling peptides, or a combination of two self-assembling peptides, forming a hydrogel having a higher rigidity and density than the first composition, as described for the second component of the kit herein.

For example, if the first peptide is P11-4, the second peptide may be P11-8 or a combination of P11-13 and P11-14 or of P11-28 and P11-29. If the first peptide is P11-8, the second peptide may be a combination of P11-13 and P11-14 or of P11-28 and P11-29. Alternatively, a gel composition of higher density and gel rigidity can be formed by using a higher concentration of self-assembling peptide, so that, e.g., the first composition may comprise P11-8 and the second composition may comprise P11-8 at 150-250%, e.g., 180-200% of the concentration in the first composition. For example, step b) may be carried out with 10 mg/ml P11-8, and step c) with 20 mg/ml P11-8.

The second layer, if it comprises complimentary SAP, may be administered by a two-component syringe, wherein the first compartment comprises one of the two SAP, and the second compartment comprises the second SAP. The SAP in the syringe may be lyophilised or non-lyophilised.

Depending on the syringe system used, as explained above, mixing may occur in a mixing chamber or mainly in the pocket. The second layer may also incorporate an active agent, e.g., an antibiotic as described herein.

In the pocket, the SAP will provide a matrix for regeneration the growth and development of the required tissue. Due to its slow resorption during tissue regrowth, it allows for regrowth of other tissues than the faster growing (not wanted) gingival soft tissue, in particular, for regeneration of alveolar bone and formation of ligaments.

Additionally, by providing the matrix for the regeneration, active agents which may be comprised in the hydrogel formed by the composition in the pocket will diffuse out slowly and treat the local bacterial inflammation effectively.

The periodontal ligament represents a complex tissue structure between the tooth cementum and the alveolar bone. The matrix is build up by periodontal ligament fibroblasts (PDLF) that produce their ECM, which mainly consists of collagen. During periodontitis this structure is severely affected. To test if self-assembling peptides such as P11-4 or P11-8 enable tissue regeneration, an in vitro human tissue model of the periodontal gap was developed. It allows for assessment of important process steps of tissue regeneration. In vitro investigations made the positive effect of self-assembling peptides for periodontal tissue regeneration apparent, in particular, they lead to proliferation of relevant cells, they facilitate migration of the cells and they increase extracellular matrix production by the cells.

The following figures and examples are supposed to illustrate and further explain, but not to limit the invention. Any references cited herein are herewith fully incorporated.

FIG. 1: Bacterial density after release of antibiotics (150 mg/ml) from self-assembling peptide gels (15 mg/ml), and the impact thereof to the growth of *P. gingivalis* (A-C) and

*S. sanguinis* (D-F). Circles: metronidazol, stars: tetracycline, triangle: ciprofloxacin, squares: doxycycline hyclate; control: gel without API A/D P11-4 gel. B/E P11-13/14 gel. C/F P11-28/29 gel FIG. 2: Cross section of demineralized tooth after incubation with polymeric P11-4. P11-4 has been covalent labelled with a Alexafluor® 647 a fluorescent dye resulting in white luminescence indicating the penetration of the polymeric P11-4 into the dentinal tubules, allowing for easy attachment of the fibres to the dentin.

FIG. 3: Stability of P11—Peptides over a period of 7 days in the absence of cells or bacteria. 100 μl peptide/well, c=20 mg/ml, in PBS, quantified with Qubit R Protein Assay Ref: Q33211. Complementary peptides such as P11-13/14 and P11-28/29 are more stable than P11-4 or P11-8, however, the resulting release of peptide into the supernatant with less than one ppm is considered as very low and the peptide therefore considered very stable.

FIG. 4: Degradation of P11-4 peptides over a period of 3 days in the presence of bacteria. 100 μl peptide/well, c=20 mg/ml, in PBS, quantified with Qubit R Protein Assay Ref: Q33211. The peptide is stable over more than 3 days, and stability is not significantly affected in the presence of bacteria, which is comparable to the release of the SAP into the supernatant as in FIG. 3.

FIG. 5: Mechanical properties are dependent on the presence of different ions and buffer systems. G' of a P11-4 (A) and P11-8 (B) gel formed in the presence of Tris-NaCl (140 mol/L, pH 7.5±0.5), artificial saliva (Tris (120 mM), Ca(NO$_3$) (4 mM), KH$_2$PO$_4$ (2.4 mM) with a final pH of 7.2, DMEM (Dulbecco's Modified Eagle Medium, pH 7.4, Gibco) and Tris MgSO$_4$ (140 mol/L, pH 7.5±0.5). DMEM medium consists of a final ionic strength of 130 mM with the main salt component NaCl (110 mol/L). Hence there are more monovalent ions (like Na$^+$, Cl$^-$) instead of divalent ions (like Mg$^{2+}$, Ca$^{2+}$, PO4$^{2-}$) present, Artifical saliva produced with the Strafford protocol, consists of a final ionic strength of 0.114 M ionic strength with a higher ratio of divalent ions (Ca$^{2+}$, (NO$_3$)–) towards monovalent ions (K$^+$, HPO4$^-$). Although final ionic strength of artificial is lower as 140 mM, storage moduli between G'(NaCl and MgSO$^4$) was reached, whereas for P11-8 lowest storage modulus was achieved with artificial saliva. Hence the divalent ion (Ca$^+$) has a positive effect on P11-4 self-assembling although the solution had a lower ionic strength. Since NO$_3$– are monovalent ions, and ionic strength of the solution was below 130 mM, P11-8 self-assembling was slowed down. On the other hand self-assembling kinetic of P11-8 with DMEM and NaCl solution is very similar. Whereas for P11-4, addition of DMEM resulted in hydrogels with lower storage modulus like for NaCl due to lower ionic strength with mainly monovalent ions.

FIG. 6: Cell migration of a 15 mg/ml P11-4 gel on a periodontal ligament model after 8 days of incubation. Human Periodontal Ligament cells were placed in a cell pool (A) and the SAP gel (C) placed on the human dentin (B). The cell/SAP-gel/dentin was then incubated for 8 days and visually assessed resulting in migration of up to 5 mm. Scale bar: 1 mm FIG. 7: Lyophilized P11-4 aerogels. A: 20 mg/mL, B: 40 mg/mL, C. 60 mg/mL. A-C: SEM at 2000×. D: from left to right: 60 mg/mL, 40 mg/mL, 20 mg/mL. It can be seen that the lyophilised aerogel for 20 mg/mL and 60 mg/mL is more dense than the 40 mg/mL aerogel.

FIG. 8: Application of P11-4 in a paradontitis model (pig, ex vivo). A: application of a 40 mg/mL assembled P11-4 gel into a periodontal pocket. B application of a lyophilized aerogel prepared from 40 mg/mL assembled P11-4 gel into a periodontal pocket. C: implants were placed into porcine jaw, and defects recapitulating a peri-implantitis defect were set. D, E: Patches of lyophilized P11-4 hydrogels at 20 and 40 mg/ml were placed in the furcation as well as peri-implantitis defect sites. F, G: They were mixed with human blood.

FIG. 9: Light microscopic (10×) analysis of pores in a 40 mg/mL P11-4 aerogel A: bottom right scale: 100 μm; B: bottom right scale 50 μm.

FIG. 10: SAP in an in vitro periodontitis model. FIG. 10A shows cell proliferation of human calvarial osteoblasts (HCO) after 3, 7 and 14 days incubation with SAP (15 mg/ml). Collagen (1.5 mg/ml) was used as a test system control. Cell proliferation was measured by the metabolic conversion of PrestoBlue viability reagent. Data were normalized in respect to values measured at day 1. white=day 3, lines=day 7, black=day 14. FIG. 10B shows collagen type 1 expression of HCO after 7, 14 and 21 days incubation with P11-4 (15 mg/ml). Cells grown on tissue culture plates (TCPS) were used as a control. Cell proliferation was measured by the metabolic conversion of PrestoBlue viability reagent. Data were normalized in respect to values measured at day 1. black=day 7, white=day 14, lines=day 21

FIG. 10C shows the migration distance of periodontal ligament fibroblasts (PDLF) out of the donor compartment after 4 (left column) and 8 (right column) days for dentin surfaces coated with different tested SAP and, as a positive control, collagen.

FIG. 11: Exemplary freeze-drying conditions for preparation of an aerogel. A: Table of parameters; B: Diagram.

FIG. 12: A shows data from static light scattering of different mixtures of P11-4 and P11-8 and their assembly time to a hydrogel. Interestingly, an equal ratio of P11-4 to P11-8 (10 mg*ml-1) leads to a significant faster gel formation than pure peptide and B the concentration gradient of different mixtures of self-assembling peptides assessed in FIG. 12a.

FIG. 13: Ex vivo application of P11-4 hydrogels on porcine jaw. A shows generation of defects in ex vivo porcine jaw. B shows a defect opened by MIST with the flap opened. C shows application of Emdogain® to a 2-wall defect (without Prep-Gel) with a bent needle, and D shows said defect closed by a suture. E and F show application of P11-4 gel (20 mg/ml, pH 7-8, 24 h pre-assembled) without (E) and with supplementation of Trypan blue 0.02% (F). G shows that the hydrogel was still stable at the defect site when the suture was reopened after 2 hours. H shows P11-4 gel (40 mg/ml, pH X7-8) applied to a defect with supplementation of Trypan blue. I shows a liquid drop of the hydrogel after shear thinning, and J shows recovery of hydrogel stability after a short time.

FIG. 14: Proliferation of cells on self-assembling peptides compared to Emdogain® and collagen A shows cell viability of hPDLF cells (human periodontal ligament fibroblasts), and B cell viability of SAOS-2 cells (Sarcoma osteogenic) after 24, 48 and 96 h with different P11-hydrogels (P11-4, P11-8, P11-13 and P11-14, compared with the current gold standard Emdogain®, respectively). Left column 15 mg/ml SAP, middle column: 20 mg/ml SAP, right column 30 mg/ml SAP for each SAP, for Emdogain®, the concentration is constant at 30 mg/ml, and the three columns show 24, 48 and 96 h administration. C shows cell proliferation of human calvarial osteoblasts (HCO) after 3, 7 and 14 days incubation with different SAP (15 mg/ml). Collagen (1.5 mg/ml) was used as a test system control. Cell proliferation was measured by the metabolic conversion of PrestoBlue viability reagent. Data were normalized in respect to values measured at day 1.

FIG. 15: A PDLF cells after 24 h attachment on pure bovine dentin surface. Cells adhere and proliferate on pure dentin surface. Cell attachment was visualized by SEM. B, C Periodontal model with dentin surface and cell donor compartment, as explained in Example L. Cell migration out of the donor compartment was determined by MTT staining of viable cells. D shows fluorescence labelled SAP (P11-4) interacting with the root matrix after 24 h contact. E and F show the migration of the PDLF in a SAP hydrogel (P11-4) through phalloidin actin staining. G shows fluorescence labelled P11-4 attached on the dentin surface and migrating into the dentin canals.

FIG. 16 shows migration distances of PDLF cells in different SAP (20 mg/ml-1 for P11,4 all other Peptides: 10 mg/ml) after 4 (left column, respectively) and 8 days (right column, respectively) and collagen (2 mg/ml) in the model periodontal pocket shown in FIGS. 15B and C.

Figure 18:
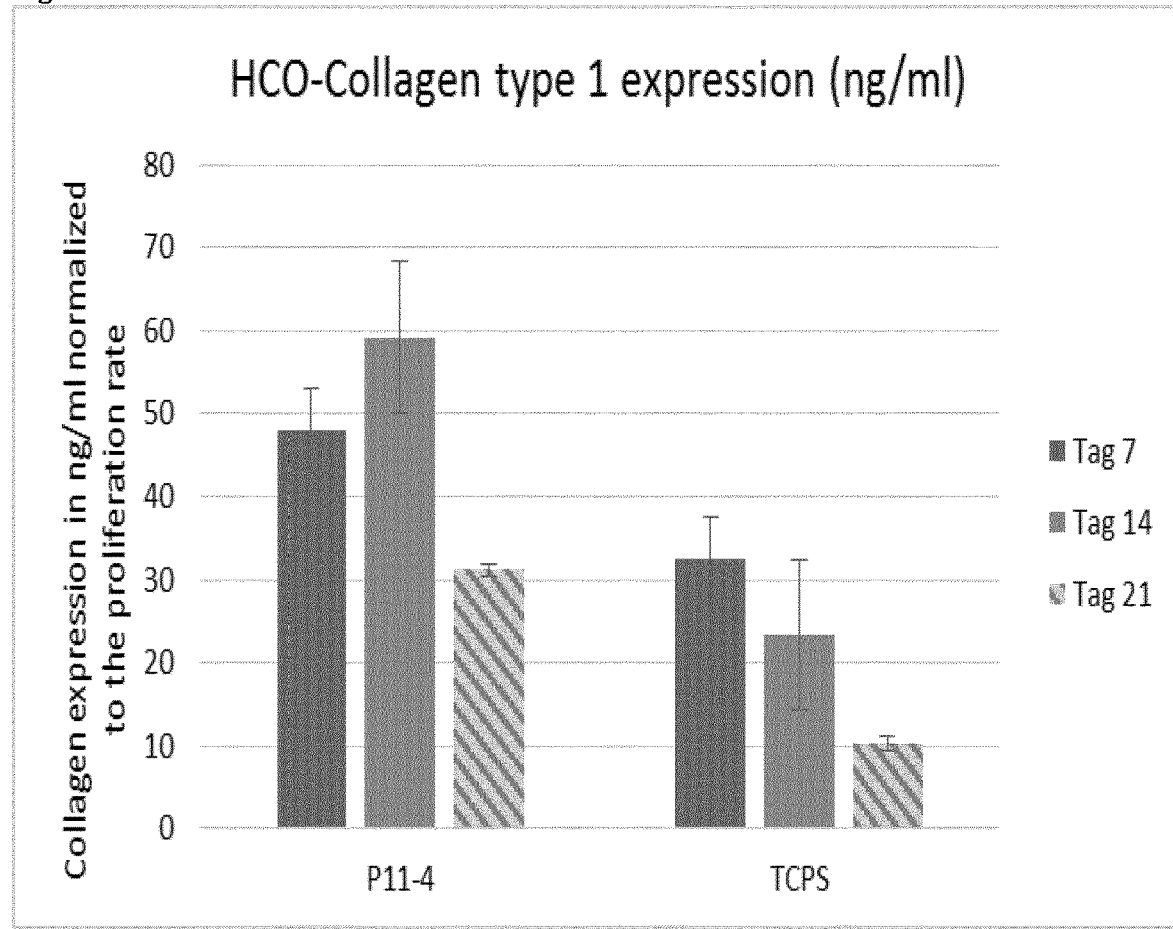

FIG. 18 shows induction of the expression of extracellular matrix, in particular, collagen type I, by HCO cells after 7 (left column, respectively), 14 (middle column, respectively) and 21 days' (right column, respectively) incubation with P11-4 (15 mg/ml). Cells grown on tissue culture plates (TCPS) were used as a control. Cell proliferation was measured by the metabolic conversion of PrestoBlue viability reagent. Data were normalized in respect to values measured at day 1. For each day, collagen expression was significantly greater with incubation with P11-4.

Figure 19:
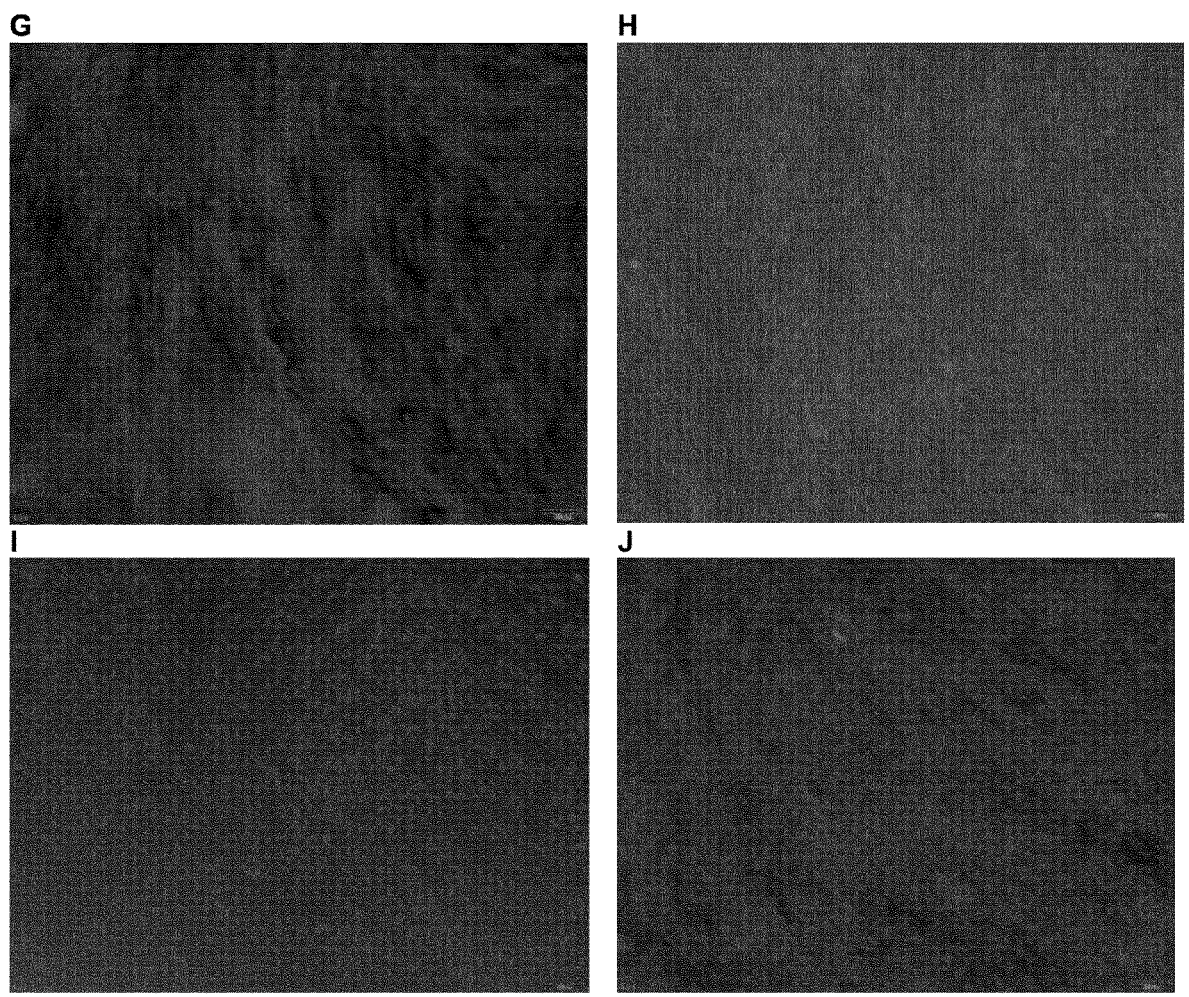

FIG. 19 shows staining of human periodontal ligament fibroblasts incubation with P11-4 (20 mg/ml) for 7 days for collagen type I (A, B), collagen type III (C, D), collagen type III, 3D Z stack 78 µm (E, F), Fibrilin I (G, H), and Fibrilin II (I, J). 10× magnification, primary antibody Anti-Fibrillin 1 antibody, secondary Antibody: Goat anti-Mouse IgG (H+L) Highly Cross-Adsorbed Secondary Antibody, Alexa Fluor 568.

Figure 20A:
Figure 20B:
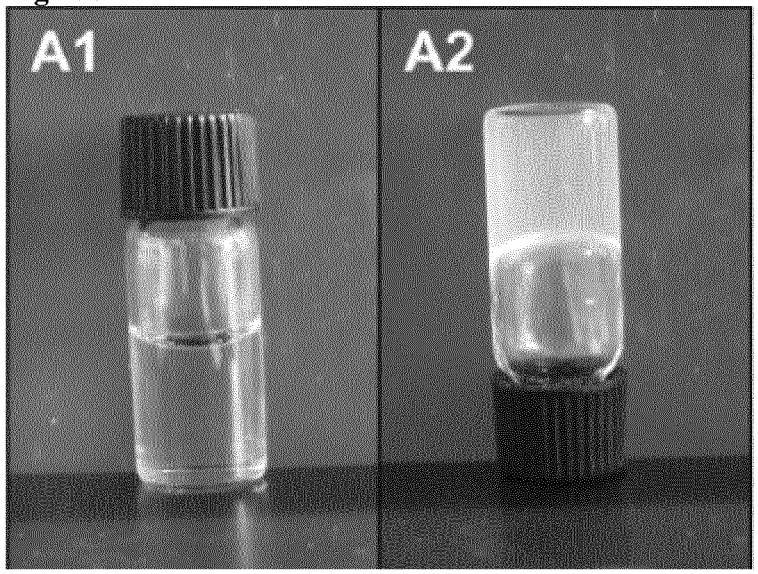

FIG. 20a shows a mixture of 1 part RADA16 solution (1 wt % peptide in water, Matrigel, Takeuchi et al., 2016) added to 1 part DMEM (Dulbecco's Modified Eagle's Medium) at neutral pH 7, as per manufacturers recommendation. No self-assembly is visible. FIG. 20b shows self-assembly of P11-4. A1: monomeric P11-4 (6.3 mM) at pH>8, appearing as a liquid; A2: P11-4 (6.3 mM) at pH 7, appearing as a nematic gel with high viscosity (from: Kind et al., 2017).

EXAMPLES

Example A—Monomeric Application Form

Prepare a 100 ml beaker glass, add 50 ml of water. Change pH with sodium hydroxide to pH 8 or 8.5. Add 1 g of self-assembling peptide P11-4 to the basic solution by slow addition under stirring. Wait for 5 minutes for fully dissolved material.

Check pH of solutions, pH should be kept by 8+/−0.4, if required correct it with either NaOH or Citric acid.

Sterile filter the solution into two-chamber sterile syringes. Fill the bulk into chamber 1, lyophilize the syringe and add pure, sterile water or sterile physiologic saline to chamber 2.

By pushing the plunger, the two components will mix and result in a basic extrusion product which will assemble in the pocket due to the lower pH and high ionic strength. After appropriate cleaning, e.g., scaling and debridement, the dental practitioner may inject the mixture into a pocket.

Alternatively, the final product can be sterilized by e-beam instead of sterile filtration.

Example B—Polymeric Application Form

Prepare a 100 ml beaker glass, add 50 ml of water. Change pH with sodium hydroxide to pH 8 or 8.5. Add 1 g of self-assembling peptide P11-4 to the basic solution by slow addition under stirring. Wait for 5 minutes for fully dissolved material.

Sterile Filter the Solution

Add sterile filtered citric acid, 0.1 M, in sterile environment to the solution under constant stirring until pH is set at 7.0.

Fill the solution into two-chamber sterile syringes. Fill the bulk into chamber 1, lyophilize the syringe and add saline solution to chamber 2.

By pushing the plunger, the two components will mix and result in an acidic extrusion product which may supply already assembled (polymeric) peptide to the treatment site. After appropriate cleaning, e.g., scaling and debridement, the dental practitioner may inject the mixture into or onto a pocket.

Alternatively, the final product can be sterilized by e-beam instead of sterile filtration.

Example C—Polymeric Application Form

Prepare a 100 ml beaker glass, add 50 ml of water. Change pH with sodium hydroxide to pH 8 or 8.5. Add 1 g of self-assembling peptide P11-4 to the basic solution by slow addition under stirring. Wait for 5 minutes for fully dissolved material.

Add citric acid, 0.1 M, to the solution under constant stirring until pH is set at 7.0.

Fill the gel into a one-chamber syringe. Irradiate syringe with e-beam at 20 kGy.

By pushing the plunger, the syringe will release a sterile gel to the treatment site. After appropriate scaling and debridement, the dental practitioner may inject the mixture into a periodontal pocket.

Alternatively, the final product can be sterilized by e-beam instead of sterile filtration.

Example D—Polymeric Application Form with Encapsulated Material

Prepare a 100 ml beaker glass, add 50 ml of water. Change pH with sodium hydroxide to pH 8 or 8.5. Add 1 g of self-assembling peptide P11-4 to the basic solution by slow addition under stirring. Wait for 5 minutes for fully dissolved material.

Prepare the desired antibiotic e.g. Doxycycline at 500 mg/l (Core material) in an agarose gel solution 2%. Drop the core material into a calcium chloride solution 5 g/l to form encapsulated Doxycycline.

Add citric acid, 0.1 M, to the solution under constant stirring until the pH is set at 7.0. Add the encapsulated antibiotic either prior, during or after the gel formation.

Fill the gel into a one-chamber syringe. Irradiate syringe with e-beam at 20 kGy.

By pushing the plunger, the syringe will release a sterile gel to the treatment site. After appropriate scaling and debridement, the dental practitioner may inject the mixture into a pocket, e.g., formed adjacent to an implant or a tooth affected by periodontitis.

Example E—Polymeric Application Form with Active Agent

Prepare a 100 ml beaker glass, add 50 ml of water. Change pH with sodium hydroxide to pH 8 or 8.5. Add 1 g of self-assembling peptide P11-4 to the basic solution by slow addition under stirring. Wait for 5 minutes for fully dissolved material.

Add the desired antibiotic e.g. Doxycycline at 500 mg/l into the clear solution.

Add citric acid, 0.1 M, to the solution under constant stirring until the pH is set at 7.0. Add the antibiotic either prior, during or after the gel formation.

Fill the gel into a one-chamber syringe. Irradiate syringe with e-beam at 20 kGy.

By pushing the plunger, the syringe will release a sterile gel to the treatment site. After appropriate cleaning, e.g., scaling and debridement, the dental practitioner may inject the mixture into a pocket, e.g., formed adjacent to an implant or a tooth affected by periodontitis.

Example F—Release of Antibiotics from Different Gels Formed by Self-Assembling Peptides Hydrogels comprising self-assembling peptides with (150 mg/ml) and without antibiotics were formed by dissolving the respective peptides at a concentration of 15 mg/ml or equimolar for combination SAP in a concentration of −10 mg*ml-1 as follows:

P11-4: A: 0.055 M Tris; pH 8.0 B: 0.055 M Tris; 0.192 M NaCl; pH 7.0
P11-8: A: H$_2$O B: 0.055 M Tris; 0.236 M NaCl; pH 9.0
P11-13/P11-29: 0.1 M Tris; 0.052 M NaCl; pH 8.0
P11-14/P11-28: 0.055 M Tris; 0.096 M NaCl; pH 7.2

It was tested if addition of the antibiotics to different buffers had an impact on the antibiotic effect (cf. FIG. 1A/B).

For the gels formed by peptides P11-13 and P11-14: or for P11-28 and P11-29, equimolar solutions of peptides were prepared in a well plate, and pH corrected to physiological conditions, resulting in a gel.

Furthermore 100 uL/well of a defined anaerobic *P. gingivalis* or aerobic *S. anguines* bacterial culture ($10^7$ CFU/ml e.g. 990 µl BHI medium, 10 µl $10^8$ CFU/ml bacteria suspension) were added onto the gels. Impact on growth was assessed by measuring turbidity at OD600 nm. Data obtained with antibiotics were normalized to control (gel+bacteria+medium without antibiotics) to analyse the relative bacterial density. 50 µl/well of medium were added every second day.

The experiment showed that except for metronidazole, which had low effectivity in most systems at this concentration, all antibiotics were stably released from the gel formed by the self-assembling peptides at a concentration sufficient to inhibit bacterial growth over 120 hours.

In general, there seems to be no significant difference of the impact depending on the selection of buffer to which the antibiotic is added.

A higher concentration of metronidazole should be used to inhibit bacterial growth, and this antibiotic seems to have best release rates from a P11-28 and P11-29 gel. It is thus preferred to use metronidazole in a concentration higher than 150 mg/ml, preferably, at least 500 mg/ml at least 1000 mg/ml or at least 2000 mg/ml, and, preferably, in combination with the self-assembling peptides P11-28 and P11-29.

Example G—Aerogels Comprising Lyophilized Self-Assembling Peptides

Hydrogels comprising self-assembling peptides were formed by dissolving the respective peptides at a concentration of the double target concentration in a buffer A wherein monomeric form is maintained. The same volume of a buffer B leading to self-assembly was added. Assembly took place for at least 24 h (at 4° C.).

Different compositions with the following target concentrations were tested:
20 mg/mL P11-4
40 mg/mL P11-4
60 mg/mL P11-4
Buffer A: 0.055 M Tris; pH 8.0 Buffer B: 0.055 M Tris; 0.192 M NaCl; pH 7.0

Figure 11:
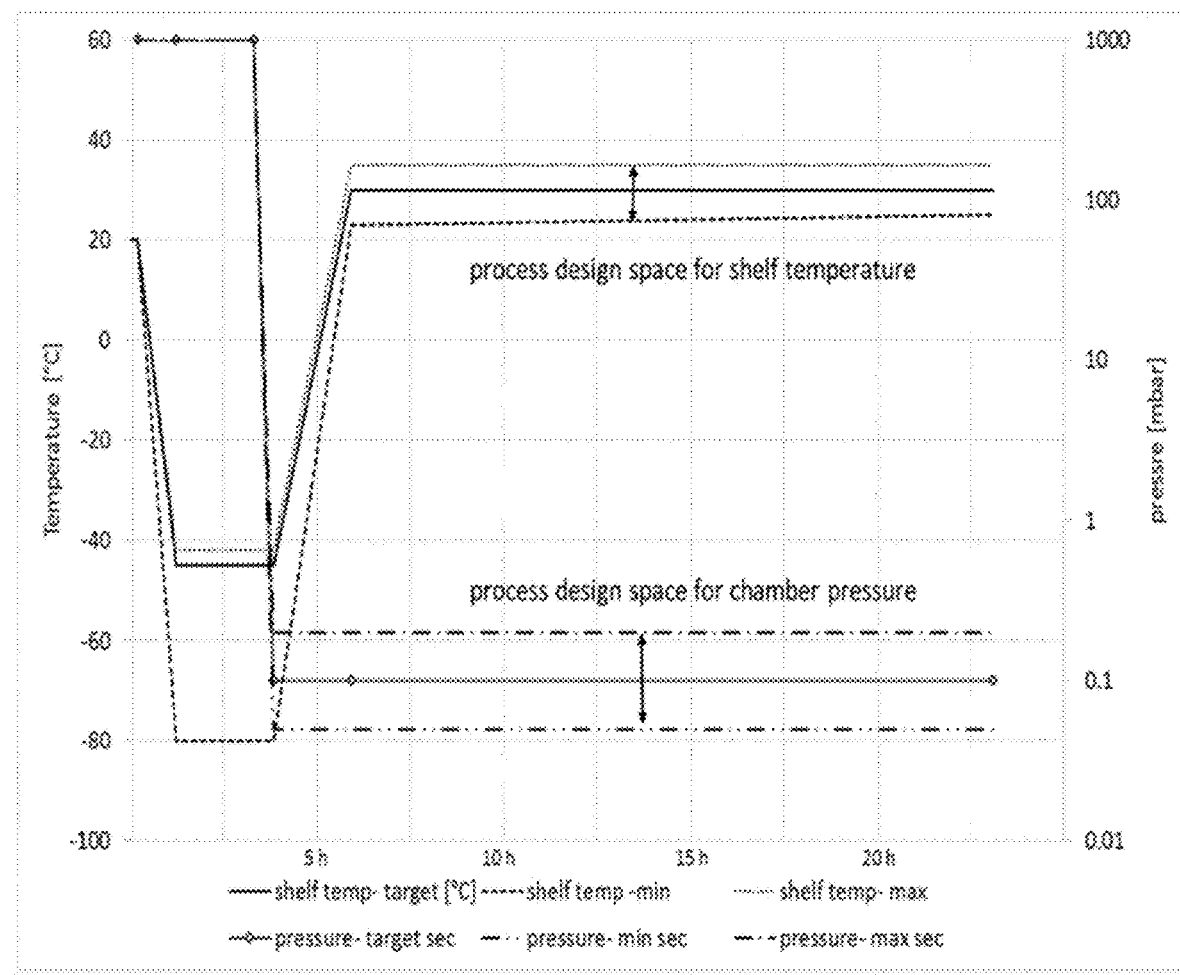

Lyophilisation was carried out with freezing at −80° C. and lyophilization at heated areas for 94 h. The final temperature was 15° C. 150 µl/well were lyophilized. Exemplary conditions are shown in FIG. 11 and Table 6.

TABLE 6

| Step | Description | critical step | shelf temp [° C.] Target | min | max | pressure [mbar] Target | min | max | time [h:min] Target | min | max |
|---|---|---|---|---|---|---|---|---|---|---|---|
| 1 | Equlibration | no | 20 | | | 1000 | | | 00:10 | | |
| 2 | Freezing | no | −45 | | | 1000 | | | 01:00 | | |
| 3 | Freezing | yes | −45 | | −42 | 1000 | | | 02:00 | | |
| 4 | Vacuum Adjustment | no | −45 | | | 0.1 | | | 00:30 | | |
| 5 | Drying ramp | no | 30 | | | 0.1 | | | 02:00 | | |
| 6 | Primary/ Secondary Drying | yes | 30 | 25 | 35 | 0.1 | 0.05 | 0.2 | 16:30 | 16:30 | 18:30 |

Aerogels were formed with all tested compositions. In particular, the aerogels formed by lyophilizing 40 mg/mL and 60 mg/mL solutions were easy to handle and apply into experimental periodontal pockets.

The formed material is shown in FIG. 7.

Example H—Experimental Administration of SAP Compositions in a Periodontitis Model Compositions according to the invention were tested on fresh ex vivo pig jaws. Adjacent to the molars, the alveolar ridge was exposed by incision of the mucosa, forming experimental periodontal pockets.

A 40 mg/ml lyophilized aerogel was introduced into the pocket and slightly pressed to the exposed bone. The aerogel stuck to the bone. The skin flap was closed and re-opened. Parts of the aerogel stuck to the skin flap, showing the excellent adhesion to the tissue (FIG. 8B). The skin flap stays in position. After 4 minutes, no movement is visible. After 4 minutes, the skin flap was reopened to check for maintenance of the aerogel. Part of the aerogel has been dissolved or turned into a gel, but stays within the pocket.

In alternative experiments, it could be confirmed that the aerogel also sticks to exposed root dentin. Upon addition of blood or serum-containing medium, the aerogels interact, but maintain form.

For a further experiment, implants were placed into porcine jaw, and defects recapitulating a peri-implantitis defect were set (FIG. 8 C). Patches (or aerogels) of lyophilized P11-4 hydrogels at 20 and 40 mg/ml generated according to Example G were placed in the furcation as well as peri-implantitis defect sites (FIG. 8D, E) and overlaid with human blood (FIG. 8F, G).

The patches attach very efficiently to the gingival tissue as well as to the root surface. They can be easily deformed to fill the defect space. Blood is soaked into the patch, but the patch is stable and does not dissolve. According to clinical experts, the patches are very well suited for peri-implantitis defects, in particular, when a full presentation of the defect is already present, as well as in furcation defects.

Example I—Experimental Administration of SAP Compositions in an In Vitro Periodontitis Model An in vitro model of a periodontal pocket (Meyer et al., 2016) was used to assess the migration distance of periodontal ligament fibroblasts (PDLF) out of the donor compartment. In brief, to determine early processes of tissue healing, three endpoints were investigated: Adhesion, proliferation and migration of human primary periodontal ligament fibroblasts (PDLF, ScienCell). In order to mimic the in vivo conditions as close as possible, pure bovine dentin surface served as underlying structure. Adhesion and proliferation of PDLF was assessed in a time dependent manner using ATP viability Kit (Promega). Visualization of the cells on the matrix was realized by SEM. For evaluation of cell adhesion and proliferation, Emdogain® (Straumann) was used as a positive control, as it has already proven its efficacy to promote periodontal regeneration in vivo. For assessment of migration speed and distance, a collagen I based cell donor compartment was placed on the dentin inside a special designed chamber, simulating a periodontal pocket.

FIG. 10A shows cell proliferation of human calvarial osteoblasts (HCO) after 3, 7 and 14 days incubation with SAP (15 mg/ml). Collagen (1.5 mg/ml) was used as a test system control. Cell proliferation was measured by the metabolic conversion of PrestoBlue viability reagent. Data were normalized in respect to values measured at day 1.

FIG. 10B shows collagen type 1 expression of HCO after 7, 14 and 21 days incubation with P11-4 (15 mg/ml). Cells grown on tissue culture plates (TCPS) were used as a control. Cell proliferation was measured by the metabolic conversion of PrestoBlue viability reagent. Data were normalized in respect to values measured at day 1.

Figure 2:
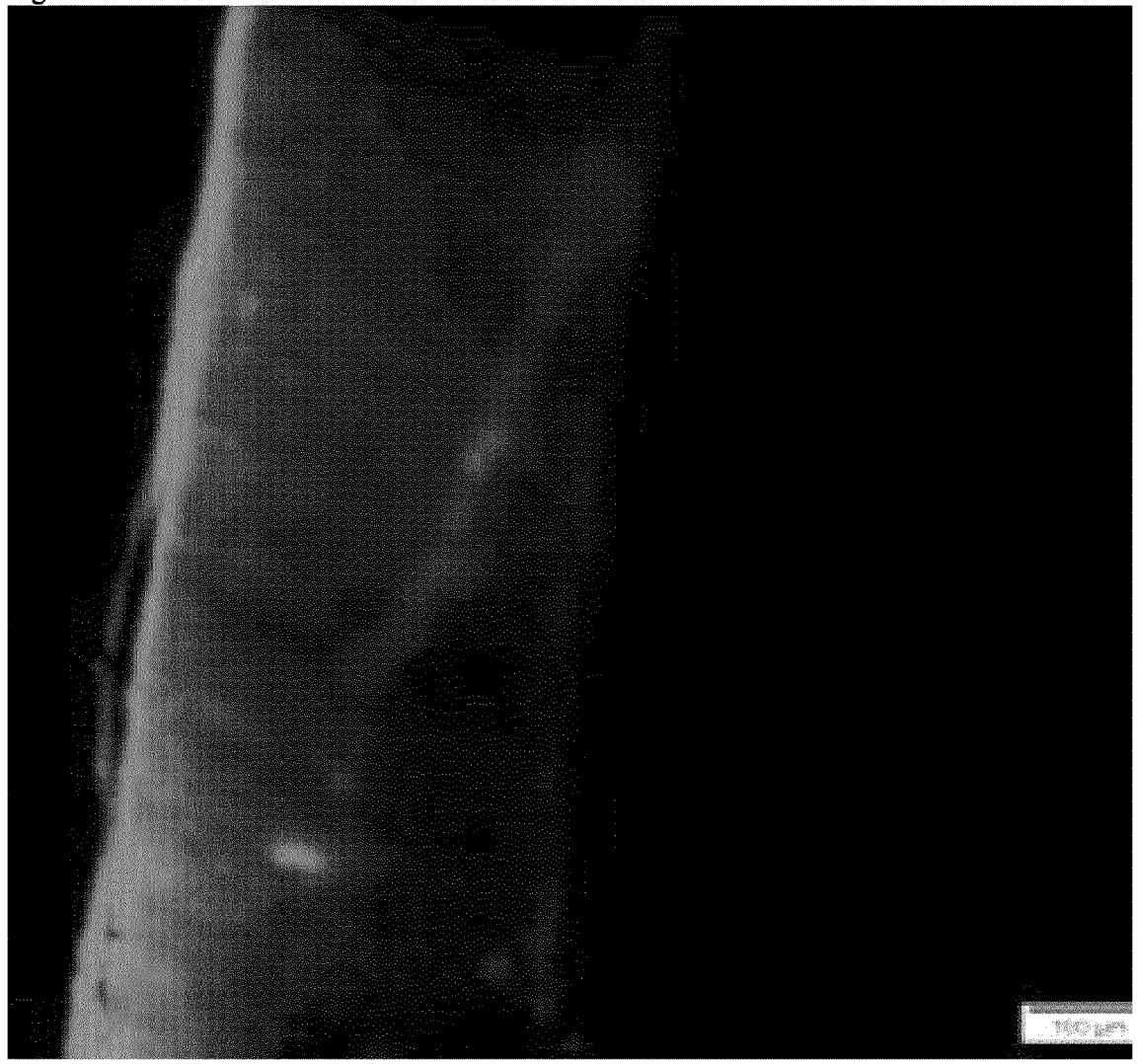
Figure 6:
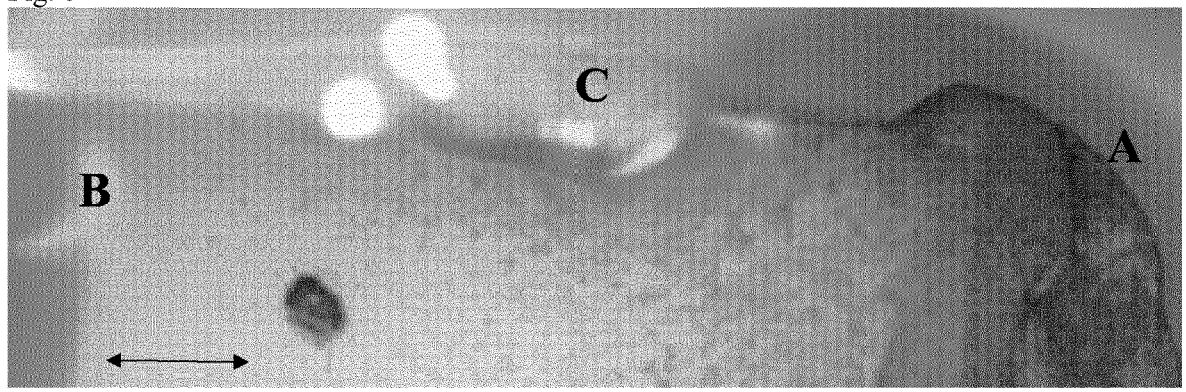
Figure 3:
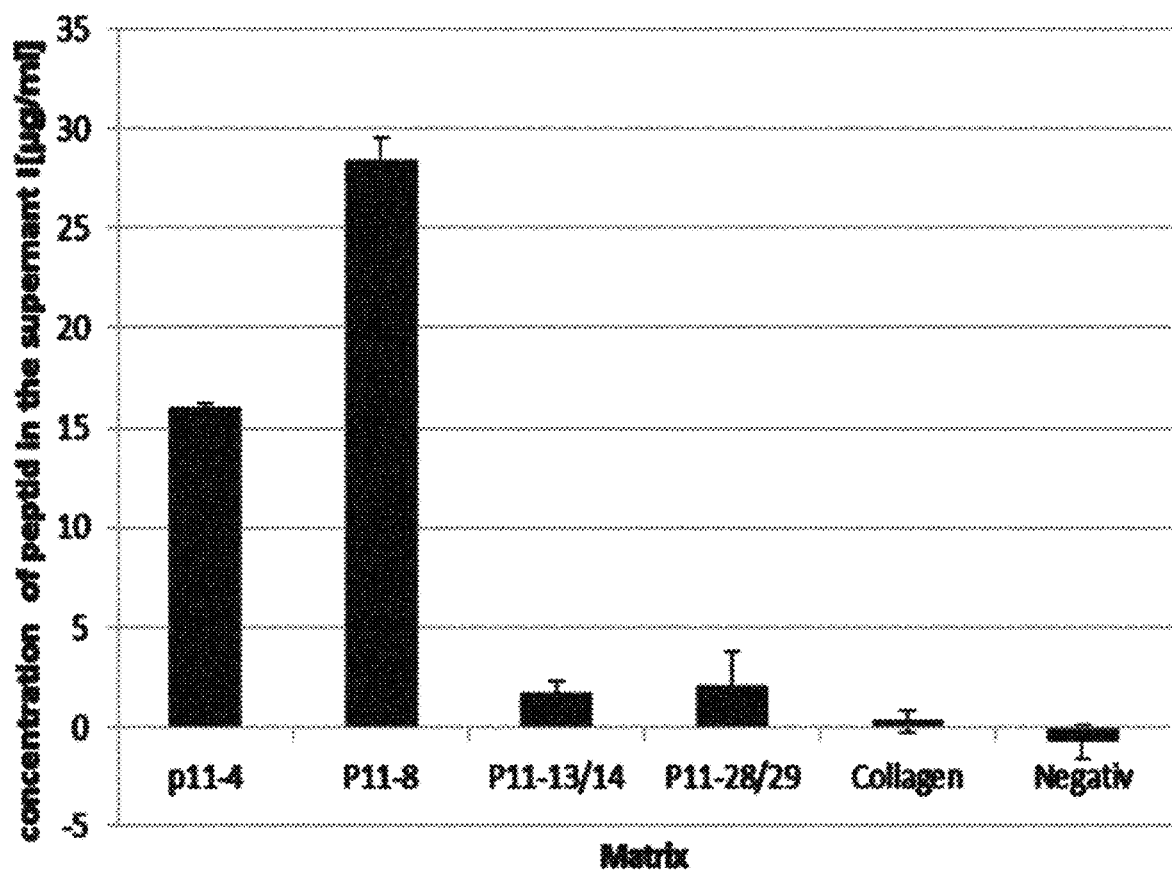
Figure 4:
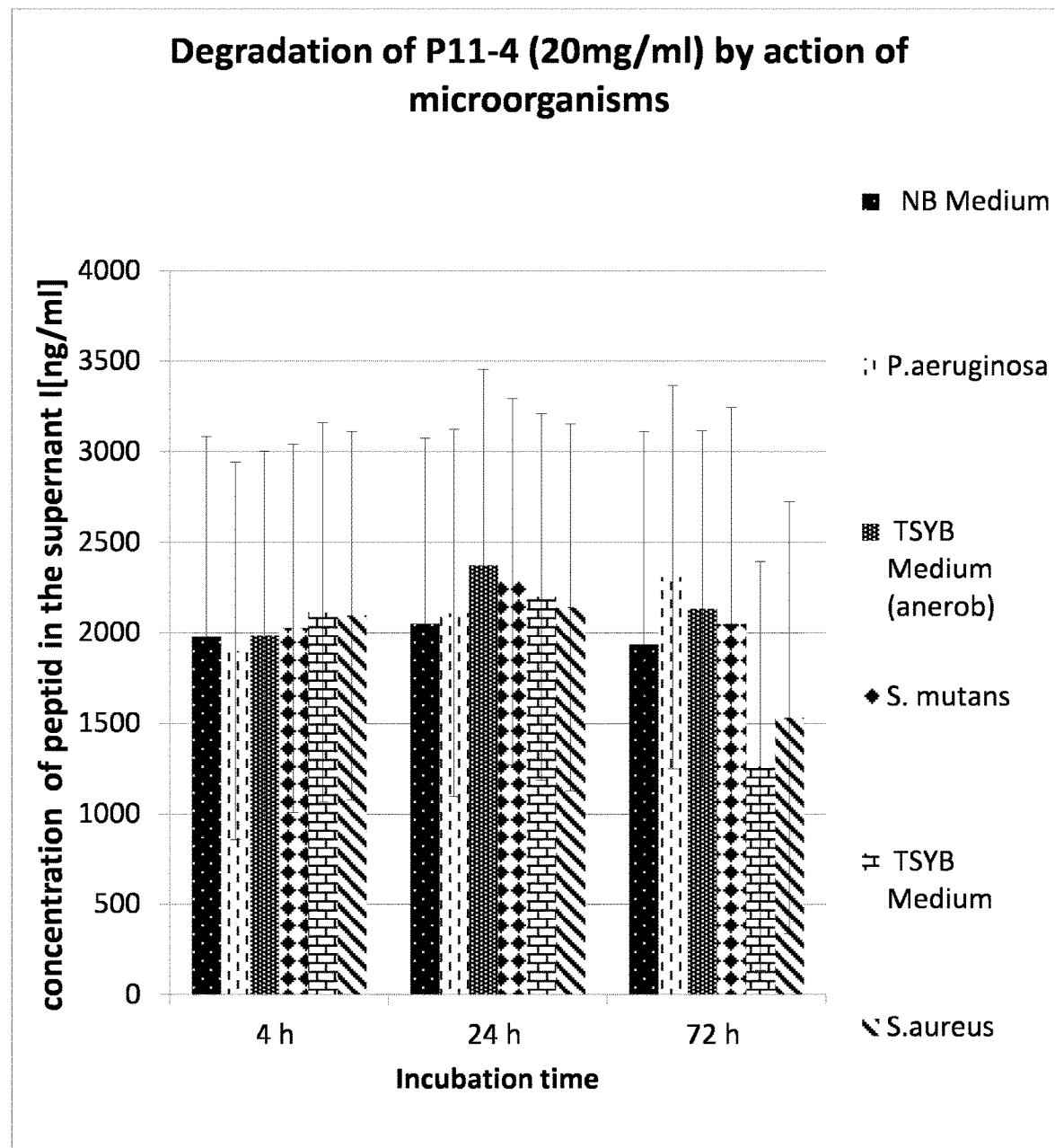
Figure 5A:
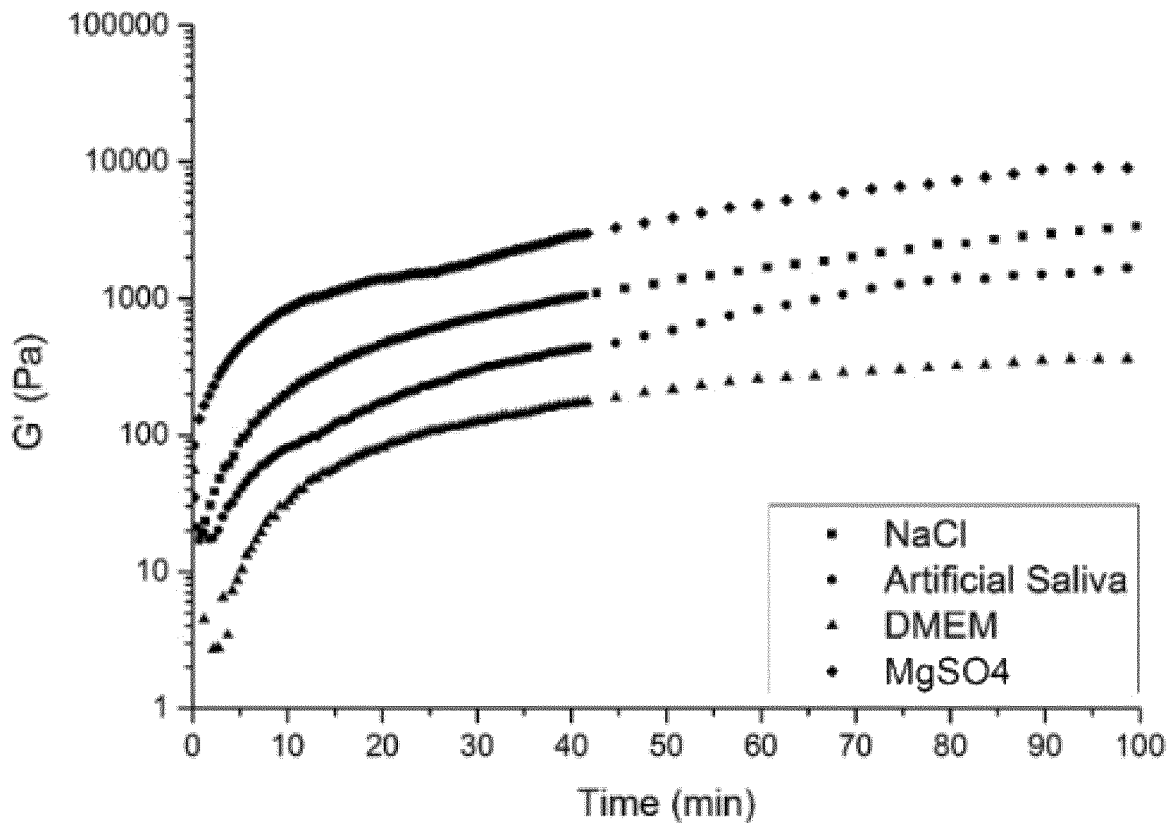
Figure 5B:
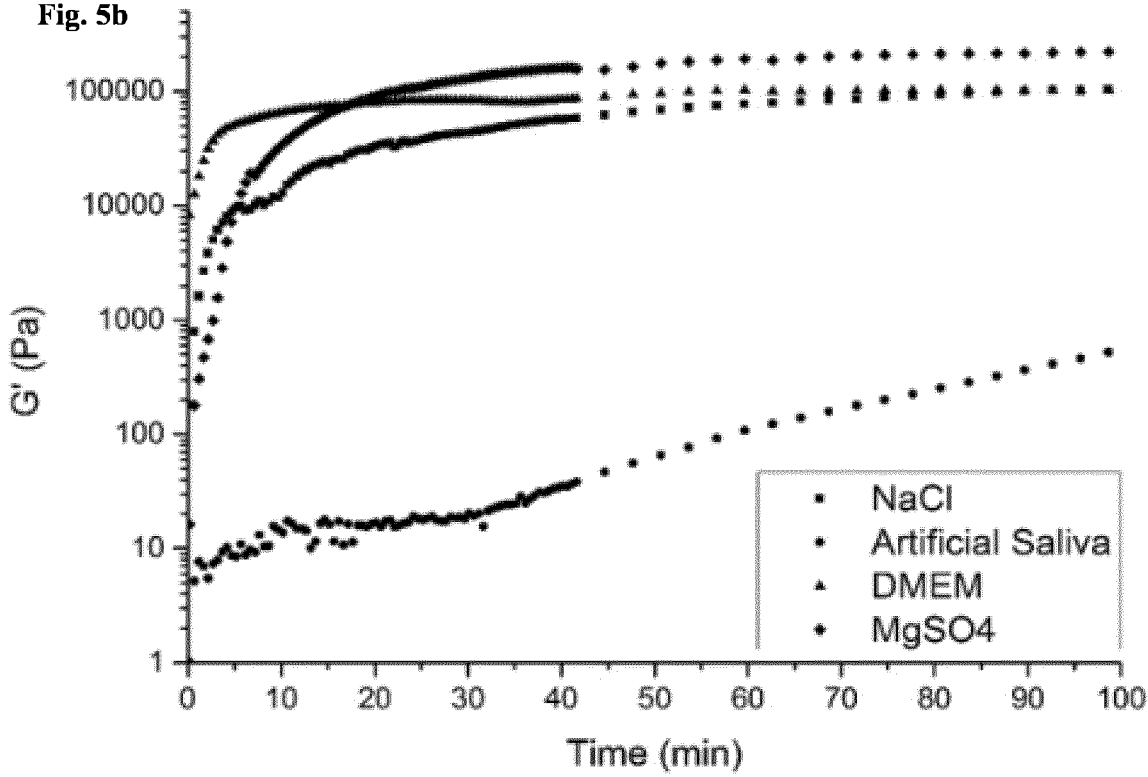
Figure 10C:
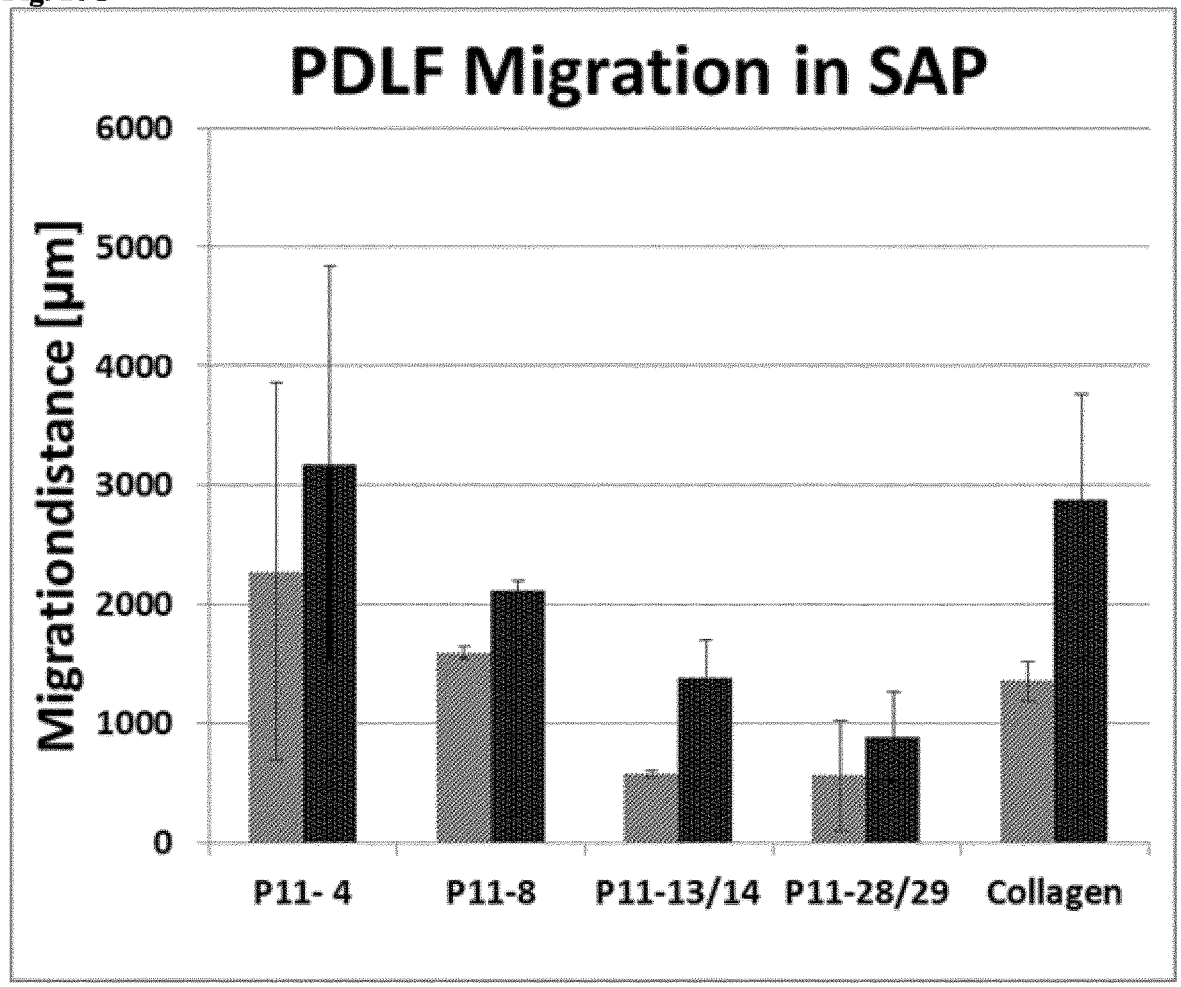

FIG. 10C shows the migration distance of periodontal ligament fibroblasts (PDLF) out of the donor compartment after 4 (left column) and 8 (right column) days for dentin surfaces coated with different tested SAP and, as a positive control, collagen.

It could further be shown that PDLF proliferate best on a P11-4 hydrogel. They also spread inside the matrix, but do not degrade the assembled SAP matrix.

Example J—Ex Vivo Application on Porcine Jaw a) Defect Generation

Using a drill, 2 and 3 wall defects as well as furcation defects were generated at different sites of the porcine jaw (FIG. 13A, arrows). They were opened by minimally invasive Periodontal therapy (MIST), and the flap opened (FIG. 13B).

b) Application of Emdogain®

Emdogain® was applied to a 2-wall defect (without Prep-Gel) with a bent needle for improved filling of the defect (FIG. 13C). Due to a high viscosity of the material, needle and syringe were coupled by Luer-lock. The material covered all surrounding surfaces well. The defect was closed by a suture (FIG. 13D). After closure and manual compression, only little material was pressed out.

c) Application of P11-4 Hydrogels

P11-4 gel (20 mg/ml, pH 7) was applied to a 2-wall defect without (FIG. 13E) and with supplementation of Trypan blue (TB, 0.02% wt/wt) for improved visibility of the hydrogel (FIG. 13F). Application with a bent needle improved filling of the defect. Due to a low viscosity of the material, the pure P11-4 gel did not stay at the defect site in an optimal manner. Stability of TB containing hydrogel was higher compared to pure peptide, and it stayed at the defect site in an improved manner. The defect was closed by suture. After closure and manual compression, no leakage of the material out of the suture was observed. After 2 hours, the suture was reopened. Even then, the material was clearly visible at the application site (FIG. 13G).

P11-4 gel (40 mg/ml, pH 7) was applied to a 2-wall defect without and with supplementation of Trypan blue (TB, 0.02% wt/wt) for improved visibility of the hydrogel (FIG. 13H), with similar results as for 20 mg/ml. However, here, the TB supplementation did not visibly increase viscosity. At this concentration, it is apparent that hydrogel is a non-Newtonian fluid, as it changes its viscosity upon pressure application (shear thinning) A liquid drop is shown in FIG. 13I. Hydrogel stability is recovered after a certain time after leaving the needle (FIG. 13J). This has the advantage that the hydrogel is more liquid when applied to the defect site, and therefore well distributed on the tissue and root surfaces, and then stabilized at place.

Application of P11-4 at 60 mg/ml was difficult due to strong gel formation.

The experiment leads to the conclusion that P11-4 gels are well suited for the application at a concentration of 15-50 mg/ml, 20-40 mg/ml or, preferably, 30-40 mg/ml. Supplementation with TB, e.g., at a concentration of 0.01-0.04%, e.g., 0.02-0.03%, is helpful for improved visibility in the in-vitro testing, and also recommended for increasing viscosity in lower concentrations, e.g., 15-25 mg/ml P11-4. This also applies for other self-assembling peptides, in particular, when viscosity of SAP hydrogel as such is too low. SAP can be used within the same routine as Emdogain®.

Example K—Proliferation of Cells on Self-Assembling Peptides Compared to Emdogain® and Collagen Proliferation of hPDLF (periodontal ligament fibroblasts) and SAOS-2 (Sarcoma osteogenic) cells on self-assembling peptides (P11-4, P11-8, P11-13 and P11-14, 15 mg/ml SAP, 20 mg/ml SAP, 30 mg/ml SAP respectively) was compared to the current gold standard Emdogain® and/or collagen after 24, 48 and 96 h. For Emdogain®, the concentration is constant at 30 mg/ml. Viability was measured by Presto-Blue® Cell Viability Reagent A13261.

At all concentrations tested, P11-4 and P11-8 lead to increased cell viability of hPDLF cells compared to Emdogain®. For SAOS-2 cells, at all concentrations tested, P11-4 lead to increased cell viability of the cells compared to Emdogain®, for P11-8, viability was strongly increased at 30 mg/ml and slightly increased or about equal at the other concentrations (FIGS. 14 A and B).

Cell proliferation of human calvarial osteoblasts (HCO) was analyzed after 3, 7 and 14 days incubation with different SAP (15 mg/ml). Collagen (1.5 mg/ml) was used as a test system control. Cell proliferation was measured by the metabolic conversion of PrestoBlue viability reagent. Data were normalized in respect to values measured at day 1. At the measured concentration, P11-4 led to similar proliferation as collagen (FIG. 14 C).

Example L—Attachment of Cells on Self-Assembling Peptides

PDLF cells were cultured for 24 h on pure bovine dentin surface (i.e., without SAP). Cell attachment was visualized by SEM. (FIG. 15A)

A periodontal model with dentin surface and cell donor compartment was set up. A model periodontal pocket of 5 mm is created with a PDLF containing hydrogel (pink) and a dentin surface (central slab) surrounded by agarose (FIG. 15B). Analysis of the cell migration distance is possible after MTT staining (FIG. 15C) (Meyer, et al. 2017), Migration with different SAP hydrogels is shown in FIG. 16.

Interaction of P11-4 with dentin of the root matrix of bovine teeth was analyzed with fluorescence labelled P11-4. 100 µl (20 mg/ml) labelled P11-4 hydrogel was contacted with the root matrix. The pictures were taken 24 h after the start of the incubation, and show that the SAP migrates into the dentin canals. For the pictures, samples were demineralized with EDTA 72 h, 4° C. and cut using a cryotome (FIG. 15D, G). Remineralization may thus not only be facilitated by the SAP on the surface of the tooth, but also within the dentin canals.

The migration of PDLF cells in a SAP hydrogel (P11-4, 20 mg/ml) was analyzed through phalloidin actin staining after 72 h incubation of the cells with a hydrogel block (FIGS. 15 E and F).

Example M—Migration Distances of PDLF Cells in SAP

PDLF cells were allowed to migrate in different SAP or collagen hydrogels (P11-4: 20 mg/ml; all others 15 mg/ml), as explained in Example L. Migration distances were analyzed after 4 and 8 days. Migration distances in P11-4 were comparable to migration distances in collagen both after 4 and 8 days. In P11-8, migration was slightly increased compared to collagen after 4, but not after 8 days. The cells also migrated in P11-13/14 and P11-28/29, but a decreased distance compared to collagen (FIG. 16). Visually, homogenous migration of PDLF cells is most obvious with P11-8.

Example N—Stability of Different SAP Matrices

Figure 17:
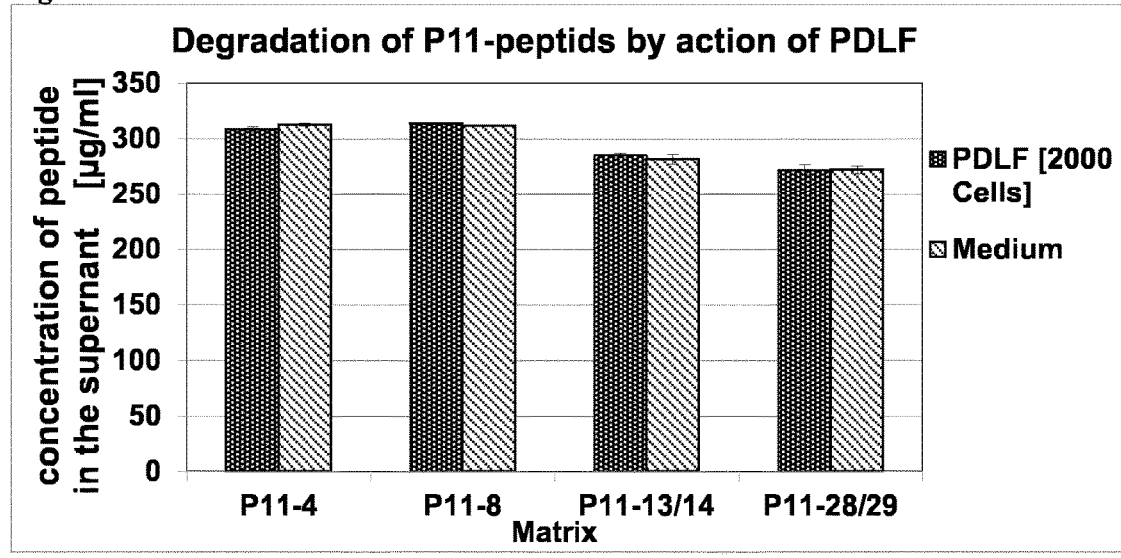
FIG. 17 shows stability of different SAP matrices (20 mg/ml for P11-4, all other peptides: 15 mg/ml) in contact with 2000 PDLF cells/well (left darker column, respectively) or medium (right column, respectively) after 24 h, measured by means of peptide concentration in the supernatant.

Different SAP hydrogels or matrices (20 mg/ml for P11-4; 15 mg/ml for P11-8 mg/ml) were contacted with 2000 PDLF cells/well or medium. Degradation was measured after 24 h by detection of peptide concentration in the supernatant by UV-spectroscopy. No significant effect of the cells was seen. P11-4 and P11-8 degraded slightly more than the other SAP (FIG. 17). In conclusion, the SAP hydrogels are stable even though, as shown in the other experiments, the cells proliferate and migrate in the hydrogels.

Example O—Expression of Extracellular Matrix Induced by SAP

HCO cells (5000 cells) were incubated with P11-4 (15 mg/ml (hydrogel). Cells grown on tissue culture plates (TCPS) were used as a control. The expression of collagen type I was detected after 7 14 and 21 days by MicroVue CICP assay measures type I C-terminal collagen propeptide and normalized to the proliferation rate, measured by the metabolic conversion of PrestoBlue viability reagent. Data were normalized in respect to values measured at day 1.

On each day, collagen expression was significantly greater with incubation with P11-4 (FIG. 18).

Expression of collagen type I, collagen type III, Fibrilin I, and Fibrilin II in 2000 cells after 7 days' incubation with P11-4 (20 mg/ml) was detected by antibody staining (10× magnification, primary antibody Anti-Fibrillin 1 antibody, secondary Antibody: Goat anti-Mouse IgG (H+L) Highly Cross-Adsorbed Secondary Antibody, Alexa Fluor 568).

Example P—In Vivo Trial

In a critical size, acute dehiscence, split mouth, gold standard controlled pre-clinical study in dog mandibles, a 30 mg*ml-1 hydrogel of P11-4 has been implanted. In comparison to void defects and defects filled with gold standard Straumann® Emdogain, P11-4 hydrogel showed the expected signs of healing and no device related events were recorded. A dehiscence is a localised gingival recession, as defined, e.g., www.pocketdentistry.com, which can be used as a model for inflammatory oral disorders, e.g., periodontitis or peri-implantiti.

LITERATURE

Ahuja, A., C. S. Baiju and V. Ahuja (2012). "Role of antibiotics in generalized aggressive periodontitis: A review of clinical trials in humans." *J Indian Soc Periodontol* 16(3): 317-323.

Cigognini, D., A. Satta, B. Colleoni, D. Silva, M. Donega, S. Antonini and F. Gelain (2011). "Evaluation of early and late effects into the acute spinal cord injury of an injectable functionalized self-assembling scaffold." *PLoS One* 6(5): e19782.

Diedrich, P., U. Fritz, G. Kinzinger and J. Angelakis (2003). "Movement of periodontally affected teeth after guided tissue regeneration (GTR)—an experimental pilot study in animals." *J Orofac Orthop* 64(3): 214-227.

Gelain, F., D. Bottai, A. Vescovi and S. Zhang (2006). "Designer self-assembling peptide nanofiber scaffolds for adult mouse neural stem cell 3-dimensional cultures." *PLoS One* 1: e119.

Gungormus, M., E. E. Oren, J. A. Horst, H. Fong, M. Hnilova, M. J. Somerman, M. L. Snead, R. Samudrala, C. Tamerler and M. Sarikaya (2012). "Cementomimetics-constructing a cementum-like biomineralized microlayer via amelogenin-derived peptides." *Int J Oral Sci* 4(2): 69-77.

Ho, D., M. Fitzgerald, C. A. Bartlett, B. Zdyrko, I. A. Luzinov, S. A. Dunlop and K. Swaminathan Iyer (2011). "The effects of concentration-dependent morphology of self-assembling RADA16 nanoscaffolds on mixed retinal cultures." *Nanoscale* 3(3): 907-910.

Hoang, A. M., T. W. Oates and D. L. Cochran (2000). "In vitro wound healing responses to enamel matrix derivative." *J Periodontol* 71(8): 1270-1277.

Holmes, T. C., S. de Lacalle, X. Su, G. Liu, A. Rich and S. Zhang (2000). "Extensive neurite outgrowth and active synapse formation on self-assembling peptide scaffolds." *Proc Natl Acad Sci USA* 97(12): 6728-6733.

Jiang, J., K. E. Safavi, L. S. Spangberg and Q. Zhu (2001). "Enamel matrix derivative prolongs primary osteoblast growth." *J Endod* 27(2): 110-112.

Kaigler, D., G. Avila, L. Wisner-Lynch, M. L. Nevins, M. Nevins, G. Rasperini, S. E. Lynch and W. V. Giannobile (2011). "Platelet-derived growth factor applications in periodontal and peri-implant bone regeneration." *Expert Opin Biol Ther* 11(3): 375-385.

Kind et al., 2017. "Biomimetic Remineralization of Carious Lesions by Self-Assembling Peptide". Journal of Dental Research 1-8 (DOI: 10.1177/0022034517698419)

Kisiday, J., M. Jin, B. Kurz, H. Hung, C. Semino, S. Zhang and A. J. Grodzinsky (2002). "Self-assembling peptide hydrogel fosters chondrocyte extracellular matrix production and cell division: implications for cartilage tissue repair." *Proc Natl Acad Sci USA* 99(15): 9996-10001.

Kumada, Y. and S. Zhang (2010). "Significant type I and type III collagen production from human periodontal ligament fibroblasts in 3D peptide scaffolds without extra growth factors." *PLoS One* 5(4): e10305.

Leonhardt A, Renvert S, Dahlen G. (1999). "Microbial findings at failing implants". *Clin Oral Implants Res* 10:339-345.

Liedmann, A., A. Rolfs and M. J. Frech (2012). "Cultivation of human neural progenitor cells in a 3-dimensional self-assembling peptide hydrogel." *J Vis Exp* (59): e3830.

Liu, X., X. Wang, H. Ren, J. He, L. Qiao and F. Z. Cui (2013). "Functionalized self-assembling peptide nanofiber hydrogels mimic stem cell niche to control human adipose stem cell behavior in vitro." *Acta Biomater* 9(6): 6798-6805.

Luo, Z., S. Wang and S. Zhang (2011). "Fabrication of self-assembling D-form peptide nanofiber scaffold d-EAK16 for rapid hemostasis." *Biomaterials* 32(8): 2013-2020.

Miller, R. E., P. W. Kopesky and A. J. Grodzinsky (2011). "Growth factor delivery through self-assembling peptide scaffolds." *Clin Orthop Relat Res* 469(10): 2716-2724.

Meyer N., F. Koch, R. Jung and S. Mathes (2016). In vitro model of the periodontal ligament to assess biomaterials for tissue regeneration. 3D Cell Culture 2016: How close to 'in vivo' can we get? Models, applications & translation. DECHEMA. Freiburg (DE).

Meyer, N., et al. (2017). IN VITRO PERIODONTAL LIGAMENT MODEL TO ASSESS SYNTHETIC SELF ASSEMBLING PEPTIDES FOR REGENERATION. TERMIS European Chapter Meeting 2017. Davos, termis.

Miron, R. J., O. M. Caluseru, V. Guillemette, Y. Zhang, A. C. Gemperli, F. Chandad and A. Sculean (2013). "Influence of enamel matrix derivative on cells at different maturation stages of differentiation." *PLoS One* 8(8): e71008.

Mombelli, A., Décaillet, F. (2011). "The characteristics of biofilms in peri-implant disease." *J Clin Periodontol.* 38 Suppl 11:203-13.

Nevins, M., R. T. Kao, M. K. McGuire, P. K. McClain, J. E. Hinrichs, B. S. McAllister, M. S. Reddy, M. L. Nevins, R. J. Genco, S. E. Lynch and W. V. Giannobile (2013). "Platelet-derived growth factor promotes periodontal regeneration in localized osseous defects: 36-month extension results from a randomized, controlled, double-masked clinical trial." *J Periodontol* 84(4): 456-464.

Nune, M., P. Kumaraswamy, U. M. Krishnan and S. Sethuraman (2013). "Self-assembling peptide nanofibrous scaffolds for tissue engineering: novel approaches and strategies for effective functional regeneration." *Curr Protein Pept Sci* 14(1): 70-84.

Schwarz, F., D. Rothamel, M. Herten, A. Sculean, W. Scherbaum and J. Becker (2004). "Effect of enamel matrix protein derivative on the attachment, proliferation, and viability of human SaOs(2) osteoblasts on titanium implants." *Clin Oral Investig* 8(3): 165-171.

Scanlon, A., A. Aggeli, N. Boden, R. J. Koopmans, R. Brydson and C. M. Rayner (2007). "Peptide aerogels comprising self-assembling nanofibrils". Micro & Nano Letters 2(2): 24-29.

Sculean, A., F. Rathe, R. Junker, J. Becker, F. Schwarz and N. Arweiler (2007). "Die Verwendung von Emdogain® in der parodontalen and ossären Regeneration." *Schweiz Monatsschr Zahnmed* 117: 598-606.

Silva, G. A., C. Czeisler, K. L. Niece, E. Beniash, D. A. Harrington, J. A. Kessler and S. I. Stupp (2004). "Selective differentiation of neural progenitor cells by high-epitope density nanofibers." *Science* 303(5662): 1352-1355.

Song, Y., Q. Zheng and J. Zheng (2010). "[Angiogenesis induced with neotype amphiphic peptide]." *Sheng Wu Yi Xue Gong Cheng Xue Za Zhi* 27(1): 113-115.

Sun, J. and Q. Zheng (2009). "Experimental study on self-assembly of KLD-12 peptide hydrogel and 3-D culture of MSC encapsulated within hydrogel in vitro." *J Huazhong Univ Sci Technolog Med Sci* 29(4): 512-516.

Takeuichi T. et al., (2016). "Enhanced healing of surgical priordontal effects in rats following application of a self-assembling peptide nanofibre hydrogel". J Clin Periodontol 43:279-288.

Thangakumaran, S., S. Sudarsan, K. V. Arun, A. Talwar and J. R. James (2009). "Osteoblast response (initial adhesion and alkaline phosphatase activity) following exposure to a barrier membrane/enamel matrix derivative combination." *Indian J Dent Res* 20(1): 7-12.

Tyagi, P., S. Vaish and V. Dodwad (2011). "Clinical efficacy of subgingivally delivered 0.5% controlled release azithromycin gel in the management of chronic periodontitis." *Indian J Med Sci* 65(6): 223-230.

Tysseling-Mattiace, V. M., V. Sahni, K. L. Niece, D. Birch, C. Czeisler, M. G. Fehlings, S. I. Stupp and J. A. Kessler (2008). "Self-assembling nanofibers inhibit glial scar formation and promote axon elongation after spinal cord injury." *J Neurosci* 28(14): 3814-3823.

Van der Pauw, M. T., T. Van den Bos, V. Everts and W. Beertsen (2000). "Enamel matrix-derived protein stimulates attachment of periodontal ligament fibroblasts and enhances alkaline phosphatase activity and transforming growth factor beta1 release of periodontal ligament and gingival fibroblasts." *J Periodontol* 71(1): 31-43.

Wu, B., Q. Zheng, Y. Wu, X. Guo and Z. Zou (2010). "Effect of IKVAV peptide nanofiber on proliferation, adhesion and differentiation into neurocytes of bone marrow stromal cells." *J Huazhong Univ Sci Technolog Med Sci* 30(2): 178-182.

Wu, Y., Q. Zheng, J. Du, Y. Song, B. Wu and X. Guo (2006). "Self-assembled IKVAV peptide nanofibers promote adherence of PC12 cells." *J Huazhong Univ Sci Technolog Med Sci* 26(5): 594-596.

Yuan, Y., C. Cong, J. Zhang, L. Wei, S. Li, Y. Chen, W. Tan, J. Cheng, Y. Li, X. Zhao and Y. Lu (2008). "Self-assembling peptide nanofiber as potential substrates in islet transplantation." *Transplant Proc* 40(8): 2571-2574.

Prathapachandran J, Suresh N. Management of peri-implantitis. Dental Research Journal. 2012; 9(5):516-521

WO 2004/007532 A1, U.S. Ser. No. 10/521,628, U.S. Ser. No. 12/729,046, U.S. Ser. No. 13/551,878, U.S. Ser. No. 14/062,768, WO 2014/027012 A1

The invention claimed is:

1. A method for treating an oral disease in a subject, comprising
    inserting a composition comprising self-assembling peptides into a pocket caused by gum and/or bone recession,
    wherein the self-assembling peptides are 11 amino acids in length, comprise the amino acid sequence SEQ ID NO:1, and have at least 81% sequence identity to SEQ ID NO: 6,
    wherein the self-assembling peptides are capable of self-assembly at a pH below 7.5 and at least physiologic ionic strength, and
    wherein the oral disease is selected from the group consisting of periodontitis, peri-implantitis and/or gingivitis.

2. The method of claim 1, wherein the oral disease is periodontitis.

3. The method of claim 1, wherein the oral disease is peri-implantitis.

4. The method of claim 1, wherein the oral disease is gingivitis.

5. The method of claim 1, wherein the self-assembling peptides consist of the sequence SEQ ID NO: 6.

6. The method of claim 1, wherein the treatment comprises
    a) cleaning and/or debridement of at least one tooth affected by the disease by root scaling or root planing,
    b) insertion of the composition into a pocket adjacent to said tooth caused by gum and/or bone recession caused by the oral disease, and
    c) covering the composition by a layer capable of reducing the invasion of bacteria from the oral cavity into the pocket.

7. The method of claim 1, wherein at least 70% of the self-assembling peptides are present in the composition in a monomeric state.

8. The method of claim 1, wherein the pH of the composition is 0.1 to 0.5 pH units above the pH wherein the peptide starts to undergo self-assembly.

9. The method of claim 1, wherein, after insertion of the composition into the pocket, a hydrogel forms by self-assembly of the peptides and inclusion of body liquids selected from the group consisting of blood, gingival crevicular fluid, saliva and a mixture thereof.

10. The method of claim 1, wherein the composition is a hydrogel comprising self-assembling peptides in assembled form and a liquid, wherein the liquid is selected from the group consisting of a buffer and the subject's blood and a mixture thereof.

11. The method of claim 1, wherein the composition comprises an antimicrobial, antibiotic, anti-inflammatory or antiseptic agent.

12. The method of claim 11, wherein the composition reduces the invasion of bacteria from the oral cavity into the pocket for at least 3 days.

13. The method of claim 1, wherein the composition is an aerogel composition.

14. The method of claim 11, wherein the agent is selected from the group consisting of taurolidine, chlorhexidine, doxycycline, tetracycline, azithromycin and minocycline.

15. The method of claim 1, wherein the self-assembling peptides consist of the sequence SEQ ID NO: 9.

16. The method of claim 6, wherein said layer is formed by a hydrogel comprising self-assembling peptides, wherein said hydrogel has a higher density and gel rigidity than a hydrogel formed after insertion of the composition into the pocket in step b).

17. The method of claim 11, wherein the composition reduces the invasion of bacteria from the oral cavity into the pocket for at least 7 days.

18. The method of claim 1, wherein the treatment comprises
    a) cleaning and/or debridement of at least one tooth affected by the disease by root scaling or root planing, and
    b) insertion of the composition into a pocket adjacent to said tooth caused by gum and/or bone recession caused by the oral disease.

19. The method of claim 1, wherein the oral disease is periodontitis and peri-implantitis.

* * * * *

SEQUENCE LISTING

```
<160> NUMBER OF SEQ ID NOS: 33

<210> SEQ ID NO 1
<211> LENGTH: 5
<212> TYPE: PRT
<213> ORGANISM: Artificial Sequence
<220> FEATURE:
<223> OTHER INFORMATION: consensus sequence 1 of self-assembling
      peptides
<220> FEATURE:
<221> NAME/KEY: VARIANT
<222> LOCATION: 1..1
<223> OTHER INFORMATION: amino acid X1 is independently selected from
      the group consisting of glutamic acid, aspartic acid, glutamine
      and ornithine
<220> FEATURE:
<221> NAME/KEY: VARIANT
<222> LOCATION: 2..2
<223> OTHER INFORMATION: amino acid X2 is independently selected from
      the group consisting of alanine, valine, isoleucine, leucine,
      methionine, phenylalanine, tyrosine, tryptophan and glutamine
<220> FEATURE:
<221> NAME/KEY: VARIANT
<222> LOCATION: 3..3
<223> OTHER INFORMATION: amino acid X1 is independently selected from
      the group consisting of glutamic acid, aspartic acid, glutamine
      and ornithine
<220> FEATURE:
<221> NAME/KEY: VARIANT
<222> LOCATION: 4..4
<223> OTHER INFORMATION: amino acid X2 is independently selected from
      the group consisting of alanine, valine, isoleucine, leucine,
      methionine, phenylalanine, tyrosine, tryptophan and glutamine
<220> FEATURE:
<221> NAME/KEY: VARIANT
<222> LOCATION: 5..5
<223> OTHER INFORMATION: amino acid X1 is independently selected from
      the group consisting of glutamic acid, aspartic acid, glutamine
      and ornithine

<400> SEQUENCE: 1

Xaa Xaa Xaa Xaa Xaa
1               5

<210> SEQ ID NO 2
<211> LENGTH: 5
<212> TYPE: PRT
<213> ORGANISM: Artificial Sequence
<220> FEATURE:
<223> OTHER INFORMATION: consensus sequence 2 of self-assembling
      peptides
<220> FEATURE:
<221> NAME/KEY: VARIANT
<222> LOCATION: 1..1
<223> OTHER INFORMATION: amino acid X1 is independently selected from
      the group consisting of glutamic acid and ornithine
<220> FEATURE:
<221> NAME/KEY: VARIANT
<222> LOCATION: 2..2
```

```
<223> OTHER INFORMATION: amino acid X2 is independently selected from
      the group consisting of phenylalanine and tryptophan
<220> FEATURE:
<221> NAME/KEY: VARIANT
<222> LOCATION: 3..3
<223> OTHER INFORMATION: amino acid X1 is independently selected from
      the group consisting of glutamic acid and ornithine
<220> FEATURE:
<221> NAME/KEY: VARIANT
<222> LOCATION: 4..4
<223> OTHER INFORMATION: amino acid X2 is independently selected from
      the group consisting of phenylalanine and tryptophan
<220> FEATURE:
<221> NAME/KEY: VARIANT
<222> LOCATION: 5..5
<223> OTHER INFORMATION: amino acid X1 is independently selected from
      the group consisting of glutamic acid and ornithine

<400> SEQUENCE: 2

Xaa Xaa Xaa Xaa Xaa
1               5

<210> SEQ ID NO 3
<211> LENGTH: 5
<212> TYPE: PRT
<213> ORGANISM: Artificial Sequence
<220> FEATURE:
<223> OTHER INFORMATION: consensus sequence 3 of self-assembling
      peptides
<220> FEATURE:
<221> NAME/KEY: VARIANT
<222> LOCATION: 1..1
<223> OTHER INFORMATION: amino acid X3 is independently selected from
      the group consisting of arginine, glutamic acid and ornithine
<220> FEATURE:
<221> NAME/KEY: VARIANT
<222> LOCATION: 3..3
<223> OTHER INFORMATION: amino acid X1 is independently selected from
      the group consisting of glutamic acid and ornithine
<220> FEATURE:
<221> NAME/KEY: VARIANT
<222> LOCATION: 5..5
<223> OTHER INFORMATION: amino acid X1 is independently selected from
      the group consisting of glutamic acid and ornithine

<400> SEQUENCE: 3

Xaa Phe Xaa Trp Xaa
1               5

<210> SEQ ID NO 4
<211> LENGTH: 11
<212> TYPE: PRT
<213> ORGANISM: Artificial Sequence
<220> FEATURE:
<223> OTHER INFORMATION: consensus sequence 4 of self-assembling
      peptides
<220> FEATURE:
<221> NAME/KEY: VARIANT
<222> LOCATION: 1..1
<223> OTHER INFORMATION: amino acid X4 is independently selected from
      the group consisting of glutamine, glutamic acid, serine,
      threonine and ornithine
<220> FEATURE:
<221> NAME/KEY: VARIANT
<222> LOCATION: 2..2
<223> OTHER INFORMATION: amino acid X4 is independently selected from
      the group consisting of glutamine, glutamic acid, serine,
      threonine and ornithine
<220> FEATURE:
<221> NAME/KEY: VARIANT
<222> LOCATION: 3..3
<223> OTHER INFORMATION: amino acid X3 is independently selected from
      the group consisting of arginine, glutamic acid and ornithine
<220> FEATURE:
<221> NAME/KEY: VARIANT
```

```
<222> LOCATION: 5..5
<223> OTHER INFORMATION: amino acid X1 is independently selected from
      the group consisting of glutamic acid and ornithine
<220> FEATURE:
<221> NAME/KEY: VARIANT
<222> LOCATION: 7..7
<223> OTHER INFORMATION: amino acid X1 is independently selected from
      the group consisting of glutamic acid and ornithine
<220> FEATURE:
<221> NAME/KEY: VARIANT
<222> LOCATION: 9..9
<223> OTHER INFORMATION: amino acid X1 is independently selected from
      the group consisting of glutamic acid and ornithine
<220> FEATURE:
<221> NAME/KEY: VARIANT
<222> LOCATION: 10..10
<223> OTHER INFORMATION: amino acid X4 is independently selected from
      the group consisting glutamine, glutamic acid, serine, threonine
      and ornithine
<220> FEATURE:
<221> NAME/KEY: VARIANT
<222> LOCATION: 11..11
<223> OTHER INFORMATION: amino acid X4 is independently selected from
      the group consisting glutamine, glutamic acid, serine, threonine
      and ornithine

<400> SEQUENCE: 4

Xaa Xaa Xaa Phe Xaa Trp Xaa Phe Xaa Xaa Xaa
1               5                   10

<210> SEQ ID NO 5
<211> LENGTH: 11
<212> TYPE: PRT
<213> ORGANISM: Artificial Sequence
<220> FEATURE:
<223> OTHER INFORMATION: consensus sequence 5 of self-assembling
      peptides
<220> FEATURE:
<221> NAME/KEY: VARIANT
<222> LOCATION: 5..5
<223> OTHER INFORMATION: amino acid X1 is independently selected from
      the group consisting of glutamic acid and ornithine
<220> FEATURE:
<221> NAME/KEY: VARIANT
<222> LOCATION: 7..7
<223> OTHER INFORMATION: amino acid X1 is independently selected from
      the group consisting of glutamic acid and ornithine
<220> FEATURE:
<221> NAME/KEY: VARIANT
<222> LOCATION: 9..9
<223> OTHER INFORMATION: amino acid X1 is independently selected from
      the group consisting of glutamic acid and ornithine

<400> SEQUENCE: 5

Gln Gln Arg Phe Xaa Trp Xaa Phe Xaa Gln Gln
1               5                   10

<210> SEQ ID NO 6
<211> LENGTH: 11
<212> TYPE: PRT
<213> ORGANISM: Artificial Sequence
<220> FEATURE:
<223> OTHER INFORMATION: P11-4

<400> SEQUENCE: 6

Gln Gln Arg Phe Glu Trp Glu Phe Glu Gln Gln
1               5                   10

<210> SEQ ID NO 7
<211> LENGTH: 11
<212> TYPE: PRT
<213> ORGANISM: Artificial Sequence
<220> FEATURE:
```

<223> OTHER INFORMATION: P11-2

<400> SEQUENCE: 7

Gln Gln Arg Phe Gln Trp Gln Phe Glu Gln Gln
1               5                   10

<210> SEQ ID NO 8
<211> LENGTH: 11
<212> TYPE: PRT
<213> ORGANISM: Artificial Sequence
<220> FEATURE:
<223> OTHER INFORMATION: P11-5
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7..7
<223> OTHER INFORMATION: ornithine

<400> SEQUENCE: 8

Gln Gln Arg Phe Xaa Trp Xaa Phe Gln Gln Gln
1               5                   10

<210> SEQ ID NO 9
<211> LENGTH: 11
<212> TYPE: PRT
<213> ORGANISM: Artificial Sequence
<220> FEATURE:
<223> OTHER INFORMATION: P11-8
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7..7
<223> OTHER INFORMATION: ornithine

<400> SEQUENCE: 9

Gln Gln Arg Phe Xaa Trp Xaa Phe Glu Gln Gln
1               5                   10

<210> SEQ ID NO 10
<211> LENGTH: 11
<212> TYPE: PRT
<213> ORGANISM: Artificial Sequence
<220> FEATURE:
<223> OTHER INFORMATION: P11-12
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7..7
<223> OTHER INFORMATION: ornithine

<400> SEQUENCE: 10

Ser Ser Arg Phe Xaa Trp Xaa Phe Glu Ser Ser
1               5                   10

<210> SEQ ID NO 11
<211> LENGTH: 11
<212> TYPE: PRT
<213> ORGANISM: Artificial Sequence
<220> FEATURE:
<223> OTHER INFORMATION: P11-13

<400> SEQUENCE: 11

Glu Gln Glu Phe Glu Trp Glu Phe Glu Gln Glu
1               5                   10

<210> SEQ ID NO 12
<211> LENGTH: 11
<212> TYPE: PRT
<213> ORGANISM: Artificial Sequence
<220> FEATURE:
<223> OTHER INFORMATION: P11-14
<220> FEATURE:
<221> NAME/KEY: MOD_RES
<222> LOCATION: 3..3
<223> OTHER INFORMATION: ornithine
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7..7
<223> OTHER INFORMATION: ornithine
<220> FEATURE:
<221> NAME/KEY: MOD_RES
<222> LOCATION: 9..9
<223> OTHER INFORMATION: ornithine

<400> SEQUENCE: 12

Gln Gln Xaa Phe Xaa Trp Xaa Phe Xaa Gln Gln
1               5                   10

<210> SEQ ID NO 13
<211> LENGTH: 11
<212> TYPE: PRT
<213> ORGANISM: Artificial Sequence
<220> FEATURE:
<223> OTHER INFORMATION: P11-17

<400> SEQUENCE: 13

Thr Thr Arg Phe Glu Trp Glu Phe Glu Thr Thr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: P11-19
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7..7
<223> OTHER INFORMATION: ornithine

<400> SEQUENCE: 14

Gln Gln Arg Gln Xaa Gln Xaa Gln Glu Gln Gln
1               5                   10

<210> SEQ ID NO 15
<211> LENGTH: 11
<212> TYPE: PRT
<213> ORGANISM: Artificial Sequence
<220> FEATURE:
<223> OTHER INFORMATION: P11-20

<400> SEQUENCE: 15

Gln Gln Arg Gln Glu Gln Glu Gln Glu Gln Gln
1               5                   10

```
<210> SEQ ID NO 16
<211> LENGTH: 11
<212> TYPE: PRT
<213> ORGANISM: Artificial Sequence
<220> FEATURE:
<221> NAME/KEY: MOD_RES
<222> LOCATION: 1..1
<223> OTHER INFORMATION: ornithine
<220> FEATURE:
<223> OTHER INFORMATION: P11-28
<220> FEATURE:
<221> NAME/KEY: MOD_RES
<222> LOCATION: 3..3
<223> OTHER INFORMATION: ornithine
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7..7
<223> OTHER INFORMATION: ornithine
<220> FEATURE:
<221> NAME/KEY: MOD_RES
<222> LOCATION: 9..9
<223> OTHER INFORMATION: ornithine
<220> FEATURE:
<221> NAME/KEY: MOD_RES
<222> LOCATION: 11..11
<223> OTHER INFORMATION: ornithine

<400> SEQUENCE: 16

Xaa Gln Xaa Phe Xaa Trp Xaa Phe Xaa Gln Xaa
1               5                   10

<210> SEQ ID NO 17
<211> LENGTH: 11
<212> TYPE: PRT
<213> ORGANISM: Artificial Sequence
<220> FEATURE:
<223> OTHER INFORMATION: P11-29

<400> SEQUENCE: 17

Gln Gln Glu Phe Glu Trp Glu Phe Glu Gln Gln
1               5                   10

<210> SEQ ID NO 18
<211> LENGTH: 11
<212> TYPE: PRT
<213> ORGANISM: Artificial Sequence
<220> FEATURE:
<221> NAME/KEY: MOD_RES
<222> LOCATION: 1..1
<223> OTHER INFORMATION: ACETYLATION
<220> FEATURE:
<223> OTHER INFORMATION: P11-4mod
<220> FEATURE:
<221> NAME/KEY: MOD_RES
<222> LOCATION: 11..11
<223> OTHER INFORMATION: AMIDATION

<400> SEQUENCE: 18

Gln Gln Arg Phe Glu Trp Glu Phe Glu Gln Gln
1               5                   10

<210> SEQ ID NO 19
<211> LENGTH: 11
<212> TYPE: PRT
<213> ORGANISM: Artificial Sequence
<220> FEATURE:
<221> NAME/KEY: MOD_RES
```

```
<222> LOCATION: 1..1
<223> OTHER INFORMATION: ACETYLATION
<220> FEATURE:
<223> OTHER INFORMATION: P11-2mod
<220> FEATURE:
<221> NAME/KEY: MOD_RES
<222> LOCATION: 11..11
<223> OTHER INFORMATION: AMIDATION

<400> SEQUENCE: 19

Gln Gln Arg Phe Gln Trp Gln Phe Glu Gln Gln
1               5                   10

<210> SEQ ID NO 20
<211> LENGTH: 11
<212> TYPE: PRT
<213> ORGANISM: Artificial Sequence
<220> FEATURE:
<221> NAME/KEY: MOD_RES
<222> LOCATION: 1..1
<223> OTHER INFORMATION: ACETYLATION
<220> FEATURE:
<223> OTHER INFORMATION: P11-5mod
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7..7
<223> OTHER INFORMATION: ornithine
<220> FEATURE:
<221> NAME/KEY: MOD_RES
<222> LOCATION: 11..11
<223> OTHER INFORMATION: AMIDATION

<400> SEQUENCE: 20

Gln Gln Arg Phe Xaa Trp Xaa Phe Gln Gln Gln
1               5                   10

<210> SEQ ID NO 21
<211> LENGTH: 11
<212> TYPE: PRT
<213> ORGANISM: Artificial Sequence
<220> FEATURE:
<221> NAME/KEY: MOD_RES
<222> LOCATION: 1..1
<223> OTHER INFORMATION: ACETYLATION
<220> FEATURE:
<223> OTHER INFORMATION: P11-8mod
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7..7
<223> OTHER INFORMATION: ornithine
<220> FEATURE:
<221> NAME/KEY: MOD_RES
<222> LOCATION: 11..11
<223> OTHER INFORMATION: AMIDATION

<400> SEQUENCE: 21

Gln Gln Arg Phe Xaa Trp Xaa Phe Glu Gln Gln
1               5                   10

<210> SEQ ID NO 22
<211> LENGTH: 11
<212> TYPE: PRT
<213> ORGANISM: Artificial Sequence
<220> FEATURE:
<221> NAME/KEY: MOD_RES
```

```
<222> LOCATION: 1..1
<223> OTHER INFORMATION: ACETYLATION
<220> FEATURE:
<223> OTHER INFORMATION: P11-12mod
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7..7
<223> OTHER INFORMATION: ornithine
<220> FEATURE:
<221> NAME/KEY: MOD_RES
<222> LOCATION: 11..11
<223> OTHER INFORMATION: AMIDATION

<400> SEQUENCE: 22

Ser Ser Arg Phe Xaa Trp Xaa Phe Glu Ser Ser
1               5                   10

<210> SEQ ID NO 23
<211> LENGTH: 11
<212> TYPE: PRT
<213> ORGANISM: Artificial Sequence
<220> FEATURE:
<221> NAME/KEY: MOD_RES
<222> LOCATION: 1..1
<223> OTHER INFORMATION: ACETYLATION
<220> FEATURE:
<223> OTHER INFORMATION: P11-13mod
<220> FEATURE:
<221> NAME/KEY: MOD_RES
<222> LOCATION: 11..11
<223> OTHER INFORMATION: AMIDATION

<400> SEQUENCE: 23

Glu Gln Glu Phe Glu Trp Glu Phe Glu Gln Glu
1               5                   10

<210> SEQ ID NO 24
<211> LENGTH: 11
<212> TYPE: PRT
<213> ORGANISM: Artificial Sequence
<220> FEATURE:
<221> NAME/KEY: MOD_RES
<222> LOCATION: 1..1
<223> OTHER INFORMATION: ACETYLATION
<220> FEATURE:
<223> OTHER INFORMATION: P11-14mod
<220> FEATURE:
<221> NAME/KEY: MOD_RES
<222> LOCATION: 3..3
<223> OTHER INFORMATION: ornithine
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7..7
<223> OTHER INFORMATION: ornithine
<220> FEATURE:
<221> NAME/KEY: MOD_RES
<222> LOCATION: 9..9
<223> OTHER INFORMATION: ornithine
<220> FEATURE:
<221> NAME/KEY: MOD_RES
<222> LOCATION: 11..11
<223> OTHER INFORMATION: AMIDATION

<400> SEQUENCE: 24

Gln Gln Xaa Phe Xaa Trp Xaa Phe Xaa Gln Gln
1               5                   10
```

```
<210> SEQ ID NO 25
<211> LENGTH: 11
<212> TYPE: PRT
<213> ORGANISM: Artificial Sequence
<220> FEATURE:
<221> NAME/KEY: MOD_RES
<222> LOCATION: 1..1
<223> OTHER INFORMATION: ACETYLATION
<220> FEATURE:
<223> OTHER INFORMATION: P11-17mod
<220> FEATURE:
<221> NAME/KEY: MOD_RES
<222> LOCATION: 11..11
<223> OTHER INFORMATION: AMIDATION

<400> SEQUENCE: 25

Thr Thr Arg Phe Glu Trp Glu Phe Glu Thr Thr
1               5                   10

<210> SEQ ID NO 26
<211> LENGTH: 11
<212> TYPE: PRT
<213> ORGANISM: Artificial Sequence
<220> FEATURE:
<221> NAME/KEY: MOD_RES
<222> LOCATION: 1..1
<223> OTHER INFORMATION: ACETYLATION
<220> FEATURE:
<223> OTHER INFORMATION: P11-19mod
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7..7
<223> OTHER INFORMATION: ornithine
<220> FEATURE:
<221> NAME/KEY: MOD_RES
<222> LOCATION: 11..11
<223> OTHER INFORMATION: AMIDATION

<400> SEQUENCE: 26

Gln Gln Arg Gln Xaa Gln Xaa Gln Glu Gln Gln
1               5                   10

<210> SEQ ID NO 27
<211> LENGTH: 11
<212> TYPE: PRT
<213> ORGANISM: Artificial Sequence
<220> FEATURE:
<221> NAME/KEY: MOD_RES
<222> LOCATION: 1..1
<223> OTHER INFORMATION: ACETYLATION
<220> FEATURE:
<223> OTHER INFORMATION: P11-20mod
<220> FEATURE:
<221> NAME/KEY: MOD_RES
<222> LOCATION: 11..11
<223> OTHER INFORMATION: AMIDATION

<400> SEQUENCE: 27

Gln Gln Arg Gln Glu Gln Glu Gln Glu Gln Gln
1               5                   10

<210> SEQ ID NO 28
<211> LENGTH: 11
<212> TYPE: PRT
<213> ORGANISM: Artificial Sequence
<220> FEATURE:
<221> NAME/KEY: MOD_RES
```

```
<222> LOCATION: 1..1
<223> OTHER INFORMATION: ACETYLATION
<220> FEATURE:
<221> NAME/KEY: MOD_RES
<222> LOCATION: 1..1
<223> OTHER INFORMATION: ornithine
<220> FEATURE:
<223> OTHER INFORMATION: P11-28mod
<220> FEATURE:
<221> NAME/KEY: MOD_RES
<222> LOCATION: 3..3
<223> OTHER INFORMATION: ornithine
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7..7
<223> OTHER INFORMATION: ornithine
<220> FEATURE:
<221> NAME/KEY: MOD_RES
<222> LOCATION: 9..9
<223> OTHER INFORMATION: ornithine
<220> FEATURE:
<221> NAME/KEY: MOD_RES
<222> LOCATION: 11..11
<223> OTHER INFORMATION: ornithine
<220> FEATURE:
<221> NAME/KEY: MOD_RES
<222> LOCATION: 11..11
<223> OTHER INFORMATION: AMIDATION

<400> SEQUENCE: 28

Xaa Gln Xaa Phe Xaa Trp Xaa Phe Xaa Gln Xaa
1               5                   10

<210> SEQ ID NO 29
<211> LENGTH: 11
<212> TYPE: PRT
<213> ORGANISM: Artificial Sequence
<220> FEATURE:
<221> NAME/KEY: MOD_RES
<222> LOCATION: 1..1
<223> OTHER INFORMATION: ACETYLATION
<220> FEATURE:
<223> OTHER INFORMATION: P11-29mod
<220> FEATURE:
<221> NAME/KEY: MOD_RES
<222> LOCATION: 11..11
<223> OTHER INFORMATION: AMIDATION

<400> SEQUENCE: 29

Gln Gln Glu Phe Glu Trp Glu Phe Glu Gln Gln
1               5                   10

<210> SEQ ID NO 30
<211> LENGTH: 11
<212> TYPE: PRT
<213> ORGANISM: Artificial Sequence
<220> FEATURE:
<223> OTHER INFORMATION: P11-16
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7
<223> OTHER INFORMATION: ornithine

<400> SEQUENCE: 30

Asn Asn Arg Phe Xaa Trp Xaa Phe Glu Asn Asn
1               5                   10
```

```
<210> SEQ ID NO 31
<211> LENGTH: 11
<212> TYPE: PRT
<213> ORGANISM: Artificial Sequence
<220> FEATURE:
<223> OTHER INFORMATION: P11-18
<220> FEATURE:
<221> NAME/KEY: MOD_RES
<222> LOCATION: 5..5
<223> OTHER INFORMATION: ornithine
<220> FEATURE:
<221> NAME/KEY: MOD_RES
<222> LOCATION: 7
<223> OTHER INFORMATION: ornithine

<400> SEQUENCE: 31

Thr Thr Arg Phe Xaa Trp Xaa Phe Glu Thr Thr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: P11-26
<220> FEATURE:
<221> NAME/KEY: MOD_RES
<222> LOCATION: 3
<223> OTHER INFORMATION: ornithine
<220> FEATURE:
<221> NAME/KEY: MOD_RES
<222> LOCATION: 5
<223> OTHER INFORMATION: ornithine
<220> FEATURE:
<221> NAME/KEY: MOD_RES
<222> LOCATION: 7
<223> OTHER INFORMATION: ornithine
<220> FEATURE:
<221> NAME/KEY: MOD_RES
<222> LOCATION: 9
<223> OTHER INFORMATION: ornithine

<400> SEQUENCE: 32

Gln Gln Xaa Gln Xaa Gln Xaa Gln Xaa Gln Gln
1               5                   10

<210> SEQ ID NO 33
<211> LENGTH: 11
<212> TYPE: PRT
<213> ORGANISM: Artificial Sequence
<220> FEATURE:
<223> OTHER INFORMATION: P11-31
<220> FEATURE:
<221> NAME/KEY: MOD_RES
<222> LOCATION: 3
<223> OTHER INFORMATION: ornithine
<220> FEATURE:
<221> NAME/KEY: MOD_RES
<222> LOCATION: 5
<223> OTHER INFORMATION: ornithine
<220> FEATURE:
<221> NAME/KEY: MOD_RES
<222> LOCATION: 7
<223> OTHER INFORMATION: ornithine
<220> FEATURE:
<221> NAME/KEY: MOD_RES
<222> LOCATION: 9
<223> OTHER INFORMATION: ornithine
```

```
<400> SEQUENCE: 33

Ser Ser Xaa Phe Xaa Trp Xaa Phe Xaa Ser Ser
1               5                   10
```